(12) United States Patent
Carlson et al.

(10) Patent No.: US 9,079,039 B2
(45) Date of Patent: Jul. 14, 2015

(54) STATE MACHINE FRAMEWORK FOR PROGRAMMING CLOSED-LOOP ALGORITHMS THAT CONTROL THE DELIVERY OF THERAPY TO A PATIENT BY AN IMPLANTABLE MEDICAL DEVICE

(71) Applicant: Medtronic, Inc., Minneapolis, MN (US)

(72) Inventors: David L. Carlson, Fridley, MN (US); Benjamin P. Isaacson, Minneapolis, MN (US); David E. Linde, Corcoran, MN (US)

(73) Assignee: Medtronic, Inc., Minneapolis, MN (US)

( * ) Notice: Subject to any disclaimer, the term of this patent is extended or adjusted under 35 U.S.C. 154(b) by 59 days.

(21) Appl. No.: 13/934,096

(22) Filed: Jul. 2, 2013

(65) Prior Publication Data

US 2015/0012057 A1 Jan. 8, 2015

(51) Int. Cl.
*A61N 1/36* (2006.01)
*A61N 1/372* (2006.01)

(52) U.S. Cl.
CPC .......... *A61N 1/37264* (2013.01); *A61N 1/3606* (2013.01); *A61N 1/36139* (2013.01); *A61N 1/37247* (2013.01)

(58) Field of Classification Search
USPC .......................................................... 607/45
See application file for complete search history.

(56) References Cited

U.S. PATENT DOCUMENTS

| 5,103,819 | A | 4/1992 | Baker et al. |
| 5,692,907 | A | 12/1997 | Glassel et al. |
| 2004/0249299 | A1 | 12/2004 | Cobb |
| 2007/0244408 | A1* | 10/2007 | Wingeier et al. .............. 600/544 |
| 2010/0030094 | A1 | 2/2010 | Lundback |
| 2010/0280579 | A1* | 11/2010 | Denison et al. ................. 607/62 |
| 2013/0218232 | A1 | 8/2013 | Giftakis et al. |

FOREIGN PATENT DOCUMENTS

WO 2009072971 A1 6/2009

OTHER PUBLICATIONS

Yamamoto et al., "On-demand control system for deep brain stimulation for treatment of intention tremor," Neuromodulation 2012; e-pub ahead of print., Oct. 24, 2012, DOI: 10.1111/j.1525-1403.2012.00521.x, 6 pp.

(Continued)

*Primary Examiner* — Paula J Stice
(74) *Attorney, Agent, or Firm* — Shumaker & Sieffert, P.A.

(57) ABSTRACT

This disclosure describes a state machine framework for programming closed-loop algorithms that control the delivery of therapy to a patient by an implantable medical device (IMD). The state machine framework may use one or more programmable state parameters to define at least part of a structure of a state machine that generates one or more therapy decisions based on one or more sensed states of the patient. The state machine framework may include a state machine runtime environment that executes on an IMD and that is configurable to implement a variety of different state machines depending on programmable state parameters that are received from an external device. The techniques of this disclosure may, in some cases, allow IMD developers and/or users to program, change, and/or download new closed-loop control policy algorithms during the lifespan of the IMD without requiring new firmware code to be downloaded onto the IMD.

30 Claims, 37 Drawing Sheets

(56) References Cited

OTHER PUBLICATIONS

Afshar et al., "A translational platform for prototyping closed-loop neuromodulation systems," Frontiers in Neural Circuits, Jan. 22, 2013, 15 pp.

Sun et al., "Responsive Cortical Stimulation for the Treatment of Epilepsy," Neurotherapeutics : The Journal of the American Society for Experimental NeuroTherapeutics, vol. 5, pp. 68-74, Jan. 2008.

Nelson et al., "Real-Time Feature Recognition in Medical Data," AAAI technical Report SS-94-01, 1994, pp. 95-99.

Carlson et al., "A Flexible Algorithm Framework for Closed-Loop Neuromodulation Research Systems," 35th Annual International Conference of the IEEE EMBS, Osaka, Japan Jul. 3-7, 2013, pp. 6146-6150.

IAR Systems, "IAR visualState" www.iar.com/vs/, archived on Feb. 11, 2013, 6 pp.

eVelopers Corporation, "Java Finite State Machine Framework," unimod.sourceforge.net/fsm-framework.html, archived on Feb. 11, 2013, 10 pp.

MathWorks, "Stateflow," www.mathworks.com/products/stateflow, archived on Feb. 18, 2013, 1 pp.

\* cited by examiner

| State0: Initialize | | | | | |
|---|---|---|---|---|---|
| Stim Prgm | = | *Prgm1* | | | |
| Stim Ctrl | = | *Stim Off* | | | |
| Stim Flags | = | *None* | | | |
| Exit Conditions | | | | | NextSt |
| TimerCount | = | *1 (tic)* | | | *State1* |
| | CL1 | CL2 | CL3 | CL4 | M4 |
| Priority1 | X | X | X | X | X |
| Priority2 | X | X | X | X | X | -- |
| Priority3 | X | X | X | X | X | -- |
| Priority4 | X | X | X | X | X | -- |

FIG. 15

| State1: Stim Off/Evaluate CL1 ||||||
|---|---|---|---|---|---|
| Stim Prgm | = | *NC* ||||
| Stim Ctrl | = | *Stim Off* ||||
| Stim Flags | = | *None* ||||
| Exit Conditions |||||| NextSt |
| TimerCount | = | 0 *(disabled)* |||| --- |
| | CL1 | CL2 | CL3 | CL4 | M4 | |
| Priority1 | *1* | X | X | X | X | *State2* |
| Priority2 | X | X | X | X | X | --- |
| Priority3 | X | X | X | X | X | --- |
| Priority4 | X | X | X | X | X | --- |

FIG. 16

| State2: Stim On for 30 secs ||||||
|---|---|---|---|---|---|
| Stim Prgm | = | NC ||||
| Stim Ctrl | = | *Stim On* ||||
| Stim Flags | = | *None* ||||
| Exit Conditions |||||  NextSt |
| TimerCount | = | *30 seconds* |||  *State1* |
|  | CL1 | CL2 | CL3 | CL4 | M4 |
| Priority1 | X | X | X | X | X | --- |
| Priority2 | X | X | X | X | X | --- |
| Priority3 | X | X | X | X | X | --- |
| Priority4 | X | X | X | X | X | --- |

FIG. 17

| State3: Stim Off/Delay | | | | | |
|---|---|---|---|---|---|
| Stim Prgm | = | *NC* | | | |
| Stim Ctrl | = | *Stim Off* | | | |
| Stim Flags | = | *None* | | | |
| Exit Conditions | | | | | NextSt |
| TimerCount | = | *15 seconds* | | | *State1* |
| | CL1 | CL2 | CL3 | CL4 | M4 |
| Priority1 | X | X | X | X | X | --- |
| Priority2 | X | X | X | X | X | --- |
| Priority3 | X | X | X | X | X | --- |
| Priority4 | X | X | X | X | X | --- |

FIG. 19

| State2: Stim On for 30 secs | | | | | |
|---|---|---|---|---|---|
| Stim Prgm | = | *NC* | | | |
| Stim Ctrl | = | Stim On | | | |
| Stim Flags | = | *None* | | | |
| Exit Conditions | | | | | NextSt |
| TimerCount | = | *30 seconds* | | | *State3* |
| | CL1 | CL2 | CL3 | CL4 | M4 |
| Priority1 | X | X | X | X | X | --- |
| Priority2 | X | X | X | X | X | --- |
| Priority3 | X | X | X | X | X | --- |
| Priority4 | X | X | X | X | X | --- |

FIG. 20

| State 5 (Suppr Check) | | | |
|---|---|---|---|
| Entry Actions | | | |
| Stim prog | NC | | |
| Stim control | NC | | |
| Inc/Dec Flags | None | | |
| Timer control | NS | | |

| Condition | | | | Next State |
|---|---|---|---|---|
| AD Det | Suppr | Timer exp | | |
| 1 | X | X | | 2 |
| 0 | 0 | X | | 6 |
| 0 | 1 | X | | 7 |

Inputs →

FIG. 28

| State | Prog | Stim Ctrl | Inc/Dec Flag | Timer | AD Det (CL1) | Suppr (CL2) | Timer Exp | Next State |
|---|---|---|---|---|---|---|---|---|
| 0 (Init) | P1 | OFF | none | Set 300 | 1 | X | X | 2 |
|  |  |  |  |  | 0 | X | 1 | 1 |
| 1 (Stim ON) | NC | ON | none | Set 50 | 1 | X | X | 2 |
|  |  |  |  |  | 0 | X | 1 | 4 |
| 2 (AD Det) | NC | OFF | Set Dec | 0 (none) | 0 | X | X | 3 |
| 3 (post-AD wait) | NC | NC | none | Set 450 | 1 | X | X | 2 |
|  |  |  |  |  | 0 | X | 1 | 7 |
| 4 (Stim OFF timer) | NC | OFF | none | Set 150 | 1 | X | X | 2 |
|  |  |  |  |  | 0 | X | 1 | 5 |
| 5 (suppr check) | NC | NC | none | 0 (none) | 1 | X | X | 2 |
|  |  |  |  |  | 0 | 0 | X | 6 |
|  |  |  |  |  | 0 | 1 | X | 7 |
| 6 (Set Inc) | NC | NC | Set Inc | Set 1 | X | X | 1 | 1 |
| 7 (wait for end of suppr) | NC | NC | DEC | 0 (none) | 1 | X | X | 2 |
|  |  |  |  |  | 0 | 0 | X | 1 |

FIG. 31

| State | Stim Prog | ON/OFF | INC/DEC | Timer | CL1 | CL2 | CL3 | CL4 | Next |
|---|---|---|---|---|---|---|---|---|---|
| 0 | P1 | OFF | - | 300 | - | - | - | - | 1 |
|  |  |  |  |  | T | - | - | - | 2 |
| 1 | NC | ON | - | 50 | - | - | - | - | 4 |
|  |  |  |  |  | T | - | - | - | 2 |
| 2 | NC | OFF | DEC | - | F | - | - | - | 3 |
| 3 | NC | NC | - | 450 | - | - | - | - | 7 |
|  |  |  |  |  | T | - | - | - | 2 |
| 4 | NC | OFF | - | 150 | - | - | - | - | 5 |
|  |  |  |  |  | T | - | - | - | 2 |
| 5 | NC | NC | - | - | T | - | - | - | 2 |
|  |  |  |  |  | - | F | - | - | 6 |
|  |  |  |  |  | - | T | - | - | 7 |
| 6 | NC | NC | INC | 1 | - | - | - | - | 1 |
| 7 | NC | NC | DEC | - | T | - | - | - | 2 |
|  |  |  |  |  | - | F | - | - | 1 |

FIG. 32

STATE MACHINE FRAMEWORK FOR PROGRAMMING CLOSED-LOOP ALGORITHMS THAT CONTROL THE DELIVERY OF THERAPY TO A PATIENT BY AN IMPLANTABLE MEDICAL DEVICE

TECHNICAL FIELD

The disclosure relates to medical devices and, more particularly, to medical devices that deliver therapy.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads.

Medical electrical stimulators may be used to deliver electrical stimulation therapy to patients to relieve a variety of symptoms or conditions such as chronic pain, tremor, Parkinson's disease, depression, epilepsy, urinary or fecal incontinence, pelvic pain, sexual dysfunction, obesity, or gastroparesis. An electrical stimulator may be configured to deliver electrical stimulation therapy via leads that include electrodes implantable proximate to the spinal cord, pelvic nerves, gastrointestinal organs, peripheral nerves, or within the brain of a patient. Stimulation proximate the spinal cord and within the brain are often referred to as spinal cord stimulation (SCS) and deep brain stimulation (DBS), respectively.

SUMMARY

This disclosure describes a state machine framework for programming closed-loop algorithms that control the delivery of therapy to a patient by an implantable medical device (IMD). The state machine framework may use one or more programmable state parameters to define at least part of a structure of a state machine that generates one or more therapy decisions based on one or more sensed states of the patient. The state machine framework may include a state machine runtime environment that executes on an IMD and that is configurable to implement a variety of different state machines depending on programmable state parameters that are received from an external device. Using a state machine runtime environment that operates based on downloadable state parameters may allow, in some examples, different state machines to be implemented on an IMD at different times with the same generic, state machine-independent firmware code. In this way, the techniques of this disclosure may allow IMD developers and/or users to program, change, and/or download new closed-loop control policy algorithms during the lifespan of the IMD without requiring new firmware code to be downloaded onto the IMD.

In one example, this disclosure describes a method that controls delivery of therapy by an implantable medical device (IMD) to a patient based on a state machine that generates one or more therapy decisions based on one or more sensed states of the patient. The state machine may have a structure that is defined at least in part by one or more programmable state parameters.

In another example, this disclosure describes an implantable medical device (IMD) that includes one or more processors configured to control delivery of therapy by the IMD to a patient based on a state machine that generates one or more therapy decisions based on one or more sensed states of the patient. The state machine may have a structure that is defined at least in part by one or more programmable state parameters.

In an additional example, this disclosure describes a system that includes an implantable medical device (IMD) configured to control delivery of therapy by the IMD to a patient based on a state machine that generates one or more therapy decisions based on one or more sensed states of the patient. The state machine may have a structure that is defined at least in part by one or more programmable state parameters. The system may further include a programmer configured to receive the programmable state parameters from a user via a user interface, and to transmit the programmable state parameters from the programmer to the IMD.

The details of one or more aspects of the disclosure are set forth in the accompanying drawings and the description below. Other features, objects, and advantages will be apparent from the description and drawings, and from the claims.

BRIEF DESCRIPTION OF DRAWINGS

FIGS. 15-17 are conceptual diagrams illustrating example state framework dialog boxes in which state parameters have been entered for the state diagram illustrated in FIG. 14.

FIG. 19 is a conceptual diagram illustrating an example state framework dialog box in which state parameters have been entered for State 3 of the state diagram illustrated in FIG. 18.

FIG. 20 is a conceptual diagram illustrating an example state framework dialog box in which state parameters have been entered for State 2 of the state diagram illustrated in FIG. 18.

FIGS. 23-30 are conceptual diagrams illustrating example state framework dialog boxes in which state parameters have been entered for the state diagram illustrated in FIG. 21.

FIG. 31 is a state transition table corresponding to the state diagram illustrated in FIG. 21.

FIG. 32 is a state transition table corresponding to the state diagram illustrated in FIG. 21.

DETAILED DESCRIPTION

Figure 1:
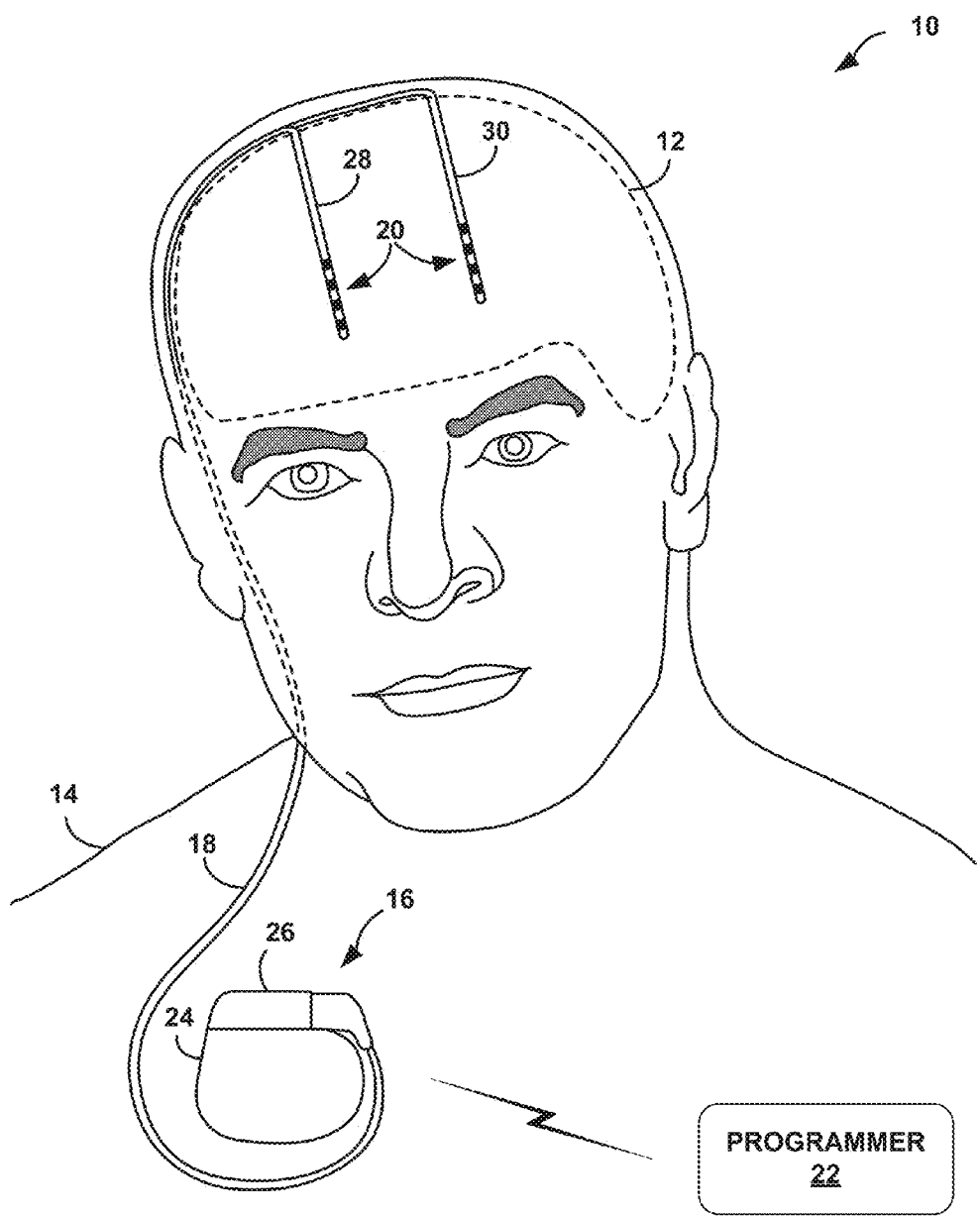
FIG. 1 is a conceptual diagram illustrating an example therapy system that may be used to implement the state machine framework of this disclosure.

This disclosure describes a state machine framework for programming closed-loop algorithms that control the delivery of therapy to a patient by an implantable medical device (IMD). The state machine framework may use one or more programmable state parameters to define at least part of a structure of a state machine that generates one or more therapy decisions based on one or more sensed states of the patient. The state machine framework may include a state machine runtime environment that executes on an IMD and that is configurable to implement a variety of different state machines depending on programmable state parameters that are received from an external device. Using a state machine runtime environment that operates based on downloadable state parameters may allow, in some examples, different state machines to be implemented on an IMD at different times with the same generic, state machine-independent firmware code. In this way, the techniques of this disclosure may allow IMD developers and/or users to program, change, and/or download new closed-loop control policy algorithms during the lifespan of the IMD without requiring new firmware code to be downloaded onto the IMD.

In some examples, the therapy decisions generated by a programmable state machine according to this disclosure may include selecting one or more stimulation programs from a set of stimulation programs to use for delivering electrical stimulation therapy to a patient, determining whether to enable or disable the delivery of electrical stimulation therapy to the patient, determining whether to increase, decrease, or keep constant the stimulation amplitude used for delivering electrical stimulation therapy, and/or whether to adjust other stimulation parameters (e.g., pulse width, waveform shape, electrode combination, electrode configuration, stimulation burst frequency, duty cycle, etc.) that are used for delivering electrical stimulation therapy. Other therapy decisions may also be used in addition to or in lieu of the above-mentioned therapy decisions.

In some examples, the electrical stimulation therapy delivered to the patient may be neurological stimulation therapy and at least some of the sensed states of the patient may be sensed neurological states of the patient. In further examples, the electrical stimulation therapy delivered to the patient may be electrical stimulation therapy delivered to a brain of the patient, and at least some of the sensed states of the patient may be sensed brain states of the patient.

As discussed above, the programmable state parameters may define at least part of the structure of a state machine. In some examples, the structure of a state machine may refer to one or more of the following: the number of states in the state machine, the configuration of state transitions that occur between the different states in the state machine, the entry actions for each of the states in the state machine, and the exit conditions for each of the states in the state machine.

In some examples, the structure of a state machine may be defined at least in part by a next state transfer function that determines which state is the next state to execute based on the current state and one or more inputs to the state machine. In other words, the structure of the state machine may specify under what conditions transitions between the various states in the state machine are to occur. In some cases, each of the inputs used to determine the next state may correspond to one or more sensed states of the patient (e.g., one or more signals generated by one or more classifiers that classify sensed states of the patient). In additional examples, the structure of the state machine may be defined at least in part by one or more actions that occur when operating in each of the states. In some cases, the actions may include actions that control the delivery of electrical stimulation therapy.

In some examples, the state parameters may include state parameters that specify one or more entry actions for one or more states in the state machine. Entry actions may refer to actions that are performed when entering the state (e.g., transitioning to the state from another state). Example entry actions may include one or more of an action that selects one of a plurality of stimulation programs to be used for delivery of stimulation, an action that turns on the delivery of the stimulation, an action that turns off the delivery of the stimulation, an action that causes no change to an activation state of the stimulation, an action that increases or decreases (e.g., increments or decrements) or otherwise changes one or more stimulation parameters, and an action that causes a timeout to occur if no exit conditions are satisfied after a specified period of time. The stimulation parameters that may be increased or decreased via entry actions may include, in some examples, an amplitude of the stimulation, a pulse width of the stimulation, and a frequency of the stimulation. Other example stimulation parameters that may be changed via entry actions include electrode combination selected to deliver stimulation, electrode configuration (e.g., unipolar, bipolar, multipolar)

used to deliver stimulation, a stimulation waveshape (e.g., pulses and/or waveshapes other than pulses), a stimulation burst frequency or width, the state of a cycling on/off parameter (e.g., with cycling off indicating stimulation is always on and cycling on indicating stimulation is cycled on/off), and duty cycle. In some examples, the entry actions may further include a delay (e.g., blanking period or settling time) that occurs upon entry into a state. In some cases, individual entry actions or groups of entry actions may correspond to therapy decisions made by the state machine. Using state parameters to specify entry actions for the states in a state machine may provide a flexible framework for programming control policy algorithms that are capable changing and/or adjusting stimulation programs based on sensed states of a patient during the execution of the control policy algorithm.

In further examples, the state parameters may include state parameters that specify one or more exit conditions for one or more states in the state machine. An exit condition may specify a condition that is to occur prior to transferring to a next state associated with the exit condition. Each exit condition may include a condition portion that specifies a condition to be evaluated and a next state portion that specifies to which state the state machine is to transition if the condition specified in the condition portion is satisfied. Example exit conditions may include a user-specified combination of one or more of a plurality of state classifier outputs where each of the state classifier outputs is indicative of whether a respective one of one or more physiological states has been detected for the patient based on data received from one or more physiological sensors. Another example exit condition is a timer which, upon expiration, causes the state to transition to another state. Other example exit conditions include exit conditions that specify the time delays between one or more of the states in the state machine, exit conditions that specify whether timeouts are enabled for each of the states in the state machine, and exit conditions that specify the length of timeout for states in the state machine where timeouts are enabled. Using state parameters to specify exit conditions and associated next states for states in a state machine may allow sensed physiological states of a patient to be used to control the execution paths in the state machine.

In additional examples, the state parameters may include state parameters that are indicative of a priority assigned to each of the exit conditions for a particular state. The priority assigned to each of the exit conditions may indicate an order of precedence for the exit conditions in a case where multiple different exit conditions are satisfied when operating in the current state. Assigning priorities to the exit conditions may avoid the need to include every single combination of a set of possible state machine inputs in a data representation of the state machine. In this way, the amount of data needed to represent and/or store the state machine may be reduced.

In some examples, the state machine framework of this disclosure may provide a user interface that is configured to execute on a device external to an IMD (e.g., a programmer) and to receive one or more state parameters that define at least part of the structure of a state machine that generates one or more therapy decisions based on one or more sensed states of the patient. The state machine framework may further provide a telemetry interface and circuitry for transferring the state parameters received via the user interface from the external device to the IMD. The state parameters may, in some examples, be transferred in the form of parameter values instead of firmware code. In this way, a control policy algorithm for an IMD may be able to be programmed and/or reconfigured by an external device without requiring new firmware code to be reloaded onto the IMD.

In some examples, the user interface may provide state-specific data entry dialog boxes that allow a user to enter one or more state parameters associated with a particular state. For example, a user may be able to specify state parameters for a particular state that control entry actions for the state and/or exit conditions for the state. Providing state-specific data entry dialog boxes may allow users to easily and efficiently enter state parameters into the user interface for programming control policy algorithms.

In further examples, the user interface may provide an interactive, graphical representation of a state diagram along with interactive state diagram components. For example, the user interface may graphically represent states nodes and transition arcs (e.g., arrows) connecting the state nodes. In such examples, the user interface may allow users to add and delete state nodes to the state diagram, to add and delete state transition arcs to the state diagram, and to position the state nodes and state transition arcs on the display. In some cases, the user interface may allow users to manipulate the state diagram components using touch screen gestures and/or drag and drop functionality. In further cases, the user interface may allow users to interactively join different states with state transition arcs to generate next state relationships between the different states. In additional cases, the user interface may provide a state-specific data entry dialog box in response to the user clicking on a state. A user interface that includes an interactive, graphical state diagram may provide an intuitive interface for users to configure and build a state machine. In addition, such a user interface may also provide an indication of the status of the state machine execution while it is in progress, to allow users to troubleshoot and understand the behavior of the state machine executing in the IMD.

Development of control policy algorithms for closed-loop neuromodulation systems is in a relatively early stage. The optimal control policy algorithms for many therapies are not fully known at this time. Therefore, it may be desirable for IMD developers to test a variety of control policy algorithms on an IMD. In addition, clinicians or patients may wish to change the control policy algorithm of an IMD during the operating lifespan of the IMD. The size limitations of many IMDs may allow only a limited number of control policy algorithms to be stored in the IMD at a given time. Therefore, it may be desirable for IMD users to be able to program and download different control policy algorithms onto an IMD during the operating lifespan of the IMD. The techniques of this disclosure may provide a flexible framework for programming and testing different control policy algorithms, thereby allowing IMD developers and/or users to program, change, and/or download new closed-loop control policy algorithms during the operating lifespan of the IMD.

In some types of IMDs with embedded firmware, each time a new control policy is to be tested and/or implemented with the IMD, new firmware code corresponding to the new control policy algorithm may need to be downloaded to the IMD via telemetry or other means. Downloading new firmware code onto an IMD each time a new control policy algorithm is to be tested and/or implemented on an IMD may have several drawbacks. For example, it may take a significant amount time to transmit the firmware code to the IMD via telemetry and to verify the new firmware download. As another example, downloading firmware code may shorten the battery life of the IMD due to high current drain during downloading process. Moreover, there is a risk that one or more download retries may need to occur if the firmware download is corrupted or not successfully completed. Retries may add to the time consumed by and the power drain caused by changes in firmware code.

Each new firmware version may require a firmware development, verification, test, and approval cycle. Further, the software for external instruments may need to be changed to support new algorithm parameters. Thus, downloading new firmware code onto an IMD each time a new control policy algorithm is to be tested and/or implemented on an IMD may add a considerable burden to the IMD development process.

The techniques of this disclosure may, in some examples, be used to program, change, and/or download a control policy algorithm implemented by an IMD without requiring new firmware code to be downloaded to the IMD. Instead of downloading firmware each time a new control policy algorithm is to be tested and/or implemented on the IMD, the techniques of this disclosure may, in some examples, download one or more state parameters from an external device to the IMD. The one or more state parameters may define at least part of a control policy algorithm to be implemented by the IMD. A state machine runtime environment executing on the IMD may receive the downloaded state parameters and implement a state machine that is defined by the state parameters. Because the same state machine runtime environment may be configurable to implement a variety of different state machines depending on the downloaded state parameters, the same generic, state machine-independent firmware code may be used to implement different state machines, thereby avoiding the need to download different firmware code onto an IMD each time the therapy delivery control policy algorithms are to be changed on the IMD.

FIG. 1 is a conceptual diagram illustrating an example therapy system 10 that may be used to implement the state machine framework of this disclosure. Therapy system 10 is configured to deliver electrical stimulation therapy to brain 12 of patient 14. Patient 14 may ordinarily, but not necessarily, be a human. Therapy system 10 includes an implantable medical device (IMD) 16, a lead 18, electrodes 20, and a programmer 22

IMD 16 is configured to sense one or more physiological states of patient 14 via one or more sensors, and to deliver electrical stimulation to brain 12 of patient 14 via electrodes 20 based on the sensed physiological states of patient 14. The electrodes 20 used to deliver electrical stimulation may be implantable electrodes that are deployed on one or more implantable medical leads (e.g., lead 18) and, in some cases, deployed on a can electrode. In the example therapy system 10 of FIG. 1, IMD 16 is implanted within a subcutaneous pocket in a clavicle region of patient 14. IMD 16 may be configured to communicate with one or more external devices (e.g., programmer 22). IMD 16 is mechanically and electrically coupled to lead 18 and to electrodes 20 via lead 18. IMD 16 includes a housing 24 and a connector block 26.

Housing 24 is configured to carry components that perform some or all of the functionality attributed to IMD 16 in this disclosure. For example, housing 24 may include electrical circuitry and components that control the operation of IMD 16. Housing 24 may also include one or more power sources (e.g., one or more batteries) to power the electrical components inside of housing 24. In addition, housing 24 may include telemetry circuitry that is configured to communicate with one or more external devices via radio telemetry techniques. Housing 24 may be formed from any material capable of carrying the components that perform the functionality attributed to IMD 16. In some cases, housing 24 may be formed from a conductive material. In additional cases, housing 24 may be a hermetically-sealed housing. Housing 24 is mechanically coupled to connector block 26.

Connector block 26 is configured to mechanically and electrically couple lead 18 to housing 24 of IMD 16. For example, connector block 26 may include a connection port configured to receive a proximal end of lead 18. When the proximal end of lead 18 is inserted into the connection port of connector block 26, connector block 26 may be configured to electrically couple lead 18 to one or more electrical components in housing 24. In some cases, connector block 26 may be formed from a flexible, insulative material. Connector block 26 is mechanically coupled to housing 24.

In some examples, IMD 16 may deliver deep brain stimulation (DBS) or cortical stimulation (CS) therapy to patient 14 via electrodes 20 based on the sensed physiological states of patient 14 to treat any of a variety of neurological disorders or diseases. Example neurological disorders may include depression, dementia, obsessive-compulsive disorder and movement disorders, such as Parkinson's disease, spasticity, epilepsy, and dystonia. DBS also may be useful for treating other patient conditions, such as migraines and obesity.

Lead 18 is configured to mechanically and electrically couple electrodes 20 to IMD 16. A proximal end of lead 18 may be connected to housing 24 of IMD 16. A distal end of lead 18 may include electrodes 20 that are implanted in brain 12 of patient 14. As shown in FIG. 1, lead 18 may traverse from the implant site of IMD 16 along the neck of patient 14 to the cranium of patient 14 to access brain 12. Although the example therapy system 10 of FIG. 1 illustrates a lead 18 that is electrically and mechanically coupled directly to connector block 26, in other examples, lead 18 may be electrically or mechanically coupled indirectly to connector block 26 via one or more lead extensions. In additional examples, therapy system 10 may include multiple implantable leads instead of a single lead 18.

The example lead 18 illustrated in FIG. 1 is a bifurcated lead that includes lead segments 28, 30 at the distal end of lead 18. Lead segments 28, 30 each include a set of electrodes that form a part of electrodes 20. Conductors in the lead body may electrically couple stimulation electrodes located on lead segments 28, 30 to IMD 16. In various examples, lead segments 28, 30 may each carry four, eight, or sixteen electrodes. In the example therapy system 10 if FIG. 1, each of lead segments 28, 30 carries four electrodes that are configured as ring electrodes at different axial positions near the distal ends of lead segments 28, 30. For purposes of simplicity, the remainder of this disclosure may generally refer to electrodes carried on "leads" rather than "lead segments." In additional examples, IMD 16 may be coupled to one or more leads that may or may not be bifurcated. In such examples, the leads may be coupled to lead 18 via a common lead extension or via separate lead extensions.

Lead segments 28, 30 may be implanted within a desired location of brain 12 through respective holes in the cranium of patient 14. In general, lead segments 28, 30 may be placed at any location within brain 12 such that the electrodes located on lead segments 28, 30 are capable of providing electrical stimulation to targeted tissue during treatment. The region of patient 14 to which electrical stimulation is delivered may, in some examples, be selected based on the patient condition or disorder. In the example therapy system 10 of FIG. 1, lead segments 28, 30 are implanted within the right and left hemispheres, respectively, of patient 14 in order to deliver electrical stimulation to one more regions of patient 14. Other example locations for lead segments 28, 30 within brain 12 may include the pedunculopontine nucleus (PPN), thalamus, basal ganglia structures (e.g., globus pallidus, substantia nigra, subthalmic nucleus), zona inserta, fiber tracts, lenticular fasciculus (and branches thereof), ansa lenticularis, and/or the Field of Forel (thalamic fasciculus). In the case of migraines, lead segments 28, 30 may be implanted to provide stimulation to the visual cortex of brain 12 in order to reduce or eliminate migraine headaches afflicting patient 14. Again, the target therapy delivery site may depend upon the patient condition or disorder being treated.

In the example therapy system 10 of FIG. 1, electrodes 20 are ring electrodes. Ring electrodes are commonly used in DBS applications because they are simple to program and are capable of delivering an electrical field to any tissue adjacent to lead segments 28, 30. In other examples, electrodes 20 may have different configurations. For example, electrodes 20 may have a complex electrode array geometry that is capable of producing shaped electrical fields. The complex electrode array geometry may include multiple electrodes (e.g., partial ring or segmented electrodes) around the perimeter of each of electrodes 20, rather than one ring electrode. In this manner, electrical stimulation may be directed in a specific direction from lead segments 28, 30 to enhance therapy efficacy and reduce possible adverse side effects from stimulating a large volume of tissue. In alternative examples, lead segments 28, may have shapes other than elongated cylinders as shown in FIG. 1. For example, lead segments 28, 30 may be paddle leads, spherical leads, bendable leads, or any other type of shape effective in delivering electrical stimulation therapy to patient 14.

Each of electrodes 20 may be configured to deliver electrical stimulation to brain 12 of patient 14 and/or to sense electrical activity that occurs in brain 12 of patient 14. For examples, each of electrodes 20 may be configured to function as a stimulation electrode, a sense electrode, or a combination stimulation/sense electrode. As shown in FIG. 1, each of electrodes 20 is implanted in brain 12 of patient 14. In additional examples, one or more electrodes that are not implanted in brain 12 of patient 14 may be used for sensing and/or for delivery of therapy in addition to or in lieu of electrodes 20. For example, a can electrode that is formed on housing 24 of IMD 16 may be used for the delivery of therapy in combination with electrodes 20.

The electrical stimulation therapy delivered to brain 12 of patient 14 may take the form of constant current or voltage pulses or substantially continuous waveforms. Various parameters of the pulses or waveforms may be defined by a stimulation program. The pulses or waveforms may be delivered substantially continuously or in bursts, segments, or patterns, and may be delivered alone or in combination with pulses or waveforms defined by one or more other stimulation programs.

Programmer 22 is an external computing device that is configured to wirelessly communicate with IMD 16. The wireless communication facilitated by programmer 22 may include transmitting and receiving data and/or controlling the operation of programmer 22. A user, e.g., a clinician and/or patient 14, may use programmer 22 to communicate with IMD 16. In some examples, programmer 22 may be a clinician programmer that a clinician uses to communicate with IMD 16 (e.g., to program one or more therapy programs for IMD 16). In further examples, programmer 22 may be a patient programmer that a patient uses to communicate with IMD 16 (e.g., to select programs, view electrical stimulation parameters, and/or modify electrical stimulation parameters). The clinician programmer may, in some examples, include more programming features than the patient programmer. In other words, certain types of complex and/or sensitive tasks may, in such examples, only be allowed by the clinician programmer to prevent an untrained patient from making undesired changes to IMD 16.

Programmer 22 may be any type of computing device including, for example, a hand-held computing device, a computer workstation, a notebook computer, a tablet computer, a cellular phone, a personal digital assistant (PDA), etc. In some cases, programmer 22 may be implemented on a computing device that executes a software application that enables the computing device to operate as a programmer 22. In some cases, the computing device may include a wireless adapter that enables secure communication between programmer 22 and IMD 16.

Programmer 22 may include a display viewable by the user and an interface for providing input to programmer 22 (i.e., a user input mechanism). For example, programmer 22 may include a small display screen (e.g., a liquid crystal display (LCD) or a light emitting diode (LED) display) that provides information to the user. In addition, programmer 22 may include a touch screen display, keypad, buttons, a peripheral pointing device or another input mechanism that allows the user to navigate through the user interface of programmer 22 and provide input. In cases where the display is a touch screen display, the user may, in some examples, use a stylus or a finger to provide input to the display.

When programmer 22 is configured for use by the clinician, programmer 22 may be used to transmit initial programming information to IMD 16. The programming information may include the type of lead 18, the electrode arrangement of electrodes 20, the position of lead 18 within brain 12, the configuration of an electrode array formed by electrodes 20, programs defining electrical stimulation parameter values, and any other information the clinician desires to program into IMD 16. In some cases, programmer 22 may be configured to upload operational or physiological data stored by IMD 16. For example, the clinician may use programmer 22 to periodically interrogate IMD 16 to evaluate efficacy and, if necessary, modify the programs or create new programs.

Programmer 22 may be used by a clinician to control the delivery of electrical stimulation, such as, e.g., activating electrical stimulation, deactivating electrical stimulation, or adjusting one or more stimulation parameters of therapy being delivered to patient 14. The clinician may also use programmer 22 to store therapy programs within IMD 16. During a programming session, the clinician may determine one or more therapy programs that may provide efficacious therapy to patient 14 in order to address symptoms associated with a disorder of patient 14. Patient 14 may provide feedback to the clinician as to the efficacy of the specific program being evaluated.

When programmer 22 is configured for use by patient 14, programmer 22 may provide patient 14 with a user interface for control of the stimulation therapy delivered by IMD 16. For example, patient 14 may use programmer 22 to start, stop or adjust electrical stimulation therapy. As another example, programmer 22 may permit patient 14 to adjust stimulation parameters of a program such as duration, current or voltage amplitude, pulse width and pulse rate. Patient 14 may also select a program, e.g., from among a plurality of stored programs, as a program to control delivery of stimulation by IMD 16.

Programmer 22 may also provide various indications to patient 14 to alert patient 14 of various operating conditions of IMD 16. For example, IMD 16 may provide an indication of when therapy is being delivered, when a patient input has triggered a change in electrical stimulation parameters or when a power source within programmer 22 and/or IMD 16 needs to be replaced or recharged. For example, programmer 22 may include an alert LED that may flash a message to patient 14 via a programmer display, or may generate an audible sound or somatosensory cue to confirm patient input was received, e.g., to indicate a patient state or to manually modify an electrical stimulation parameter.

Programmer 22 may communicate with IMD 16 and, optionally, another computing device, via wireless communication. Programmer 22 may, for example, communicate via wireless communication with IMD 16 using radio frequency (RF) telemetry techniques known in the art. Programmer 22 may also communicate with another programmer or computing device via a wired or wireless connection using any of a variety of local wireless communication techniques, such as, e.g., RF communication according to the 802.11 or Bluetooth™ specification sets, infrared (IR) communication according to the Infrared Data Association (IRDA) specification set, or other standard or proprietary telemetry protocols. In additional examples, programmer 22 may communicate with other programming or computing devices via exchange of removable media, such as magnetic or optical disks, memory cards or memory sticks. In further examples, programmer 22 may communicate with IMD 16 and another programmer via remote telemetry techniques, a local area network (LAN), a wide area network (WAN), a public switched telephone network (PSTN), or a cellular telephone network, for example. In further examples, programmer 22 may communicate with IMD 16 via a cable. Each of programmer 22 and IMD 16 may include a transceiver to permit bi-directional communication.

According to this disclosure, IMD 16 is configured to control the delivery of therapy to patient 14 based on a state machine that has a structure which is defined at least in part by one or more programmable state parameters. The state machine may generate one or more therapy decisions based on one or more sensed states of patient 14. In some examples, IMD 16 may receive the programmable state parameters from a device other than IMD 16 (e.g., programmer 22). Using a state machine that has a structure which is defined at least in part by one or more programmable state parameters to control the delivery of therapy to patient 14 may allow the execution paths for therapy delivery control policy algorithms to be programmed and/or reconfigured during the operational lifespan of IMD 16.

In some examples, IMD 16 may execute a state machine runtime environment that is configurable to implement a variety of different state machines depending on programmable state parameters that are received from an external device (e.g., programmer 22). The state machine runtime environment, in some cases, may be part of a set of firmware code that is executed by IMD 16. Using a state machine runtime environment that operates based on downloadable state parameters may allow, in some examples, different state machines to be implemented on IMD 16 at different times with the same generic, state machine-independent firmware code executing on IMD 16. In this way, the techniques of this disclosure may allow IMD developers and/or users to program, change, and/or download new closed-loop control policy algorithms during the operational lifespan of IMD 16 without requiring new firmware code to be downloaded onto IMD 16.

In some examples, the therapy decisions generated by the state machine implemented by IMD 16 may include selecting one or more stimulation programs from a set of stimulation programs to use for delivering electrical stimulation therapy to a patient, determining whether to enable or disable the delivery of electrical stimulation therapy to the patient, and/or determining whether to increase, decrease, or keep constant one or more stimulation parameters used for delivering electrical stimulation therapy. Example stimulation parameters that may be adjusted may include, e.g., an amplitude of the stimulation, a pulse width of the stimulation, and a frequency of the stimulation. Other therapy decisions may also be used in addition to or lieu of the above-mentioned therapy decisions.

The inputs to the state machine implemented by IMD 16 may include data indicative of the sensed states of patient 14 (e.g., classified states of patient 14). The data indicative of the sensed states of patient 14 may be generated based on data received from one or more sensors. These sensors may be included in IMD 16 or external to IMD 16. In some examples, the sensors may include inertial sensors (e.g., an accelerometer), chemical sensors, pressure sensors, temperature sensors, optical sensors, impedance sensors, bioelectrical sensors, etc. In some examples, an inertial sensor may be configured to sense and/or detect patient posture, patient activity, patient movement, patient tremor, etc. Bioelectrical sensors may include sensors that sense bioelectrical signals, such as, e.g., local field potential (LPF) signals, electrocardiography (ECG) signals, electromyography (EMG) signals, etc. In some cases, the bioelectrical sensors may sense one or more electrical characteristics of patient 14 via electrodes 20 in order to sense a physiological state of brain 12.

To generate the data indicative of the sensed states of patient 14, IMD 16 may execute one or more classifiers. Each of the classifiers may be configured to detect and/or classify whether patient 14 is in a given state based on physiological data received from one or more sensors, and generate data indicative of whether the given state has been detected for patient 14. Example states that may be classified and/or detected by classifiers executing on IMD 16 may include whether a patient is experiencing a particular patient condition, such as, e.g., a seizure, Parkinson's disease (PD), network suppression, desynchronization, and/or depression. Other example states that may be classified include PD on/off states, and beta-to-gamma ratio states.

Using sensed states of a patient to control therapy decisions generated by a state machine may allow IMD 16 to implement closed-loop control policy algorithms that control the delivery of therapy by IMD 16 to patient 14. Because the state machine has a structure that is defined by downloadable, programmable state parameters, a flexible framework may be provided for downloading and programming closed-loop control policy algorithms onto IMD 16.

In some examples, the electrical stimulation therapy delivered by IMD 16 to patient 14 may be neurological stimulation therapy and at least some of the sensed states of patient 14 may be sensed neurological states of patient 14. In further examples, the electrical stimulation therapy delivered by IMD 16 to patient 14 may be electrical stimulation therapy delivered to brain 12 of patient 14, and at least some of the sensed states of patient 14 may be sensed brain states of patient 14.

As discussed above, the programmable state parameters may define at least part of the structure of the state machine implemented by IMD 16. In some examples, the structure of a state machine may refer to one or more of the following: the number of states in the state machine, the configuration of state transitions that occur between the different states in the state machine, the entry actions for each of the states in the state machine, the exit conditions for each of the states in the state machine, the time delays between each of the states in the state machine, whether timeouts are enabled for each of the states in the state machine, and/or the length of timeout specified for states in the state machine where timeouts are enabled.

In some examples, the structure of a state machine may be defined at least in part by a next state transfer function that determines which state is the next state to execute based on the current state and one or more inputs to the state machine. In other words, the structure of the state machine may specify under what conditions transitions between the various states in the state machine are to occur. In some cases, each of the inputs used to determine the next state may correspond to one or more sensed states of the patient (e.g., one or more signals generated by one or more classifiers that classify sensed states of the patient). In additional examples, the structure of the state machine may be defined at least in part by one or more actions that occur when operating in each of the states. In some cases, the actions may include actions that control the delivery of electrical stimulation therapy.

In some examples, the state parameters may include state parameters that specify one or more entry actions for one or more states in the state machine. Entry actions may refer to actions that are performed when entering the state (e.g., transitioning to the state from another state). Example entry actions may include one or more of an action that selects one of a plurality of stimulation programs to be used for delivery of stimulation, an action that turns on the delivery of the stimulation, an action that turns off the delivery of the stimulation, an action that causes no change to an activation state of the stimulation, an action that increases or decreases (e.g., increments or decrements) one or more stimulation parameters, and an action that causes a timeout to occur if no exit conditions are satisfied after a specified period of time. The stimulation parameters that may be increased or decreased via entry actions may include, in some examples, an amplitude of the stimulation, a pulse width of the stimulation, and a frequency of the stimulation. In some cases, individual entry actions or groups of entry actions may correspond to therapy decisions made by the state machine. Using state parameters to specify entry actions for the states in a state machine may provide a flexible framework for programming control policy algorithms that are capable changing and/or adjusting stimulation programs based on sensed states of a patient during the execution of the control policy algorithm.

In further examples, the state parameters may include state parameters that specify one or more exit conditions for one or more states in the state machine. An exit condition may specify a condition that is to occur prior to transferring to a next state associated with the exit condition. Each exit condition may include a condition portion that specifies a condition to be evaluated and a next state portion that specifies to which state the state machine is to transition if the condition specified in the condition portion is satisfied. Example exit conditions may include a user-specified combination of one or more of a plurality of state classifier outputs where each of the state classifier outputs is indicative of whether a respective one of one or more physiological states has been detected for the patient based on data received from one or more physiological sensors. Another example exit condition is a timer which, when expires, causes the state to transition to another state. Using state parameters to specify exit conditions and associated next states for states in a state machine may allow sensed physiological states of a patient to be used to control the execution paths in the state machine.

In additional examples, the state parameters may include state parameters that are indicative of a priority assigned to each of the exit conditions for a particular state. The priority assigned to each of the exit conditions may indicate an order of precedence for the exit conditions in a case where multiple different exit conditions are satisfied when operating in the current state. Assigning priorities to the exit conditions may avoid the need to include every single combination of a set of possible state machine inputs in a data representation of the state machine. In this way, the amount of data needed to represent and/or store the state machine may be reduced.

Although FIG. 1 shows a fully implantable IMD 16, the state machine framework techniques described in this disclosure may be applied to medical devices that are external to patient 14, but have electrodes deployed via percutaneously implantable leads. In addition, this disclosure is not limited to the configuration of leads and electrodes shown in FIG. 1, but in other examples may include more or less leads, more or less electrodes, and electrodes disposed on other locations besides an implantable lead (e.g., an electrode located on a housing 24 of IMD 16 (i.e., a "can" or "case" electrode)). In addition, in some cases, implantable electrodes may be deployed on a leadless implantable medical device. Although the example techniques of this disclosure are primarily described with respect to medical devices that deliver DBS or CS therapy, the techniques of this disclosure may also be applied to other medical devices including, e.g., medical devices that provide spinal cord stimulation therapy, medical devices that provide gastroenterological therapy (e.g., gastro/urology therapy) and/or medical devices that deliver drug therapy, optical therapy, and/or ultrasound stimulation therapy.

Figure 2:
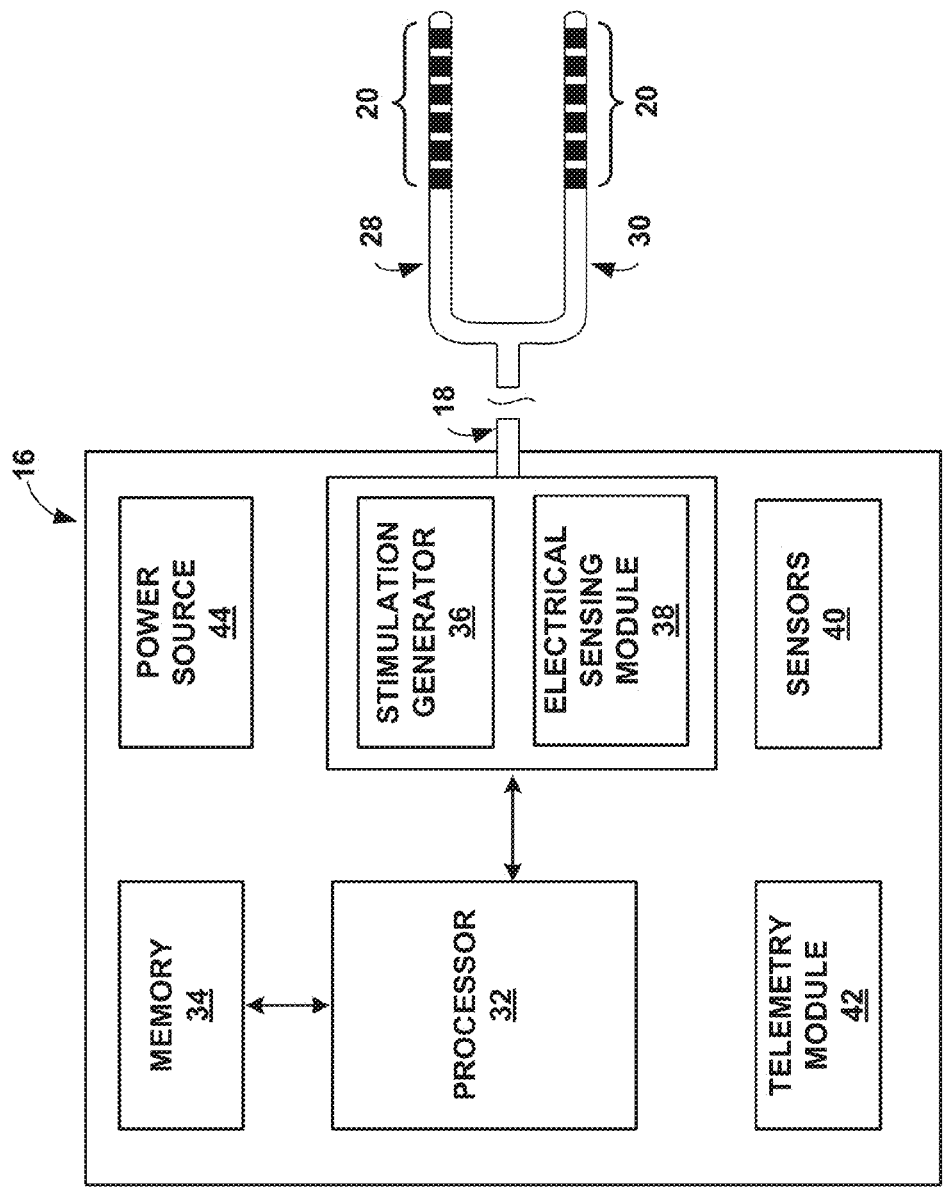
FIG. 2 is a functional block diagram illustrating the implantable medical device (IMD) of FIG. 1 in greater detail.

FIG. 2 is a functional block diagram illustrating the IMD 16 of FIG. 1 in greater detail. IMD 16 is configured to deliver electrical stimulation therapy to patient 14 based on one or more sensed states of patient 14. IMD 16 includes a processor 32, a memory 34, a stimulation generator 36, an electrical sensing module 38, sensors 40, a telemetry module 42 and a power source 44. Each of the components included in IMD 16 may be disposed in housing 24 of IMD 16. Stimulation generator 36 and electrical sensing module 38 are electrically coupled to electrodes 20 via lead 18.

Processor 32 is configured to control the operation of IMD 16 to perform the functions attributed to IMD 16 in this disclosure. For example, processor 32 may control IMD 16 to sense one or more states of patient 14, and to deliver electrical stimulation to brain 12 of patient 14 based on the sensed states of patient 14. To control the delivery of electrical stimulation based on the sensed states of patient 14, processor 32 may execute a state machine framework that is configured to control delivery of therapy by IMD 16 based on a state machine. The state machine may generate one or more therapy decisions based on one or more sensed states of patient 14. The state machine may have a structure that is defined at least in part by one or more programmable state parameters. In some cases, processor 32 may be configured to receive the programmable state parameters from a device other than IMD 16 (i.e., an external device (e.g., programmer 22)) via telemetry module 42.

In some examples, the state machine may define a control policy algorithm for controlling the delivery of therapy based on sensed and/or classified physiological states of patient 14. In such examples, processor 32 may control the delivery of therapy in accordance with the control policy algorithm defined by the programmable state machine.

To control IMD 16 to deliver electrical stimulation therapy, processor 32 may cause stimulation generator 36 to deliver electrical stimulation therapy to one or more tissue sites of brain 12 of patient 14 via lead 18. In some cases, processor 32 may subdivide electrodes 20 into different subsets of electrodes and cause each of the different subsets of electrodes to deliver electrical stimulation to a respective one of a plurality of target tissue sites. For example, processor 32 may cause stimulation generator 36 to deliver electrical stimulation to a first target tissue site via a first subset of electrodes 20 (e.g., electrodes 20 located on lead segment 28) and to deliver electrical stimulation to a second target site via a second subset of electrodes 20 (e.g., electrodes 20 located on lead segment 30). In some cases, the electrical stimulation delivered by each of the subsets of electrodes may be delivered according to a different one of a plurality of therapy programs. For example, the electrical stimulation delivered via the first subset of electrodes may be delivered via a first therapy program, and the electrical stimulation delivered via the second subset of electrodes may be delivered via a second therapy program different than the first therapy program. The electrical stimulation that is delivered via each of the subsets of electrodes 20 may be controlled independently, and may be controlled and delivered either simultaneously or alternatively. In other examples, processor 32 may cause stimulation generator 36 to deliver electrical stimulation to several different target tissue sites with some or all of the same electrodes.

To sense the patient states, processor 32 may use one or both of electrical sensing module 38 and sensors 40. For example, processor 32 may receive physiological data from one or both of electrical sensing module 38 and sensors 40, and classify or detect patient states based on the received physiological data. In some examples, the physiological data may be bioelectrical physiological data (e.g., LPF, ECG, EMG, etc.) received from electrical sensing module 38. In further examples, the physiological data may be data received from sensors 40. In cases where sensors 40 include an inertial sensor, processor 32 may receive inertial physiological data (e.g., data indicative of patient posture, patient activity, patient movement, patient tremor, etc.) received from sensors 40. In some cases, the physiological data may correspond to a physiological signal. Similarly, the bioelectrical physiological data may correspond to a bioelectrical signal, and the inertial physiological data may correspond to an inertial signal. In some cases, the physiological data received by processor 32 may be additionally or alternatively received from one or more sensing modules and sensors that are wirelessly coupled to IMD 16. Such sensors may be fully or partially implanted or may be carried externally by patient 14 (e.g., as in the case of inertial sensors).

In some examples, processor 32 may generate data indicative of the sensed states of patient 14 based on the physiological data received from electrical sensing module 38 and/or sensors 40, and provide the data indicative of the sensed states of patient 14 to the state machine framework. The state machine framework may generate therapy decisions based on the data indicative of the sensed states of patient 14 and a state machine implemented by the state machine framework.

In some examples, processor 32 may receive the data indicative of the physiological data directly from electrical sensing module 38 and/or sensors 40. In further examples, electrical sensing module 38 and/or sensors 40 may store the physiological data in memory 34, and processor 32 may accesses memory 34 to retrieve the physiological data.

The data indicative of the sensed states of patient 14 may, in some examples, take the form of one or more binary values. In such examples, each of the binary values may correspond to a respective one of a plurality of physiological states that may be sensed by patient 14. For example, each of the binary values may be indicative of whether a respective one of one or more physiological states has been detected for patient 14 based on the data received from one or more physiological sensors (i.e., electrical sensing module 38 and/or sensors 40).

To generate the data indicative of the sensed states of patient 14, processor 32 may execute one or more classifiers. Each of the classifiers may be configured to detect and/or classify whether patient 14 is in a given state based on physiological data received from electrical sensing module 38 and/or sensors 40, and generate data indicative of whether the given state has been detected for patient 14. The classifiers may perform computation and/or statistical analysis to detect and/or classify a particular state. Example states that may be classified and/or detected by classifiers executing on IMD 16 may include whether a patient is experiencing a particular patient condition, such as, e.g., a seizure, Parkinson's disease (PD), network suppression, desynchronization, and/or depression. Other example states that may be classified include PD on/off states, and beta-to-gamma ratio states.

In some examples, the classifiers may compare the detected biosignal to one or more previously recorded biosignals. For example, processor 32 may compare a particular characteristic of the detected biosignal to the same characteristic (e.g., a signature biosignal characteristic) of the previously recorded biosignals. Example signal characteristics that can be compared include, but are not limited to, a power level within one or more frequency bands, a ratio of power levels within two or more frequency bands, a peak, average or lowest biosignal amplitude within a particular range of time, a characteristic waveform of the biosignal (e.g. "saw-tooth" wave forms from an EEG signal), a pattern in a biosignal amplitude over time, and the like.

Processor 32 may include, for example, any one or more of a microprocessor, a controller, a digital signal processor (DSP), an application specific integrated circuit (ASIC), a field-programmable gate array (FPGA), and discrete logic circuitry. The functions attributed to processor 32 herein may be embodied as firmware, hardware, software or any combination thereof. In general, components described as processors within IMD 16, programmer 22, or any other device described in this disclosure may each comprise one or more processors, such as one or more microprocessors, DSPs, ASICs, FPGAs, programmable logic circuitry, or the like, either alone or in any suitable combination. The functions attributed to processors described herein may be provided by a hardware device and embodied as software, firmware, hardware, or any combination thereof.

Memory 34 may store data relating to patient 14, such as the patient's name and age, the type of IMD 16 or electrodes 20 implanted within patient 14, medication prescribed to patient 14, and the like. Processor 32 of IMD 16 may also collect diagnostic information and store diagnostic information within memory 34 for future retrieval by a clinician. Diagnostic information may include information or activities indicated by patient 14 using programmer 22, such as changes in symptoms, medication ingestion, or other activities of patient 14. A clinician may review the diagnostic information in a variety of forms, such as timing diagrams or a graph resulting from statistical analysis of diagnostic information, e.g., a bar graph. The clinician may, for example, download diagnostic information from IMD 16 via programmer 22 or another computing device. Diagnostic information may also include calibration routines for electrodes 20 and malfunction algorithms to identify stimulation dysfunctions.

Each program may specify a set of stimulation parameters, such as amplitude, pulse width and pulse rate, if applicable. For a continuous waveform, parameters may include amplitude and frequency. In addition, each program may specify a particular electrode combination for delivery of stimulation, and an electrode configuration in terms of the polarities and regulated/unregulated status of the electrodes. Again, the electrode combination may specify particular electrodes in a single array or multiple arrays, and on a single lead or among multiple leads.

Memory 34 may store data indicative of a state machine that defines a control policy algorithm for IMD 16. The state machine and/or the control policy algorithm may generate therapy decisions based on one or more sensed states of patient 14. In some examples, the data indicative of the state machine may be stored in the form of a state transition table. The state transition table may, in some examples, include an entry for each state transition in the state machine. Each entry of the state transition table may include, in some examples, state parameters associated with the state transition. For example, each entry of the state transition table may include data indicative of the current state associated with a respective one of the state transitions, data indicative of the next state associated with the respective one of the state transitions, entry actions associated with the current state, and exit conditions associated with the respective one of the state transitions. Storing the state machine in the form of a state transition table with transition-specific entries is merely one example of a format for storing the state machine, and other storage formats may be used.

Memory 34 may include any volatile or non-volatile media, such as a random access memory (RAM), a read only memory (ROM), a non-volatile RAM (NVRAM), electrically erasable programmable ROM (EEPROM), flash memory, and the like. Memory 34 may store instructions for execution by processor 32 and information defining delivery of electrical stimulation to patient 14, such as, but not limited to, therapy programs (e.g., sets of stimulation parameter values) or therapy program groups, information associating therapy programs with one or more sleep stages, and any other information regarding the delivery of therapy to patient 14. Therapy information may be recorded in memory 34 for long-term storage and retrieval by a user. Memory 34 may include separate memories for storing information, such as separate memories for therapy programs, diagnostic information, target tissue site information, and patient information. In some examples, memory 34 stores program instructions that, when executed by processor 32, cause IMD 16 and/or processor 32 to perform the functions attributed to them herein.

Memory 34 may be considered, in some examples, a non-transitory computer-readable storage medium comprising instructions that cause one or more processors, such as, e.g., processor 32, to implement one or more of the example techniques described in this disclosure. The term "non-transitory" may indicate that the storage medium is not embodied in a carrier wave or a propagated signal. However, the term "non-transitory" should not be interpreted to mean that memory 34 is non-movable. As one example, memory 34 may be removed from IMD 16, and moved to another device. In certain examples, a non-transitory storage medium may store data that can, over time, change (e.g., the non-transitory storage medium may be a RAM).

In some examples, memory 34 may include a memory that is configured to store firmware code that executes on IMD 16. The firmware code may be generic, state machine-independent firmware code. For example, the firmware code may implement the state machine runtime environment described in this disclosure that is configurable to implement a variety of different state machines depending on programmable state parameters that are received from an external device. Using a state machine runtime environment that operates based on downloadable state parameters may allow, in some examples, different state machines to be implemented on IMD 16 at different times with the same generic, state machine-independent firmware code executing on IMD 16. In this way, the techniques of this disclosure may allow IMD developers and/or users to program, change, and/or download new closed-loop control policy algorithms during the operational lifespan of IMD 16 without requiring new firmware code to be downloaded onto IMD 16.

In some examples, the firmware code may be stored in a non-volatile memory such as, e.g., an electrically erasable programmable ROM (EEPROM). Processor 32 may execute the firmware code that is stored in memory 34. In some cases, the portion of memory 34 that stores the firmware code may be integrated on the same microchip and/or die as processor 32.

In further examples, the firmware code may include code that is configured to implement one or more of the classifiers of this disclosure. Again, each of the classifiers may be configured to detect and/or classify one or more states of patient 14.

Stimulation generator 36 is configured to generate stimulation pulses or waveforms, and to switch the stimulation across different electrode combinations in response to control signals received from processor 32. In some examples, stimulation generator 36 may include stimulation generation circuitry that generates the stimulation pulses and waveforms, and a switch array that switches stimulation across different electrode combinations. Stimulation generator 36 may produce an electrical stimulation signal in accordance with a program based on control signals from processor 32.

Stimulation generator 36 is electrically coupled to electrodes 20 via conductors included in lead 18 (e.g., conductors included in lead segments 28, 30). If one or more housing ("can") electrodes are provided, stimulation generator 36 may also be electrically coupled to such an electrode via an electrical conductor disposed within housing 24 of IMD 16. A can electrode may be configured as a regulated or unregulated electrode to form an electrode configuration in conjunction with other electrodes 20 located on lead 18.

In some examples, stimulation generator 36 may include a charging circuit that selectively applies energy from power source 44 to a capacitor module for generation and delivery of a supply voltage for generation of a stimulation signal. In addition to capacitors, the capacitor module may include switches. In this manner, the capacitor module may be configurable, e.g., based on signals from processor 32, to store a desired voltage for delivery of stimulation at a voltage or current amplitude specified by a program. For delivery of stimulation pulses, switches within the capacitor module may control the widths of the pulses based on signals from processor 32.

Stimulation generator 36 may be configured to deliver any type of electrical stimulation via electrodes 20. The different types of electrical stimulation may include regulated currents, unregulated currents, regulated voltages and unregulated voltages via electrodes 20. For each of the different electrodes 20, stimulation generator 36 may be configured to deliver the same type or a different type of electrical stimulation.

Electrical sensing module 38 is configured to sense one or more electrical signals indicative of activity within brain 12 of patient 14. In some cases, electrical sensing module 38 may use one or more of electrodes 20 disposed on lead 18 as sense electrodes in order to sense the electrical signals. In other cases, electrical sensing module 38 may use one or more additional electrodes that are not disposed on lead 18 (e.g., electrodes disposed on IMD 16 or another lead) to sense the electrical signals. In some cases, electrical sensing module 38 may include one or more sensors and/or may be a subset of sensors 40.

Example electrical signals that may be sensed by electrical sensing module 38 include local field potential (LPF) signals, electrocardiography (ECG) signals, electromyography (EMG) signals, microelectrode recordings (MER) signals, etc. These signals may be referred to as bioelectrical signals or physiological signals. Electrical sensing module 38 may provide the sensed signals to processor 32 (e.g., classifiers executing on processor 32) for further processing.

Although FIG. 2 illustrates electrical sensing module 38 as being incorporated into a common housing with stimulation generator 36 and processor 32, in other examples, electrical sensing module 38 may be in a separate housing from IMD 16 and may communicate with processor 32 via wired or wireless communication techniques. Electrical sensing module 38 may use the same or different electrodes to sense one or more biosignals of brain 12 as that which are used to deliver electrical stimulation generated by stimulation generator 36 to patient 14.

In addition to or instead of monitoring biosignals of patient 14 via electrodes 20 included in lead 18, processor 32 may directly or indirectly receive biosignals indicative of electrical activity within brain 12 from electrodes coupled to another lead that is electrically coupled to electrical sensing module 38, biosignals from electrodes coupled to an outer housing of IMD 16 and electrically coupled to electrical sensing module 38, and/or biosignals from a sensing module that is separate from IMD 16.

Sensors 40 are configured to sense one or more electrical signals indicative of physical activity of patient 14. Sensors 40 may include, for example, inertial sensors (e.g., an accelerometer), chemical sensors, pressure sensors, temperature sensors, optical sensors, impedance sensors, bioelectrical sensors, etc. In some examples, an inertial sensor may be configured to sense and/or detect patient posture, patient activity, patient movement, patient tremor, etc. Bioelectrical sensors may include sensors that sense bioelectrical signals, such as, e.g., local field potential (LPF) signals, electrocardiography (ECG) signals, electromyography (EMG) signals, etc. The signals generated by sensors 40 may include, for examples, signals indicative of the posture of patient 14, signals indicative of the activity of patient 14, signals indicative of the acceleration of patient 14, and signals indicative of the physical movement of patient 14.

In the example shown in FIG. 2, processor 32 may select one or more therapy programs from memory 34 to define the electrical stimulation delivered to patient 14 to treat symptoms of patient 14. Alternatively, programmer 22 may store one or more therapy programs, and processor 32 of IMD 16 may receive selected programs from programmer 22 via telemetry module 42. For example, a processor in programmer 22 may select one or more therapy programs from a memory in programmer 22 and transmit the selected therapy program(s) to processor 32, which may then control stimulation generator 36 to deliver therapy according to the selected therapy program(s).

As described above, in the case of electrical stimulation therapy, each of the programs stored in memory 34 may include respective values for a plurality of therapy parameters, such as, e.g., voltage or current amplitude, signal duration, frequency, and electrode configuration (e.g., an indication of the electrodes 20 selected to deliver stimulation and the respective polarity of the electrodes). The therapy programs stored in memory 34 may be generated using programmer 22, e.g., during an initial or follow-up programming session, and received by processor 32 from programmer 22 via telemetry module 42.

According to this disclosure, processor 32 may be able to dynamically change one or more of these therapy parameters based on a state machine and based on one or more sensed states of a patient. For example, the entry actions for the states in the state machine may specify which programs are to be enabled for a given state, which therapy parameters to use for a given state, and/or what changes to make to the therapy parameters for a given state.

Telemetry module 42 is configured to send information to and receive information from one or more devices external to IMD 16. In some examples, telemetry module 42 may use radio frequency (RF) communication techniques to communicate between IMD 16 and one or more external devices (e.g., programmer 22). In additional examples, telemetry module 42 may use proximal inductive interaction communication techniques to communicate between IMD 16 and one or more external devices (e.g., programmer 22). Telemetry module 42 may send information to external programmer 22 on a continuous basis, at periodic intervals, or upon request by IMD 16 or programmer 22. In some examples, telemetry module 42 may be electrically coupled to an antenna to facilitate communication between IMD 16 and programmer 22.

According to this disclosure, telemetry module 42 may be configured to receive from an external device (e.g., programmer 22) one or more state parameters that define at least part of the structure of a state machine. In some examples, telemetry module 42 may receive the state parameters in form of parameter values and not as part of any firmware code. Transferring the state parameters in the form of parameter values instead of firmware code may allow the state machine to be reconfigured and/or reprogrammed without requiring new firmware code to be downloaded to IMD 16 via telemetry module 42.

Power source 44 may be a non-rechargeable primary cell battery or a rechargeable battery and may be coupled to power circuitry. However, the disclosure is not limited to examples in which the power source is a battery. For example, power source 44 may comprise a supercapacitor. In some embodiments, power source 44 may be rechargeable via induction or ultrasonic energy transmission, and include an appropriate circuit for recovering transcutaneously received energy. For example, power source 44 may be coupled to a secondary coil and a rectifier circuit for inductive energy transfer. In additional embodiments, power source 44 may include a small rechargeable circuit and a power generation circuit to produce the operating power. Recharging may be accomplished through proximal inductive interaction between an external charger and an inductive charging coil within IMD 16. In some embodiments, power requirements may be small enough to allow IMD 16 to utilize patient motion at least in part and implement a kinetic energy-scavenging device to trickle charge a rechargeable battery. A voltage regulator may generate one or more regulated voltages using the battery power.

Figure 3:
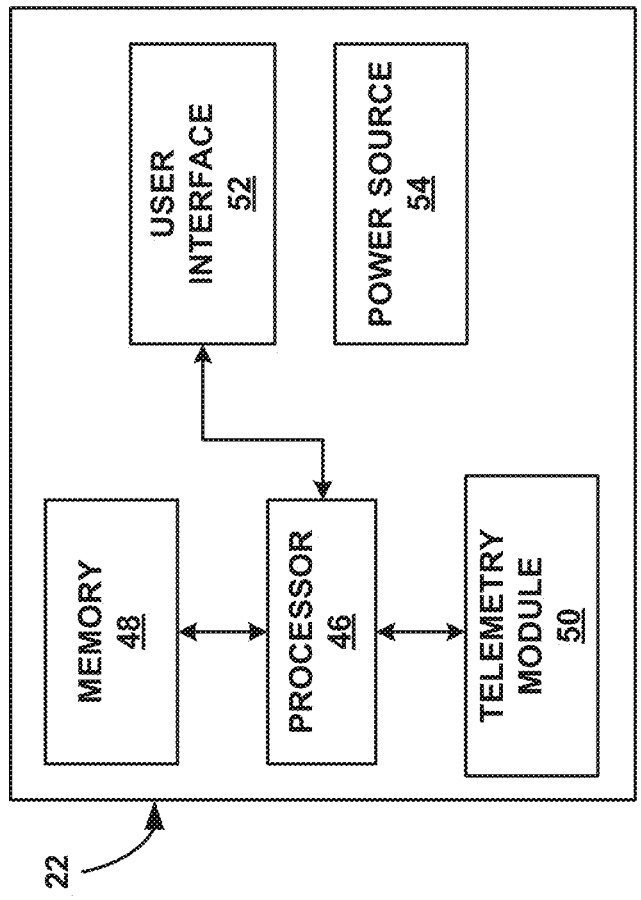
FIG. 3 is a functional block diagram illustrating the programmer of FIG. 1 in greater detail.

FIG. 3 is a functional block diagram illustrating the programmer 22 of FIG. 1 in greater detail. Programmer 22 may correspond to one or both of a patient programmer and a clinician programmer. Programmer 22 includes processor 46, memory 48, telemetry module 50, user interface 52, and power source 54. In general, processor 46 controls user interface 52, stores and retrieves data to and from memory 48, and controls transmission of data to and from IMD 16 via telemetry module 50. Processor 46 may take the form of one or more microprocessors, controllers, DSPs, ASICS, FPGAs, or equivalent discrete or integrated logic circuitry. The functions attributed to processor 46 herein may be embodied as software, firmware, hardware or any combination thereof.

Memory 48 may store instructions that cause processor 46 to provide various aspects of the functionality ascribed to programmer 22 herein. Memory 48 may include any fixed or removable magnetic, optical, or electrical media, such as RAM, ROM, CD-ROM, magnetic disks, EEPROM, or the like. Memory 48 may also include a removable memory portion that may be used to provide memory updates or increases in memory capacities. A removable memory may also allow patient data to be easily transferred to another computing device, or to be removed before programmer 22 is used to program therapy for another patient. Memory 48 may store information that controls operation of IMD 16, such as therapy delivery values. In addition, memory 48 may store state parameters received from user interface 52.

A clinician or patient 14 may interact with user interface 52 in order to, for example, manually select, change or modify programs, adjust voltage or current amplitude, provide efficacy feedback, or view stimulation data. User interface 52 may include a screen and one or more input buttons that allow external programmer 22 to receive input from a user. The screen may be a liquid crystal display (LCD), plasma display, dot matrix display, or touch screen. The input buttons may include a touch pad, increase and decrease buttons, emergency shut off button, and other input media needed to control the stimulation therapy.

Telemetry module 50 facilitates the transfer of data to and from IMD 16. Telemetry module 50 may communicate automatically with IMD 16 at a scheduled time or when the telemetry module 50 detects the proximity of IMD 16. Alternatively, telemetry module 50 may communicate with IMD 16 when signaled by a user through user interface 52. To support RF communication, telemetry module 50 may include appropriate electronic components, such as amplifiers, filters, mixers, encoders, decoders, and the like.

Programmer 22 may communicate wirelessly with implantable IMD 16 using, for example, RF communication or proximal inductive interaction. This wireless communication is possible through the use of telemetry module 50 which may be coupled to an internal antenna or an external antenna. Telemetry module 50 may be similar to telemetry module 50 of implantable IMD 16.

Programmer 22 may also be configured to communicate with another computing device via wireless communication techniques, or direct communication through a wired, e.g., network, connection. Examples of local wireless communication techniques that may be employed to facilitate communication between programmer 22 and another computing device include RF communication based on the 802.11 or Bluetooth specification sets, infrared communication, e.g., based on the IrDA standard.

Power source 54 delivers operating power to the components of programmer 22. Power source 54 may be a rechargeable battery, such as a lithium ion or nickel metal hydride battery. Other rechargeable or conventional batteries may also be used. In some cases, external programmer 22 may be used when coupled to an alternating current (AC) outlet, i.e., AC line power, either directly or via an AC/DC adapter. Power source 54 may include circuitry to monitor power remaining within a battery. In this manner, user interface 52 may provide a current battery level indicator or low battery level indicator when the battery needs to be replaced or recharged. In some cases, power source 54 may be capable of estimating the remaining time of operation using the current battery.

According to this disclosure, user interface 52 of programmer 22 may be configured to receive one or more state parameters that define at least part of a structure of a state machine that generates one or more therapy decisions based on one or more sensed states of patient 14. In general, user interface 52 may implement any of the user interfaces described in this disclosure as well as other graphical user interfaces and/or text-based user interfaces for receiving state parameters.

In response to receiving the state parameters, telemetry module 50 of programmer 22 may transfer and/or download the received state parameters to IMD 16. The state parameters may, in some examples, be transferred in the form of parameter values instead of firmware code. In this way, a control policy algorithm for IMD 16 may be able to be programmed and/or reconfigured by an external device without requiring new firmware code to be reloaded onto IMD 16.

In some examples, user interface 52 may provide state-specific data entry dialog boxes that allow a user to enter one or more state parameters associated with a particular state. For example, a user may be able to specify state parameters for a particular state that control entry actions for the state and/or exit conditions for the state. Providing state-specific data entry dialog boxes may allow users to easily and efficiently enter state parameters into user interface 52 for programming control policy algorithms.

In further examples, user interface 52 may provide an interactive, graphical representation of a state diagram along with interactive state diagram components. For example, user interface 52 may graphically represent states nodes and transition arcs (e.g., arrows) connecting the state nodes. In such examples, user interface 52 may allow users to add and delete state nodes to the state diagram, to add and delete state transition arcs to the state diagram, and to position the state nodes and state transition arcs on a display. In some cases, user interface 52 may allow users to manipulate the state diagram components using drag and drop functionality. In further cases, user interface 52 may allow users to interactively join different states with state transition arcs to generate next state relationships between the different states. In additional cases, user interface 52 may provide a state-specific dialog box in response to the user clicking on a state. A user interface that includes an interactive, graphical state diagram may provide an intuitive interface for users to configure and build a state machine.

Figure 4:
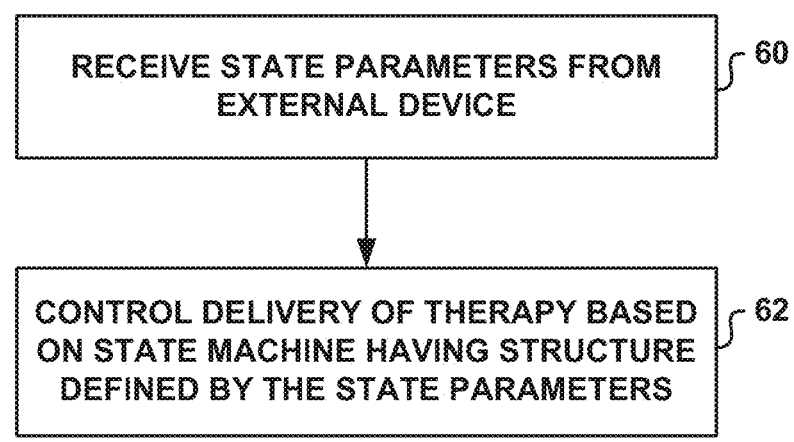
FIG. 4 is a flow diagram illustrating an example technique for controlling the delivery of therapy by a medical device according to this disclosure.

FIG. 4 is a flow diagram illustrating an example technique for controlling the delivery of therapy by a medical device according to this disclosure. The example technique shown in FIG. 4 may be used in any of the implantable medical devices described in this disclosure as well as in other implantable and non-implantable medical devices.

IMD 16 receives one or more programmable state parameters from an external device (60). The external device may be a device other than IMD 16 (e.g., programmer 22). IMD 16 controls the delivery of therapy by IMD 16 to patient 14 based on a state machine having a structure that is defined at least in part by the one or more programmable state parameters (62). The state machine may generate one or more therapy decisions based on one or more sensed states of patient 14.

Figure 5:
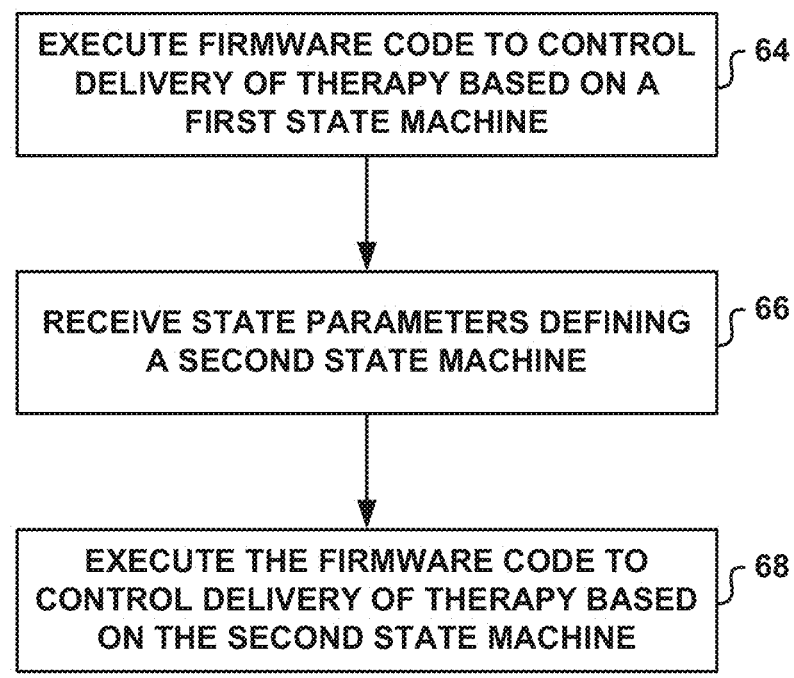
FIG. 5 is a flow diagram illustrating another example technique for controlling the delivery of therapy by a medical device according to this disclosure.

FIG. 5 is a flow diagram illustrating another example technique for controlling the delivery of therapy by a medical device according to this disclosure. The example technique shown in FIG. 5 may be used in any of the implantable medical devices described in this disclosure as well as in other implantable and non-implantable medical devices.

IMD 16 executes firmware code to control the delivery of therapy based on a first state machine (64). IMD 16 receives one or more state parameters from a device other than IMD 16 (66). In some examples, the device other than IMD 16 may be programmer 22. The one or more state parameters may define a second state machine (e.g., define a structure of the second state machine). The second state machine may be different than the first state machine. For example, the structure of the second state machine may be different than the structure of the first state machine. In some examples, the structure of a state machine may refer to one or more of the following: the number of states in the state machine, the configuration of state transitions that occur between the different states in the state machine, the entry actions for each of the states in the state machine, and/or the exit conditions for each of the states in the state machine.

IMD 16 executes firmware code to control the delivery of therapy based on the second state machine (68). The firmware code that is used to control delivery of therapy based on the second state machine may be the same firmware code that is used to control delivery of therapy based on the first state machine. For example, the firmware code may implement a generic, state-machine independent state machine runtime environment as described in this disclosure. Example state machine runtime environments are described in this disclosure with respect to FIGS. 6-9.

In some cases, the firmware code may be configurable to implement a plurality of different state machines. The state machine that is implemented by the firmware code may have a structure that is defined by the programmable state parameters.

Figure 6:
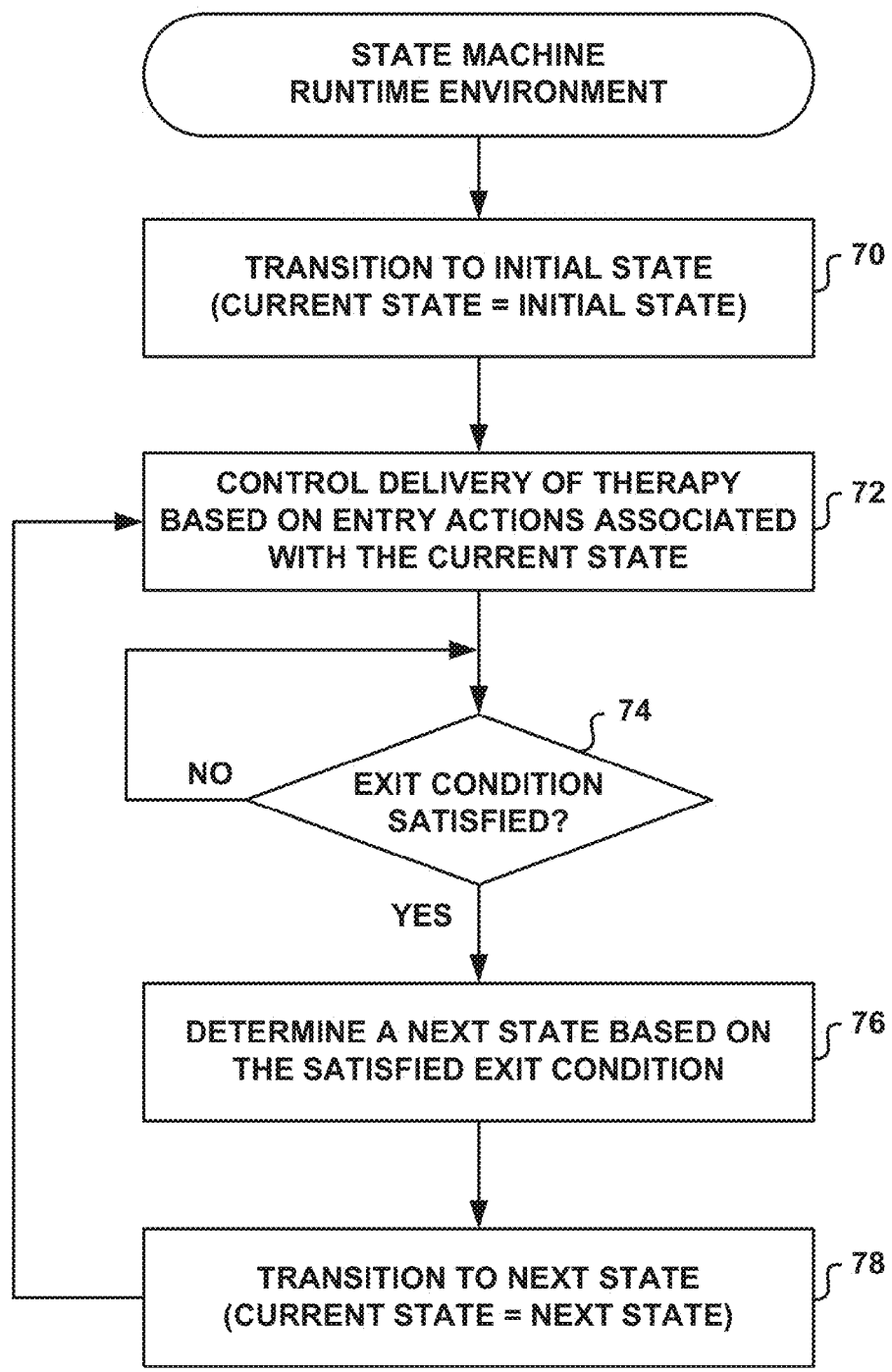
FIG. 6 is a flow diagram illustrating an example state machine runtime environment according to this disclosure.

FIG. 6 is a flow diagram illustrating an example state machine runtime environment according to this disclosure. In some examples, the state machine runtime environment may be embodied in firmware that is stored in IMD 16 (e.g., memory 34) and executed on IMD 16 (e.g., processor 32). In further examples, the state machine runtime environment may be hardware implemented, or any combination of hardware, software, and/or firmware.

IMD 16 transitions to an initial state of a state machine such that the initial state of the state machine becomes the current state (70). IMD 16 controls the delivery of therapy by IMD 16 based on one or more entry actions that are associated with the current state in the state machine (72). The one or more entry actions associated with the current state may be specified by programmable state parameters that are received from an external device (e.g., programmer 22).

IMD 16 determines whether one or more exit conditions that are associated with the current state are satisfied (74). The one or more exit conditions associated with the current state may be specified by the programmable state parameters that are received from an external device (e.g., programmer 22). If at least one of the exit conditions is satisfied, IMD 16 may proceed to process box 76. If no exit conditions are satisfied, then IMD 16 may repeat decision box 74 until one of the exit conditions is satisfied. In other words, IMD 16 may continue to control the delivery therapy according to the entry actions specified for the current state and continue to determine whether any exit conditions are satisfied until at least one of the exit conditions is satisfied. In cases where a timeout is enabled, if the timeout timer expires prior to any exit conditions being satisfied, then IMD 16 may transition to a next state specified by the timeout.

In response to determining that at least one of the exit conditions is satisfied for the current state, IMD 16 determines a next state of the state machine based on the at least one of exit conditions that is satisfied (76). The next state may be associated with the exit condition that is satisfied and may be specified by the programmable state parameters that are received from an external device (e.g., programmer 22). For example, the programmable state parameters may specify a next state for each of the exit conditions, and IMD 16 may select the next state that corresponds to the exit condition that is satisfied. In some cases, one or more of the exit conditions may specify a combination of one or more sensed states of the patient that are needed to satisfy the condition.

In some examples, for at least some of the states in the state machine, the programmable state parameters may specify multiple exit conditions that are capable of being satisfied during the same processing cycle. In such examples, the programmable state parameters may specify a priority for each of the exit conditions (e.g., an order of precedence for the exit conditions). If multiple exit conditions are satisfied during the same processing cycle while operating in a particular state, then IMD 16 may select the satisfied exit condition with the highest priority as the exit condition from which to determine the next state, and determine the next state based on the selected exit condition.

In some cases, when the programmable state parameters are transferred and/or stored, the exit conditions may be transferred and/or stored in a particular order. In such cases, the order in which the exit conditions are transferred and/or stored may, in some examples, determine the priority of the exit conditions. For example, the first exit condition for a state may have the highest priority for that state and the last exit condition for a state may have the lowest priority for that state.

IMD 16 transitions to the next state associated with the satisfied exit condition such that the next state becomes the current state (78). IMD 16 may proceed to process box 72 where IMD 16 controls the delivery of therapy by IMD 16 based on one or more entry actions that are associated with the current state in the state machine. Processing may continue to cycle through the states of the state machine until execution of the control policy has ceased.

Figure 7:
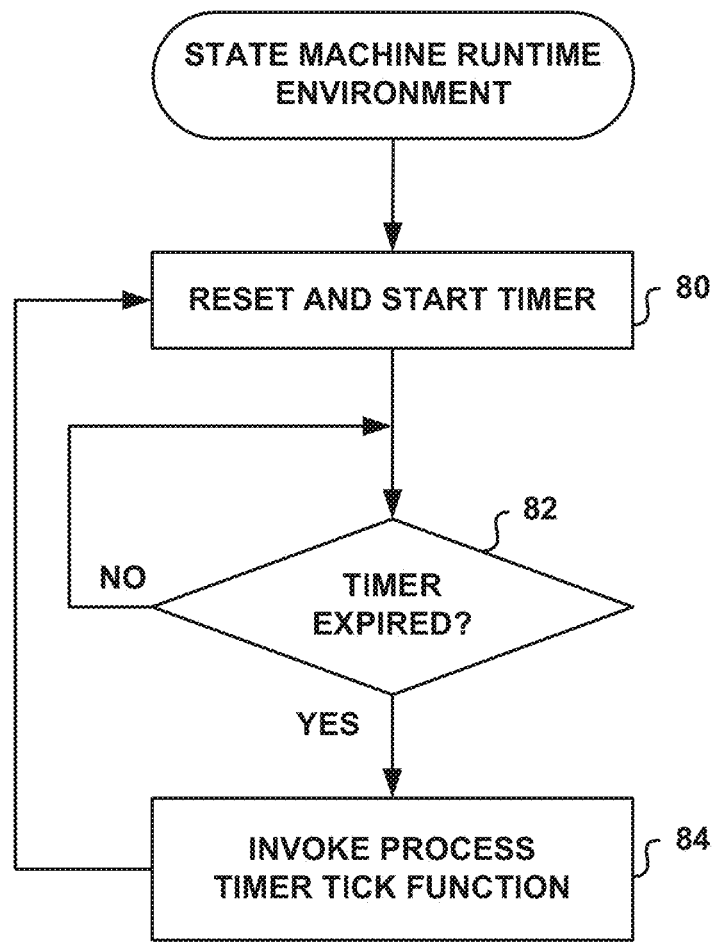
FIG. 7 is a flow diagram illustrating an example top-level process for an example state machine runtime environment according to this disclosure.
Figure 8:
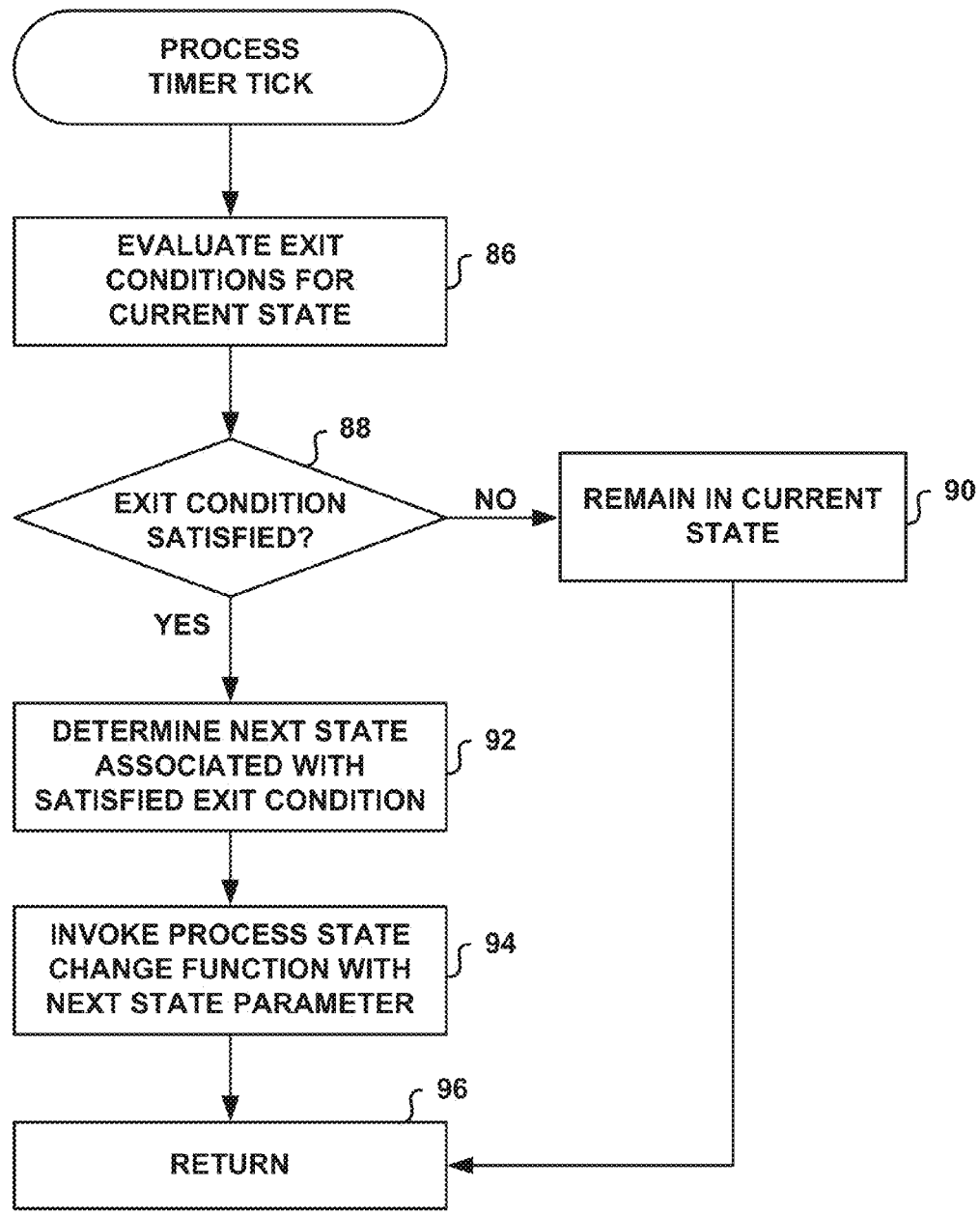
FIG. 8 is a flow diagram illustrating an example process timer tick function according to this disclosure.
Figure 9:
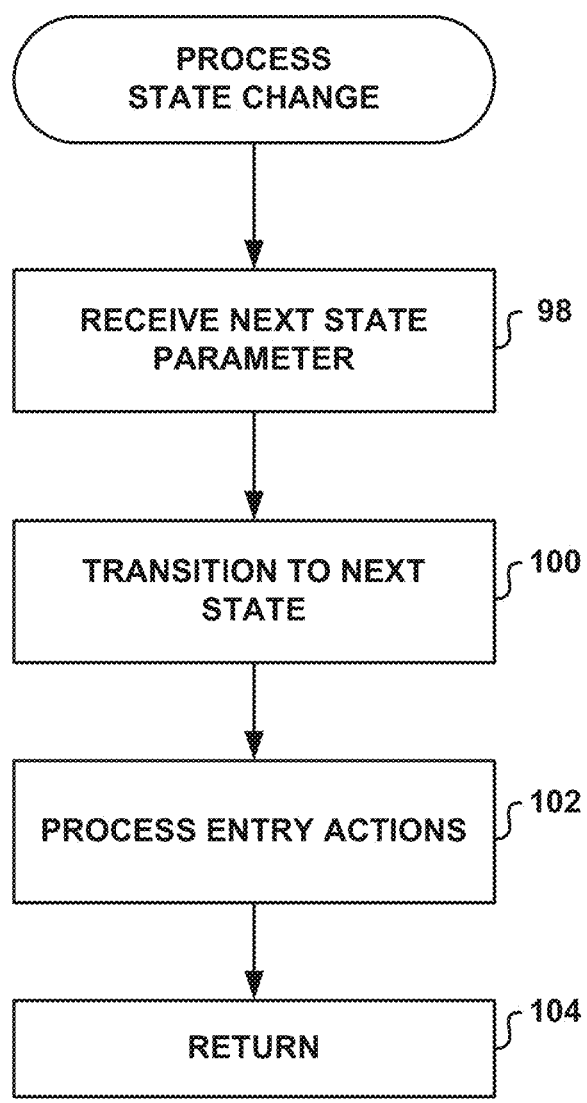
FIG. 9 is a flow diagram illustrating an example process state change function according to this disclosure.

FIGS. 7-9 are flow diagrams illustrating another example state machine runtime environment according to this disclosure. In some examples, the example state machine runtime environment shown in FIGS. 7-9 may be used to implement the example state machine runtime environment illustrated in FIG. 6. The techniques shown in FIGS. 7-9 provide a modular framework for implementing a state machine runtime environment that uses callable functions to evaluate exit conditions and perform entry actions.

The state machine runtime environment shown in FIGS. 7-9 may, in some examples, be embodied in firmware that is stored in IMD 16 (e.g., memory 34) and executed on IMD 16 (e.g., processor 32). In further examples, the state machine runtime environment may be hardware implemented, or any combination of hardware, software, and/or firmware.

FIG. 7 is a flow diagram illustrating an example top-level process for an example state machine runtime environment according to this disclosure. In response to invoking execution of the state machine runtime environment, IMD 16 resets and starts a timer (80). IMD 16 determines whether the timer has expired (82). If the timer has not expired, IMD 16 repeats decision box 82 until the timer has expired. In response to the timer expiring, IMD 16 may invoke a process timer tick function (84), which is described in FIG. 8. The process timer tick function may be configured to evaluate exit conditions for a current state and cause a transition to a new state in the event that one of the exit conditions is satisfied. After invoking the process timer tick function, IMD 16 returns to process box 80 to begin a new processing cycle.

FIG. 8 is a flow diagram illustrating an example process timer tick function according to this disclosure. In some examples, the process timer tick function may be invoked as part of the example top-level process shown in FIG. 7.

IMD 16 evaluates the exit conditions for the current state (86). The exit conditions for the current state may be specified by one or more programmable state parameters received from an external device (e.g., programmer 22). IMD 16 determines if at least one of the exit conditions is satisfied (88). If no exit condition is satisfied, IMD 16 remains in the current state (90)

and proceeds to process box 96, which returns processing to the top-level process for the state machine runtime environment.

If at least one exit condition is satisfied, then IMD 16 may determine a next state associated with the satisfied exit condition (92). In some examples, multiple exit conditions for a single state may be satisfied during the same processing cycle. In such examples, IMD 16 may select the exit condition with the highest priority, and determine the next state based on the selected exit condition as discussed above with respect to process box 76 of FIG. 6.

IMD 16 invokes a process state change function with the next state determined in process box 92 as an input parameter (94). The process state change function is described in FIG. 9. The process state change function may be configured to transition to a next state and perform the entry actions associated with the next state. IMD 16 returns processing to the top-level process for the state machine runtime environment (96).

FIG. 9 is a flow diagram illustrating an example process state change function according to this disclosure. In some examples, the process state change function may be invoked as part of the example process timer tick function shown in FIG. 8.

IMD 16 receives a next state parameter (98). The next state parameter may be a parameter indicative of a next state of the state machine to process. IMD 16 transitions to the next state specified by the next state parameter (100). Transitioning to the next state may include updating a current state variable and/or a current state register.

IMD 16 processes the entry actions associated with the next state (102). The entry actions may be specified by one or more programmable state parameters received from an external device (e.g., programmer 22). Processing the entry actions may include performing the entry actions. IMD 16 returns processing to the process timer tick function (104).

In an embedded closed loop system the signal sampling and classifier firmware may typically operate on regular timing intervals. At a selected interval when the classifier firmware outputs are valid, state processing may be invoked by calling the "ProcessTimerTick" function. A call to this function may cause the exit conditions of the current state to be evaluated from highest priority to lowest priority (including a possible state timer expiration) to see if any classifier conditions that are not marked as don't cares are met. The first evaluated exit condition to be satisfied may cause a state transition to the assigned next state. It should be noted that when none of the conditional exit directives for a state are satisfied, the current state may remain unchanged.

When the "ProcessTimerTick" function has determined to transition to a new state the "ProcessTimerTick" function may call the "ProcessStateChange" function with the next state specified for the exit condition as a parameter. The "ProcessStateChange" function may perform the switching to the new state and process the stimulation control policies of the new state.

The entry actions for the new state and their associated parameters may include one or more of the following: a stimulation program parameter, a stimulation control parameter, an increment/decrement stimulation flags parameter, and a timer count parameter. The stimulation program parameter may specify whether the stimulation program is switched to a specified program or kept the same. The stimulation control parameter may specify an action that is to be performed with respect to the delivery of stimulation (e.g., ON, OFF or leave unchanged). The increment/decrement stimulation flags parameter may be used to set either an increment (INC) flag or a decrement (DEC) flag (or none) to be processed by another state that turns stimulation on. The timer count parameter may be loaded into the state timer. If the timer count parameter is set to 0, then the timer may be disabled (e.g., there may be no timeout from the state and the state will not transition until one of the other conditions is satisfied).

For the increment/decrement stimulation flags parameter, if stimulation is turned ON, an adjustment to the stimulation may be made immediately in response to entering a new state. If stimulation is turned OFF, then a global flag may be set (e.g., a global Increment flag or a global Decrement flag) indicating that the next time stimulation is turned ON with the same stimulation program in a subsequent processing cycle, the stimulation amplitude may either be incremented or decremented from the previous "stimulation on" value (i.e., the amplitude that was used when stimulation was previously turned ON).

If turning stimulation ON (and the stimulation program was unchanged from last state in which stimulation was ON), the INC/DEC stimulation global flags, which may have been set by a previous state, may cause the stimulation to be increased/decreased, respectively, in pre-determined voltage steps. In some cases, these flags may be mutually exclusive. Both flags may be cleared after the stimulation is turned on.

Figure 10:
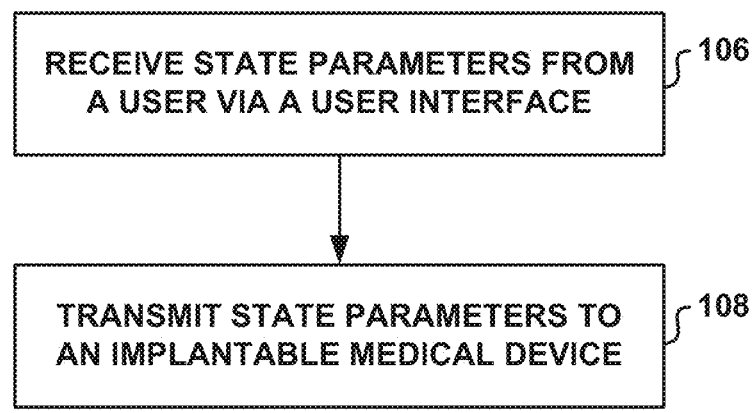
FIG. 10 is a flow diagram illustrating an example technique for programming a programmable state machine that is implemented on an IMD according to this disclosure.

FIG. 10 is a flow diagram illustrating an example technique for programming a programmable state machine that is implemented on an IMD according to this disclosure. In some examples, the example technique shown in FIG. 10 may be implemented on a device that is external to an IMD, but communicatively coupled to the IMD. For example, the example technique in FIG. 11 may be implemented on programmer 22 shown in FIGS. 1 and 3, which is communicatively coupled to IMD 16 via telemetry.

Programmer 22 receives one or more state parameters from a user via a user interface (106). Programmer 22 transmits the received state parameters to IMD 16 (108). In some examples, the state parameters may be transferred to IMD 16 as a sequence or table of parameter values, and not as part of a set of firmware code.

Figure 11:
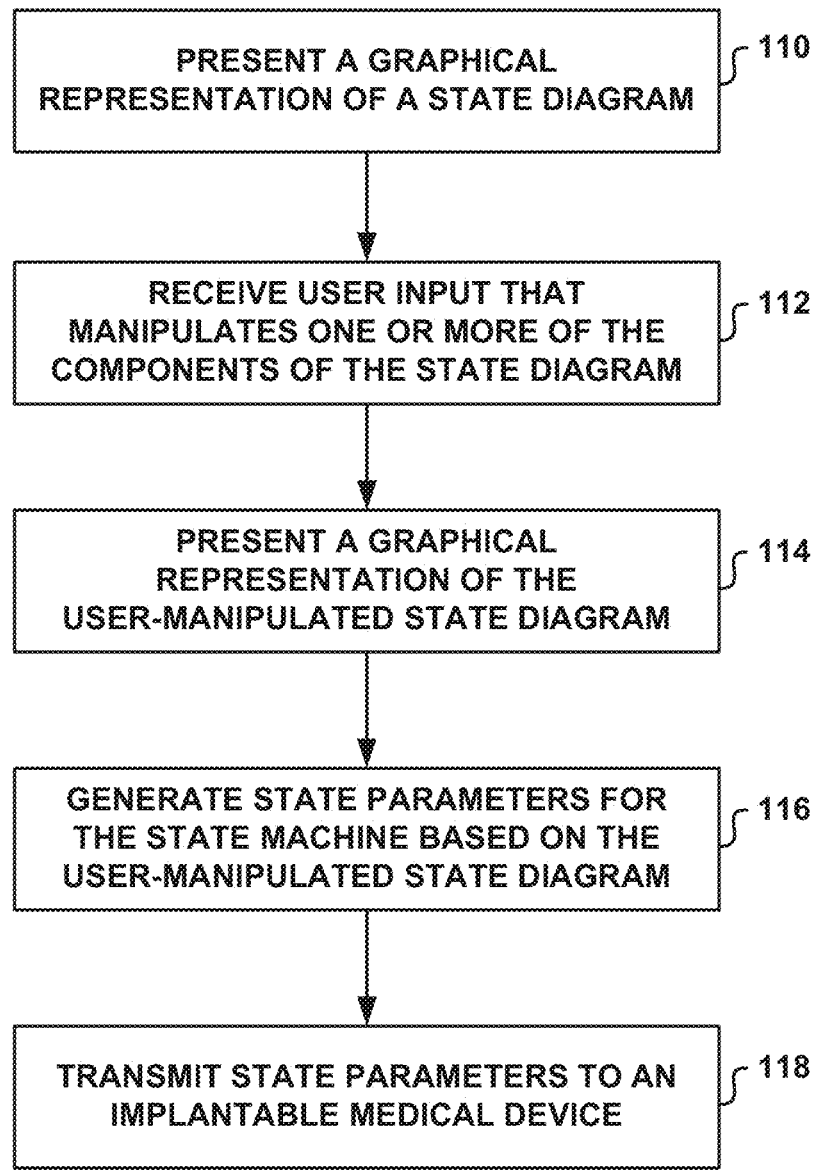
FIG. 11 is a flow diagram illustrating another example technique for programming a programmable state machine that is implemented on an IMD according to this disclosure.

FIG. 11 is a flow diagram illustrating another example technique for programming a programmable state machine that is implemented on an IMD according to this disclosure. In some examples, the example technique shown in FIG. 11 may be implemented on a device that is external to an IMD, but communicatively coupled to the IMD. For example, the example technique in FIG. 11 may be implemented on programmer 22 shown in FIGS. 1 and 3, which is communicatively coupled to IMD 16 via telemetry.

Programmer 22 presents a graphical representation of a state diagram that includes components that are capable of being manipulated by a user (110). The graphical representation may, in some examples, be presented on a display of programmer 22. In some examples, the graphical representation may include one or more state nodes and/or one or more state transition arcs connecting the state nodes.

Programmer 22 receives user input that manipulates one or more of the components of the state diagram to generate a user-manipulated state diagram (112). In some examples, the user input may include user input that drags a state node to a different position on the display, user input that drags a state transition arc to a different position on the display, user input that connects the beginning or end of a state transition arc to respective ones of the state nodes, and/or user input that selects a state node for further editing. In some examples, in response to selecting a state node for further editing, programmer 22 may cause a state framework dialog box to appear on the display to allow the user to program various state parameters associated with that state. The user-manipulated state diagram may include any changes that are caused by the user input.

Programmer 22 presents a graphical representation of the user-manipulated state diagram (114). The graphical representation may, in some examples, be presented on a display of programmer 22. In this way, programmer 22 may, in some examples, provide a user interface that allows a user to interactively build, manipulate, and program state machines.

Programmer 22 generates the state parameters for the state machine based on the user-manipulated state diagram (116). Programmer 22 transmits the received state parameters to IMD 16 (118). In some examples, the state parameters may be transferred to IMD 16 as a sequence or table of parameter values, and not as part of a set of firmware code. In this way, programmer 22 may allow a user to program and/or change a control policy algorithm that is implemented on IMD 16 without requiring new firmware code to be downloaded to IMD 16.

Figure 12:
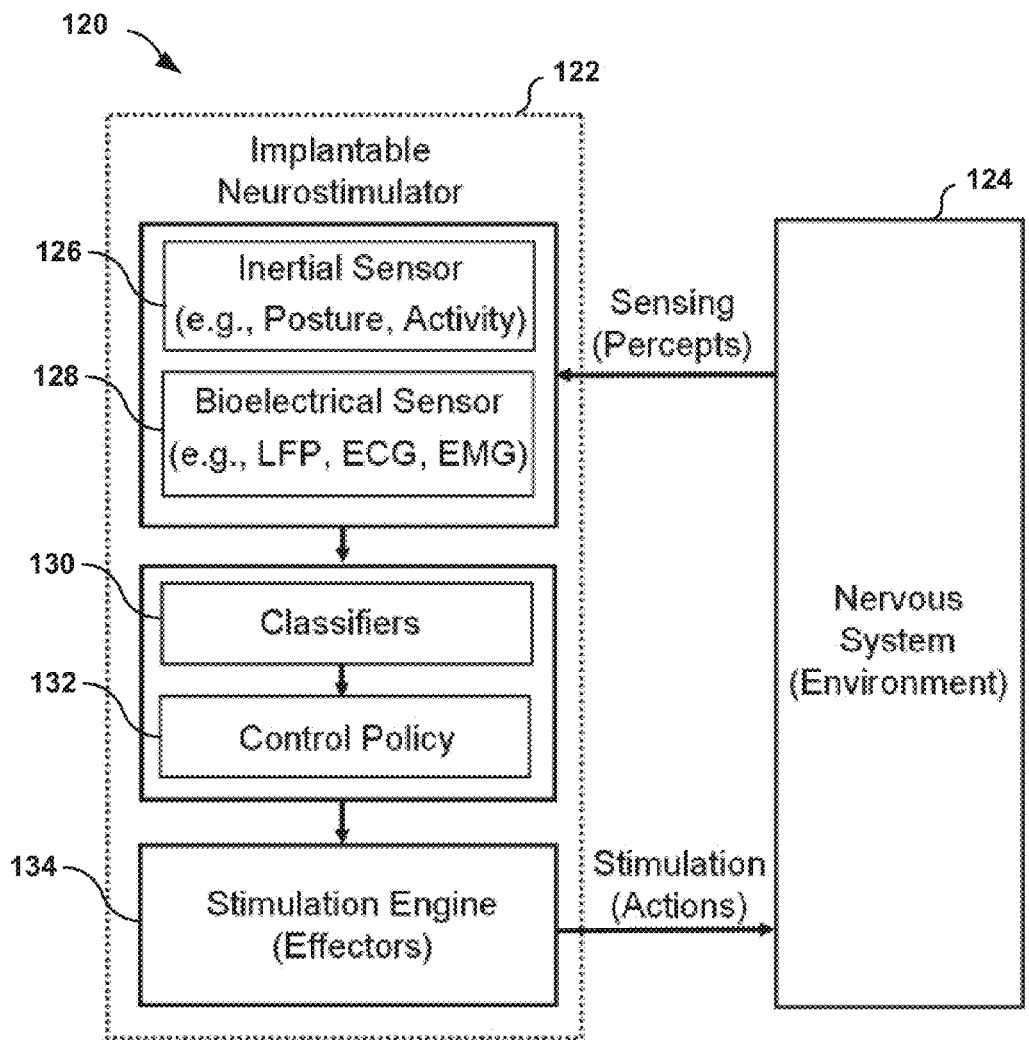
FIG. 12 is a conceptual diagram illustrating a model of a closed-loop neuromodulation system.

FIG. 12 is a conceptual diagram illustrating a model of a closed-loop neuromodulation system 120. Neuromodulation system 120 includes an implantable neurostimulator 122 and nervous system 124. Implantable neurostimulator 122 includes an inertial sensor 126, a bioelectrical sensor 128, classifiers 130, a control policy 132, and a stimulation engine 134. Inertial sensor 126 and bioelectrical sensor 128 may each represent one or more of their respective kind of sensor.

In some examples, nervous system 124 may correspond to patient 14 shown in FIG. 1, and implantable neurostimulator 122 may correspond to IMD 16 shown in FIG. 1. In further examples, inertial sensor 126 may correspond to sensors 40 shown in FIG. 2, bioelectrical sensor 128 may correspond to electrical sensing module 38 shown in FIG. 2, and stimulation engine 134 may correspond to stimulation generator 36 shown in FIG. 2. In additional examples, classifiers 130 and control policy 132 may correspond to processes that are executed by processor 32 of IMD 16. In some examples, the program code for classifiers 130 and/or control policy 132 may be stored as firmware code in a memory (e.g., memory 34 of FIG. 2).

As shown in FIG. 12, spectral features may be extracted from bioelectrical sensor 128 and piped into classifiers 130. In some cases, classifiers 130 may be trained using machine learning techniques. Posture and activity features may be extracted from inertial sensor 126. The outputs of classifiers 130 may be the inputs to control policy 132 which controls stimulation engine 134.

Inertial sensor 126 and bioelectrical sensor 128 may sense various states of nervous system 124, and stimulation engine 134 may deliver electrical stimulation in response to the sensed states of nervous system 124. In general, the sensing may correspond to percepts, the stimulation may correspond to actions, stimulation engine 134 may correspond to effectors, and nervous system 124 may correspond to the environment.

Inertial sensor 126 and bioelectrical sensor 128 within implantable neurostimulator 122 may obtain signals from nervous system 124 directly or indirectly. As shown in FIG. 12, inertial sensor 126 may be used to identify patient posture, patient activity, a tremor, etc. Bioelectrical sensor 128 may include an LFP sensor, an ECG sensor, an EMG sensor, etc. Local field potentials (LFPs) may be an example of a signal measured directly from the brain. Inertial signals may be a more indirect surrogate for brain state.

Also embedded within implantable neurostimulator 122 are algorithms to classify states (e.g., classifiers 130) and to control the stimulation therapy (e.g., control policy 132). Each of classifiers 130 may be configured to detect and/or classify whether nervous system 124 is in a particular state based on data received from inertial sensor 126 and/or bioelectrical sensor 128, and generate data indicative of whether the particular state has been detected for nervous system 124.

Control policy 132 is configured to control the delivery of therapy by stimulation engine 134 of implantable neurostimulator 122 based on the sensed states of nervous system 124 received from classifiers 130. According to this disclosure, control policy 132 may be implemented by a state machine runtime environment that is configurable to implement a state machine based on one or more programmable state parameters that are received from an external device. The one or more state parameters may define at least part of the structure of the state machine. Because the same state machine runtime environment is configurable to implement a variety of different state machines depending on the downloaded state parameters, the same generic, state machine-independent firmware code may be used to implement different state machines. In this way, the control policy algorithm for implantable neurostimulator 122 may be able to be programmed and/or reconfigured by an external device without requiring firmware code to be reloaded onto implantable neurostimulator 122.

Figure 13:
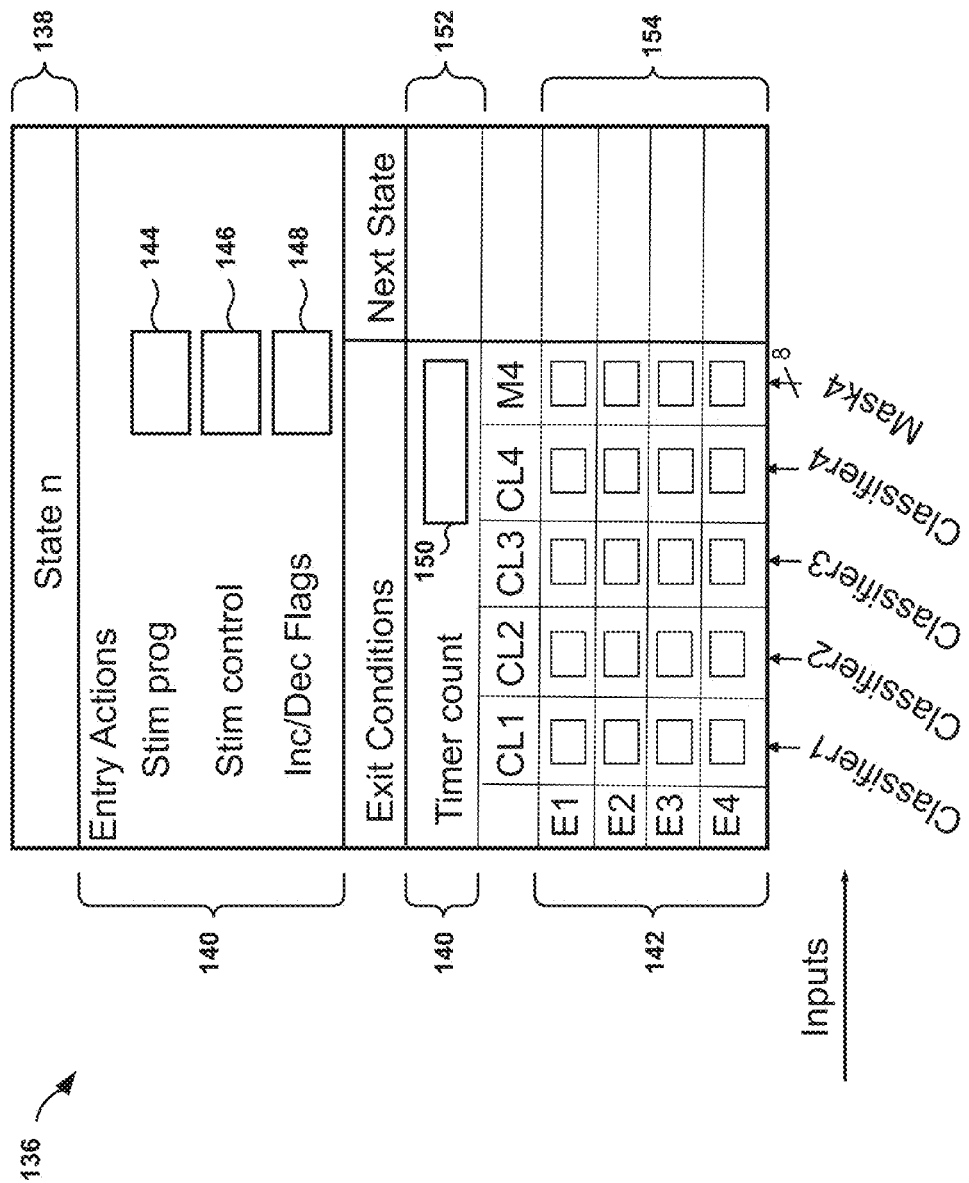
FIG. 13 is a conceptual diagram of an example state framework dialog box template that allows a user to program state parameters associated with a particular state in a state machine according to this disclosure.

FIG. 13 is a conceptual diagram of an example state framework dialog box template 136 that allows a user to program state parameters associated with a particular state in a state machine. For example, state framework dialog box template 136 may enable a user to create a particular state in a state machine that includes entry actions and exit conditions. The entry actions may enable a user to select actions related to the delivery of stimulation therapy. The exit conditions may enable a transition from the current state to another state. A user may use state framework dialog box template 136 to build a control policy algorithm by creating states and connecting them together to form a state machine.

In some examples, the state parameters may contain information on how to control flow order (e.g., make decisions on state transitions based on prioritized classifier input(s)), control stimulation output (e.g., turn stimulation on/off, change stimulation programs, increment/decrement current stimulation values, etc.), and/or control the timing of state execution (e.g., delay transition). Other state parameters are also possible.

State framework dialog box template 136 may correspond to a software graphical user interface (GUI) template representing information that may be "filled in" individually for each state in a state machine. The state associated with each dialog box may be indicated by state identifier 138. Because state framework dialog box template 136 shown in FIG. 13 is a generic template, the state identified by state identifier 138 in FIG. 13 is shown as "State n." In general, n may represent any name for the states within a state diagram. In some cases, the state names may take the form of non-negative integers.

As shown in FIG. 13, state framework dialog box template 136 may include a variety of different fields, each of which may correspond to one or more state parameters. The different fields may generally be subdivided into entry action fields 140 and exit condition fields 142.

Entry action fields 140 may represent entry actions that are to be performed when a state is entered. Entry action fields 140 may enable a user to select actions related to stimulation therapy. For example, entry action fields 140 may be used to program how a control policy algorithm adjusts the delivery of stimulation therapy (e.g., electrical stimulation therapy). In general, when the state machine runtime environment enters a state from another state, the state machine runtime environment may execute the entry actions for the entered state. Entry action fields 140 include a stimulation program field 144, a stimulation control field 146, an increment/decrement flag field 148, and a timer count field 150.

Stimulation program field 144 is configured to receive a state parameter that defines one or more stimulation program entry actions for the state identified by state identifier 138. For example, the state parameter received by stimulation program field 144 may be indicative of which stimulation program or stimulation program group is to be used by IMD 16 to control the delivery of therapy when operating in the state identified by state identifier 138 (i.e., State n). Stimulation program field 144 may be used by a control policy algorithm programmer to assign a stimulation program or a stimulation program group to be used when the state identified by state identifier 138 (i.e., State n) activates.

In some examples, the state parameter indicative of a stimulation program or a stimulation program group may be indicative of whether the stimulation program or stimulation program group is to be changed from or remain the same as the stimulation program or stimulation program group used for the previous state. In other words, in such examples, the data received by stimulation program field 144 may indicate whether a new program should be used for the current state (i.e., whether a program switch is to occur) or whether the previous program should be kept in use.

In some examples, stimulation program field 144 may be configured to receive a selection from a finite set of stimulation programs that are programmed into IMD 16. For example, four different stimulation programs may be preprogrammed into IMD 16, and the state machine framework may allow a user to select one of the four different stimulation programs for each of the states in a state machine. In this example, for stimulation program field 144, a user may be allowed to select from one of the following values: P1, P2, P3, P4, No Change. Each of P1, P2, P3 and P4 may correspond to a stimulation program. No change may indicate that the stimulation program is to remain the same as the stimulation program used for the previous state. In some cases, No Change may be abbreviated as NC. In this example, IMD 16 allows a stimulation program to be optionally switched to any of the four available programs or left as it was.

Each of the different programs may be defined by a respective set of stimulation therapy parameters. The programs may be stored in IMD 16 (e.g., memory 34). For each of the different programs, a separate set of adjustable stimulation therapy parameters may be stored. In general, each of the adjustable stimulation therapy parameters may represent a degree of freedom for the delivery of stimulation therapy.

For a neurostimulator, the stimulation therapy parameters, in some examples, may include the electrode configuration, the amplitude of the stimulation, the pulse width of the stimulation, and/or the frequency of the stimulation. The electrode configuration may include the electrodes (i.e., contacts) used for delivery of therapy and the polarity of the electrodes (e.g., anode or cathode). The electrodes used for the delivery of therapy may include lead-based electrodes and electrodes that are carried or located on a case of the neurostimulator (i.e., a can electrode or a case electrode). In some cases, the amplitude may be adjusted within a set of programmable limits.

Stimulation control field 146 is configured to receive a state parameter that defines one or more stimulation control entry actions for the state identified by state identifier 138. In some cases, the state parameter received by stimulation control field 146 may be indicative of any changes to the stimulation state when entering the state identified by state identifier 138. For example, the state parameter received by stimulation control field 146 may indicate whether stimulation is to be turned on (i.e., activated), whether stimulation is to be turned off (i.e., deactivated), or whether the stimulation state is to remain unchanged when transitioning to the state identified by state identifier 138. In one example, for stimulation control field 146, a user may be allowed to select from one of the following values: ON, OFF and No Change. In some cases, No Change may be abbreviated as NC.

Increment/decrement flag field 148 is configured to receive one or more state parameters that define one or more increment and/or decrement stimulation amplitude entry actions for the state identified by state identifier 138. For example, the state parameters received by increment/decrement flag field 148 may be indicative of whether one or more stimulation amplitudes are to be increased, decreased, or remain the same relative to the previous stimulation amplitudes the next time the stimulation program is turned on or activated. In other examples, one or more fields may be provided to allow stimulation pulse width and/or stimulation frequency to be adjusted in addition to or in lieu of stimulation frequency. In some examples, the state parameters received by increment/decrement flag field 148 may take the form of increment and decrement flags, where each flag indicates whether the stimulation amplitude for a respective one of a plurality of electrodes it to be incremented, decremented, or remain unchanged relative the previous amplitude for the respective one of the plurality of electrodes. In one example, for increment/decrement flag field 148, a user may be allowed to select from one of the following values: set Increment flag, set Decrement flag, and No Change. In some cases, set Increment flag may be abbreviated as Inc, set Decrement flag may be abbreviated as Dec, and No Change may be abbreviated as NC.

Increment/decrement flag field 148 may enable the stimulation amplitude to be incremented or decremented based on the state of the state machine in which IMD 16 is currently operating. If stimulation control field 146 indicates that stimulation is ON, an adjustment may be made immediately in response to entering the state identified by state identifier 138. If stimulation control field 146 indicates that the stimulation is OFF, then a global flag may be set (either a global Increment flag or a global Decrement flag) indicating that the next time stimulation is turned ON without a change of program in a subsequent processing cycle, the stimulation amplitude may either be incremented or decremented from the previous "stimulation on" value (i.e., the amplitude that was used when stimulation was previously turned ON).

In some cases, when stimulation control field 146 indicates that stimulation is turned ON and stimulation program field 144 indicates that the stimulation program is unchanged, the Increment/Decrement flags in increment/decrement flag field 148 may be checked and the amplitude of stimulation may be adjusted based on the Increment/Decrement flags specified in increment/decrement flag field 148. After the Increment/Decrement flags have been adjusted, the Increment/Decrement flags may be cleared.

Timer count field 150 is configured to receive a state parameter that defines a timeout entry action for the state identified by state identifier 138. For example, the state parameter received by timer count field 150 may be indicative of whether a state timeout timer is to be set upon entry for the state identified by state identifier 138 and, if the state timeout timer is to be set, the timer value to be used for setting the state timeout timer. The timer value may indicate the amount of time that the state machine execution runtime may wait prior to triggering a state timeout condition. An expiring state timeout timer (e.g., a state timeout condition) may cause a transition to a new state if none of the other exit conditions have been met when the state timeout timer has expired. Timeout next state field 152 specifies the next state to which the state machine will transition upon expiration of the state timeout timer.

Timeout next state field 152 is configured to receive a state parameter indicative of a next state to which the state machine will transition in response to a state timeout condition. A state timeout condition may occur, for example, when the state timeout timer that is specified in timer count field 150 has expired. Timeout next state field 152 may specify any state in the state machine.

In some cases, setting the state timeout timer to a particular value may be considered an entry action for the particular state, and evaluating the state timeout timer to see if the timer has expired (e.g., to determine whether a state timeout condition has occurred) may be considered an exit condition for the particular state. The next state associated with the state timeout field may be associated with the exit condition.

In some examples, the state timeout feature may be an optional feature. In such examples, if the user enters a timer value in timer count field 150, the state timeout timer is activated and causes an exit from the state upon its expiration. On the other hand, if no timer value is entered in timer count field 150, then the state timeout timer is not active and the state will not be exited via the timer. Instead, other exit conditions will be used to exit from the state.

In some examples, the time values received by timer count field 150 may be in units of seconds. In further examples, the "tick rate" of the state timeout timer may be determined based on the update and/or query rate of the classifiers (e.g., classifiers 130). For example, the classifier may be updated and queried every 200 milliseconds (ms). In such examples, 200 ms may be used as the "tick rate" of the state timeout timer.

When a state machine runtime environment is executing on IMD 16, in response to transitioning to a new state, the state machine runtime environment may process the entry actions associated with the new state. The entry actions may be specified by programmable state parameters. Processing the entry actions may include performing the entry actions specified by the state parameters. For example, IMD 16 may switch or maintain the program used for the delivery of stimulation therapy by IMD 16 in response to processing a stimulation program entry action. As another example, IMD 16 may activate, deactivate, or maintain the current activation status of a stimulation program in response to processing a stimulation control entry action. As a further example, IMD 16 may increment, decrement, or maintain the previous stimulation amplitude in response to processing an increment and/or decrement stimulation amplitude entry action. As another example, IMD 16 may set a state timeout timer to a particular value and start the timer in response to processing a timeout entry action.

Exit condition fields 142 are configured to receive state parameters that represent exit conditions which are evaluated while operating in the state specified by state identifier 138. The exit conditions may be used to determine when a state transition may occur. Exit condition next state fields 154 may be used to determine to which state the state machine will transition for each of the exit conditions.

Exit condition fields 142 are configured to receive state parameters indicative of one or more exit conditions for the state identified by state identifier 138. Exit condition next state fields 154 are configured to receive state parameters indicative of the next state associated with one or more exit conditions for the state identified by state identifier 138. Each of the rows in exit condition fields 142 and exit condition next state fields 154 represents a particular exit condition. An exit condition for a particular row may be defined by the values entered into the exit condition fields 142 for that particular row and the next state value entered into exit condition next state fields 154 for that particular row. Exit condition fields 142 may be alternatively referred to as conditional state exit directives.

Each of the exit conditions may have a priority. In the example state framework dialog box template 136 of FIG. 13, the exit conditions are prioritized from top-to-bottom. That is, the priority is determined by the ordering of exit conditions with priority descending from the first exit condition (P1) to the last exit condition (P4). For example, the P1 exit condition has a priority that is higher than the P2 exit condition, which has a priority that is higher than the P3 exit condition, which has a priority that is higher than P4 exit condition. When evaluating the exit conditions, if multiple exit conditions are satisfied, IMD 16 may select the satisfied exit condition with the highest priority to use for determining the next state.

Each of the columns in exit condition fields 142 represents a different input variable or set of input variables that are received by the state machine. For example, the first column in exit condition fields 142 represents an input variable to the state machine that is received from Classifier1, the second column in exit condition fields 142 represents an input variable to the state machine that is received from Classifier2, and the third column in exit condition fields 142 represents an input variable to the state machine that is received from Classifier3.

In the example state framework dialog box template 136 of FIG. 13, Classifiers1-3 (i.e., CL1, CL2, CL3) are dual state classifiers meaning that their values may be either 1 or 0 depending on whether a particular state of a patient has been detected and/or classified. In some examples, a dual state classifier may generate a value of 1 in response to sensing, detecting, and/or classifying a particular state for a patient, and generate a value of 0 in response to not sensing, not detecting, and/or not classifying the particular state for the patient. In other examples, the logic levels of the signal may be reversed such that a value of 0 represents sensing, detecting, and/or classifying a particular state of a patient. In further examples, the inputs received from the classifiers may not necessarily be limited to binary values, but may take on other values.

The exit condition fields 142 that are associated with the dual state classifiers (i.e., CL1, CL2, CL3) are each configured to receive a value of 0 (i.e., false), 1 (i.e., true) or X (don't care). The value entered into an exit condition term field that is associated with a dual state classifier may be indicative of whether the output of a classifier associated with the exit condition term field is to be used when evaluating the exit condition. The value entered into the exit condition term field may also be indicative of what output value of the classifier associated with the exit condition term field is needed to satisfy the exit condition associated with the exit condition term field.

For example, a value of X that is entered into one of exit condition fields 142 may indicate that the output of the classifier associated with the exit condition term field is not to be used for evaluating the exit condition associated with the exit condition term field. A value of 1 entered into the exit condition term field may indicate that the output value of the classifier associated with the exit condition term field needs to be equal to a 1 in order for the exit condition associated with the exit condition term field to be satisfied. Similarly, a value of 0 entered into the exit condition term field may indicate that the output value of the classifier associated with the exit condition term field needs to be equal to a 0 in order for the exit condition associated with the exit condition term field to be satisfied.

In the example state framework dialog box template 136 of FIG. 13, Classifier4 is a multi-state classifier meaning that the classifier has greater than two output values. Each set of output values may correspond to a sensed state of the patient. In some examples, Classifier4 has an output range of 2 values to 8 output values. An example of a multi-state classifier is a posture classifier where the posture classifier may have multiple discrete output states (e.g., Upright, Lying down stomach, Lying down back, etc.).

The exit condition fields 142 that are associated with dual state classifier CL4 include the exit condition fields 142 in the CL4 column and the exit condition fields 142 in the M4 column (i.e., mask column). The exit condition fields 142 in the CL4 column are each configured to receive a value of 1 (i.e., true), 0 (i.e., false) or X (don't care). The exit condition fields 142 in the M4 column are each configured to receive a bit mask where each bit in the bit mask is assigned to one of the possible output values for Classifier4. Each bit in the bit mask may take on a value of 0 or 1. The bit mask may specify which classifier outputs are relevant for evaluating the exit condition. For example, if a bit in the bit mask is set to 1, then the classifier output value associated with that bit may be evaluated when evaluating the exit condition associated with the bit mask. As another example, if a bit in the bit mask is set to 0, then the classifier output value associated with that bit may not be evaluated when evaluating the exit condition associated with the bit mask. The combination of classifier output values for which the mask values are equal to 1 may be referred to as the masked output states for the particular row in exit condition fields 142.

Setting one of the exit condition fields 142 for a particular row in the CL4 column to a value of 1 causes the state machine execution environment to look for cases where all of the masked output states for that particular row are equal to 1 (i.e., True). On the contrary, setting one of the exit condition fields 142 for the particular row in the CL4 column to a value of 0 causes the state machine execution environment to look for cases where all of the masked output states for that particular row are equal to 0 (i.e., False). Using this type of format makes it possible to transition to a different state on a condition where one or more states are valid (with either all '1's or '0's).

Exit condition next state fields 154 are configured to receive values indicative of the next state to transition to for each of the exit conditions. The value entered into exit condition next state fields 154 may, in some examples, correspond to any state in the state machine. In further examples, the current state may be excluded from the set of allowable values that may be entered into exit condition next state fields 154. When the state of the classifiers matches a row in exit condition fields 142, the state machine execution runtime may exit the current state and transition to the corresponding next state specified by exit condition next state fields 154. Each of exit condition next state fields 154 is included in a particular row of exit condition fields 142 and determines the next state associated with the exit condition for that particular row. In some examples, if a row (i.e., exit condition) has values entered into exit condition fields 142, then a next state may be specified by the exit condition next state field 156 that is included in that row. On the other hand, if a row (i.e., exit condition) does not have values entered into exit condition fields 142, then a next state need not be specified by the exit condition next state field 156 that is included in that row.

In general, the values entered into exit condition fields 142 for a particular row may specify a combination of classifier values that are needed to satisfy the exit condition corresponding to that particular row. For example, if in row P1, the CL1 box is set to a value of 1, the CL2 box is set to a value of 0, and the CL3 and CL4 boxes are set to a value of X, this means that, in order to satisfy the P1 exit condition, CL1 must generate a value of 1 and CL2 must generate a value of 0 during the processing cycle for the state. The X indicates that it does not matter what the values of CL3 and CL4 are to satisfy the exit condition.

When a state machine runtime environment is executing on IMD 16, while operating in a particular state, IMD 16 may periodically or continuously evaluate the exit conditions associated with the particular state. To evaluate the exit conditions, IMD 16 may determine whether the inputs to the state machine (i.e., the outputs of the classifiers) match any of the exit conditions for the state machine. The exit conditions may be specified by one or more programmable state parameters, which in some examples, may be specified by exit condition fields 142 of one or more state framework dialog boxes similar to state framework dialog box template 136. If IMD 16 determines that an exit condition is satisfied, IMD 16 may transition to the next state associated with the exit condition. The next state associated with each of the exit conditions may be specified by one or more programmable state parameters, which in some examples, may be specified by exit condition next state fields 154 of one or more state framework dialog boxes similar to state framework dialog box template 136.

If multiple exit conditions are satisfied during the same processing cycle, IMD 16 may select the exit condition with the highest priority as the exit condition from which the next state may be determined. In the example state framework dialog box template 136 of FIG. 13, the exit conditions decrease from priority from top-to-bottom. Thus, if multiple exit conditions are satisfied during the same processing cycle, then state framework dialog box template 136 may select the top-most exit condition that is satisfied for further processing.

As shown in FIG. 13, the classifiers (CL1-CL4) can be used to initiate a state transition. The example state framework dialog box template 136 of FIG. 13 allows 4 combinations of classifier exit conditions (Rows P1-P4) to be checked in order, starting with P1, to determine if the state should change. However, other examples may have more rows or fewer rows that are checked in a different order, the same order, or a random order. Each row contains options for each of the classifiers.

In FIG. 13, entry action fields 140 may specify one or more entry actions for the state identified by state identifier 138. Entry action fields 140 may be configured to receive a user-specified combination of one or more entry actions via stimulation program field 144, stimulation control field 146, increment/decrement flag field 148 and/or timer count field 150. The entry actions may include an action that selects one of a plurality of stimulation programs to be used for delivery of stimulation (e.g., specified by stimulation program field 144), an action that turns on the delivery of the stimulation (e.g., specified by stimulation control field 146), an action that turns off the delivery of the stimulation (e.g., specified by stimulation control field 146), an action that causes no change to an activation state of the stimulation (e.g., specified by stimulation control field 146), an action that increases or increments an amplitude of the stimulation (e.g., specified by increment/decrement flag field 148), an action that decreases or decrements the amplitude of the stimulation (e.g., specified by increment/decrement flag field 148), and an action that causes a timeout to occur if no exit conditions are satisfied after a specified period of time (e.g., specified by timer count field 150).

Although not shown in the example state framework dialog box template 136 of FIG. 13, other example state framework dialog boxes may include actions that increase or decrease (e.g., increments or decrements) other stimulation parameters in addition to or in lieu of stimulation amplitude. For example, a state framework dialog box may include fields that specify one or more of the following entry actions: an action that increases a pulse width of the stimulation, an action that decreases the pulse width of the stimulation, an action that increases a frequency of the stimulation, and an action that decreases the frequency of the stimulation.

Exit condition fields 142 and exit condition next state fields 154 may be used to specify a state transition function for the state machine. Each row in exit condition fields 142 may specify an exit condition for the state identified by state identifier 138. Each exit condition may include a respective condition portion (e.g., exit condition fields 142) that specifies a condition to be evaluated and a respective next state portion (e.g., exit condition next state fields 154) that specifies to which state the state machine is to transition if the condition specified in the condition portion is satisfied. In some examples, each of the condition portions (e.g., exit condition fields 142) of the exit conditions may specify a user-specified combination of one or more of a plurality of classifier outputs (which serve as CL1-CL4 and Mask4 inputs to the state machine). Each of the classifier outputs may be indicative of whether a respective one of one or more physiological states has been detected for the patient based on data received from one or more physiological sensors.

Figure 14:
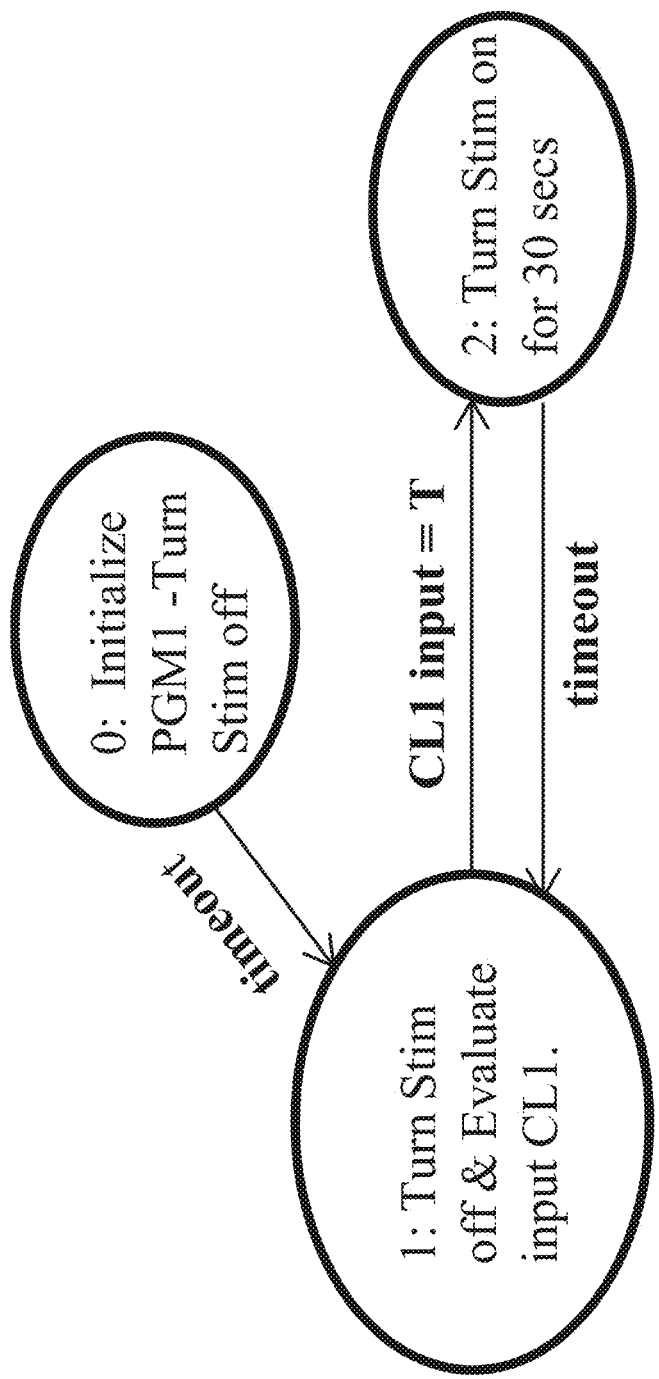
FIG. 14 is a conceptual diagram illustrating a state diagram for an example state machine that may be implemented by using the state machine framework of this disclosure.

FIG. 14 is a conceptual diagram illustrating a state diagram for an example state machine that may be implemented by using the state machine framework of this disclosure. The state machine shown in FIG. 14 depicts a 3-state closed loop algorithm that generates therapy decisions based on an input indicative of a classified state of a patient (i.e., CL1).

As shown in FIG. 14, the state diagram includes three state nodes that are labeled 0, 1, and 2. Each of the state nodes represents a state in the state machine. The corresponding states in the state machine will be referred to in this description by their numbers (i.e., State 0, State 1, and State 2, respectively).

Each of the state nodes in the state diagram specifies one or more operations that may be performed when operating in the state. The state node for State 0 specifies an "Initialize PGM1—Turn Stim off" operation that directs IMD 16 to set up a first stimulation program, and to turn off the delivery of stimulation. The state node for State 1 specifies a "Turn Stim off & Evaluate input CL1" operation that directs IMD 16 to turn off the delivery of stimulation and evaluate the input received from a first classifier. The state node for State 2 specifies a "Turn Stim on for 30 secs" action that directs IMD 16 to turn on the delivery of stimulation for 30 seconds. Each of the actions specified in the state diagram may map to one or more entry actions in the state machine framework.

The state diagram illustrated in FIG. 14 also includes three state transition arcs. A first state transition arc begins at the state node for State 0 and ends at the state node for State 1 and specifies a transition condition of "timeout." A second state transition arc begins at the state node for State 1 and ends at the state node for State 2 and specifies a transition condition of "CL1 input=T." A third state transition arc begins at the state node for State 2 and ends at the state node for State 1 and specifies a transition condition of "timeout." A state transition condition of "timeout" may indicate that the state transition occurs after a timeout timer has expired. A state transition condition of "CL1 input=T" indicates that the state transition occurs when the input received from the first classifier is true (i.e., the first classifier has detected, sensed, and/or classified a state for patient 14). Each of the state transitions and state transition conditions specified in the state diagram may map to one or more exit conditions in the state machine framework.

FIGS. 15-17 are conceptual diagrams illustrating example state framework dialog boxes in which state parameters have been entered for the state diagram illustrated in FIG. 14. The entering of the state parameters may be used to program and/or initialize the state machine implemented by the state machine framework of this disclosure. The format of the state framework dialog boxes is substantially similar to state framework dialog box template 136 shown in FIG. 13. Accordingly, for the sake of brevity and to avoid redundancy, the fields in the dialog boxes will not be described in further detail.

FIG. 15 illustrates an example state framework dialog box in which state parameters have been entered for State 0 of the state diagram illustrated in FIG. 14. For State 0, the stimulation program field is set to "Prgm1," which corresponds to a first stimulation program. The Prgm1 stimulation program may be a default program for this state machine. The stimulation control field is set to "Stim Off," which ensures that the delivery of stimulation is turned off. The timer count field is set to one tick, which activates the timer and causes a timeout condition to occur after a single tick. One tick may correspond to a uniform increment of time (e.g., 200 milliseconds (ms)). In some cases, a tick may be a multiple of the IMD processor clock resolution and/or a multiple of the time between sensing samples. The timeout next state field is set to "State 1" to indicate that in response to a timeout condition, the state machine may transition to State 1. The remainder of the exit condition fields are all set to "X," indicating that the other classifiers are "don't care" (i.e., the other classifiers are not considered when evaluating exit conditions).

State 0 may be the first state executed when the closed loop algorithm is started. The state machine may exit State 0 after 1 timer tick and transition to State 1.

FIG. 16 illustrates an example state framework dialog box in which state parameters have been entered for State 1 of the state diagram illustrated in FIG. 14. For State 1, the stimulation program field is set to "NC," which stands for "No Change" to the stimulation program from that which was used in the previous state. The stimulation control field is set to "Stim Off," which ensures that the delivery of stimulation is turned off. The timer count field is set to zero, which means that the timer is disabled. The Classifier) exit condition term field in the Priority1 exit condition is set to "1" and the next state filed for the Priority1 exit condition is set to "State2." This causes IMD 16 to evaluate the Priority1 exit condition, and when the output of Classifier1 is true (e.g., Classifier1 sensed a particular state of a patient), the state machine will transition to State 2. The remainder of the exit condition fields are all set to "X," indicating that the other exit conditions are not used.

State 1 may turn off the delivery of stimulation upon entry (if stimulation was previously on) and monitor the Classifier1 input condition in response to every timer tick. Note that this state may remain active while Classifier1 is False.

FIG. 17 illustrates an example state framework dialog box in which state parameters have been entered for State 2 of the state diagram illustrated in FIG. 14. For State 2, the stimulation program field is set to "NC," which stands for "No Change" to the stimulation program from that which was used in the previous state. The stimulation control field is set to "Stim On," which enables the delivery of stimulation. The timer count field is set to 30 seconds, which activates the timer and causes a timeout condition after 30 seconds. The timeout next state field is set to "State 1" to indicate that in response to a timeout condition, the state machine may transition to State 1. The remainder of the exit condition fields are all set to "X," indicating that the other classifiers are "don't care" (i.e., the other classifiers are not considered when evaluating exit conditions).

State 2 may turn on the delivery of stimulation with the current stimulation program (i.e., Prgm1) upon entry. This state may remain active (with stimulation turned on) for 30 seconds until the state timer expires. When the timer expires, the state machine may transition to State1.

Note that with the 3-state configuration described in FIGS. 14-17, State 1 may immediately transition back to State 2 if the CL1 classifier input is True. This may result in the stimulation remaining on almost constantly. In some cases, it may be desirable to add a "Delay" state between State 2 and State 1 to prevent the immediate switch back. The state machine framework of this disclosure may facilitate the addition of the "Delay" state with relative ease as discussed below with respect to FIGS. 18-20.

Figure 18:
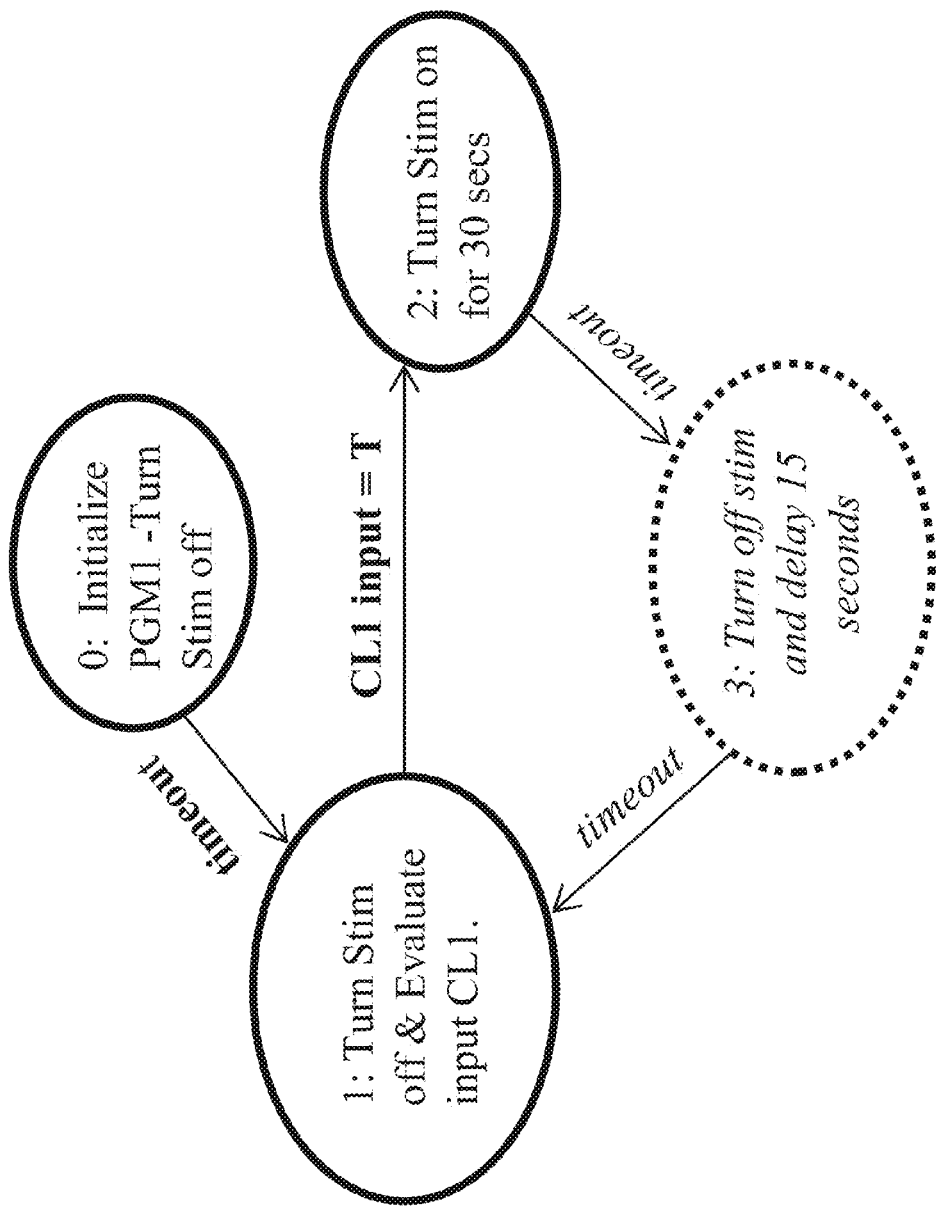
FIG. 18 is a conceptual diagram illustrating a state diagram of an example state machine similar to the example state machine of FIG. 14, but with an additional state added.

FIG. 18 is a conceptual diagram illustrating a state diagram of an example state machine similar to the example state machine of FIG. 14, but with an additional state added. The state diagram shown in FIG. 18 is similar to the state diagram shown in FIG. 14 except that a fourth state has been added and the transition arc from State 2 to State1 has been replaced with a transition arcs from State 2 to State 3 and State 3 to State 1 each of which specifies a transition condition of "timeout." As shown in FIG. 14, the state node for State 3 specifies a "Turn off stim and delay 15 seconds" operation that directs IMD 16 to turn off the delivery of stimulation and wait for 15 seconds prior to transition to the next state.

FIG. 19 is a conceptual diagram illustrating an example state framework dialog box in which state parameters have been entered for State 3 of the state diagram illustrated in FIG. 18. For State 3, the stimulation program field is set to "NC," which stands for "No Change" to the stimulation program from that which was used in the previous state. The stimulation control field is set to "Stim Off," which ensures that the delivery of stimulation is turned off. The timer count field is set to 15 seconds, which activates the timer and causes a timeout condition after 15 seconds. The timeout next state field is set to "State 1" to indicate that in response to a timeout condition, the state machine may transition to State 1. The remainder of the exit condition fields are all set to "X," indicating that the other classifiers are "don't care" (i.e., the other classifiers are not considered when evaluating exit conditions).

State 3 may turn off the delivery of stimulation and transition to State 1 after 15 seconds. In other words, State 3 may delay the transition between State 2 and State 1 to prevent immediate switching from State 2 to State 1.

FIG. 20 is a conceptual diagram illustrating an example state framework dialog box in which state parameters have been entered for State 2 of the state diagram illustrated in FIG. 18. The state parameters shown in FIG. 20 are substantially similar to the parameters shown in FIG. 17 except that the timeout next state field has been set to "State 3" instead of "State 1."

The modified State 2 shown in FIG. 20 may turn on the delivery of stimulation with the current stimulation program (i.e., Prgm1) upon entry. The modified State2 may remain active (with stimulation on) for 30 seconds until the state timer expires. When the timer expires, the state machine may transition to State4.

In some examples, the state machine framework described in this disclosure may receive the state parameter modifications made in FIGS. 19 and 20 from an external device (e.g., programmer 22), and download the modified set of state parameters to IMD 16. A state machine execution runtime environment executing on IMD 16 may modify the state machine implemented by IMD 16. In this way, a "Delay" state may be added to the state machine shown in FIG. 14 to prevent immediate switching between States 2 and 1 without requiring new firmware code to be downloaded to IMD 16.

Figure 21:
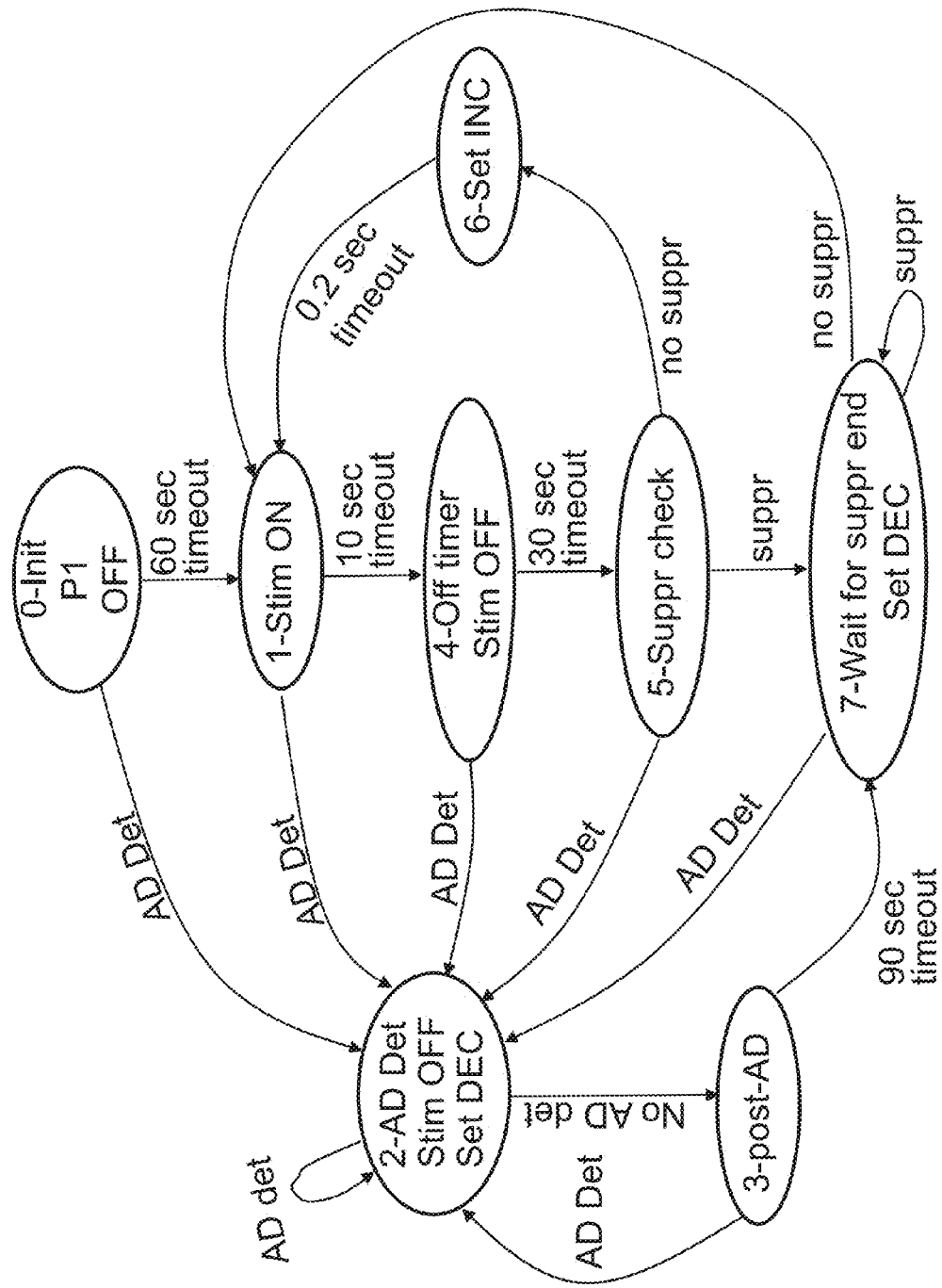
FIG. 21 is a conceptual diagram illustrating a state diagram for an example state machine that performs a homeostasis control policy algorithm and that may be implemented by using the state machine framework of this disclosure.

FIG. 21 is a conceptual diagram illustrating a state diagram for an example state machine that performs a homeostasis control policy algorithm and that may be implemented by using the state machine framework of this disclosure. The homeostasis algorithm may be a control policy algorithm for modulating hippocampal network dynamics.

Two classifiers may be used as inputs to the control policy algorithm. One is an after-discharge (AD) detector, which monitors for seizure-like activity and is valid in the presence of stimulation. In some examples, the AD detector may always cause a state transition, even during events that are timed. The AD detector is designated as CL1 in the following figures.

The second classifier is a suppression detector that monitors for a lower energy level in a selected frequency band, and is designated CL2. Classifiers CL3 and CL4 are not used in this example. Stimulation may be delivered periodically and the amplitude may be adjusted according to the states of the two classifiers and the paths through the state machine.

The homeostasis control policy algorithm initializes the system (state 0) by setting the stimulation program to P1 and turning the stimulator OFF. A 60 second timeout is set before the transition to state 1 (i.e., Stim ON).

When the system transitions to state 1 (i.e., Stim ON), the entry actions corresponding to state 1 are performed. The stimulation program field of the dialog box is set to NC (i.e., "No change"), thereby causing no change to be made to the stimulation program with respect to the stimulation program that was set for the previous state, which is P1. In other words, P1 remains as the active stimulation program. The stimulation control field is set to ON, thereby causing stimulation to be turned ON. A 10 second timeout is set to time the burst of stimulation. If CL1 (AD Det) becomes true during the 10 seconds, a transition is made to state 2. Otherwise the stimulation remains ON for 10 seconds until a transition is made to state 4.

If CL1 (AD Det) becomes true, a transition to state 2 will occur. Upon entry into state 2, stimulation is turned OFF. The decrement (DEC) flag is set so the next burst of stimulation will have a lowered amplitude. The state machine exits state 2 when the detection of AD ends (i.e., CL1 becomes false). State 3 is used to provide at least a 90 second delay before there is any chance of another burst of stimulation.

State 4 turns stimulation OFF and provides a timeout. State 5 checks the output of the suppression detector (CL2) and acts accordingly. State 6 sets the INC flag. This will cause an increase in amplitude during the next state with an ON command. State 6 has an immediate transition to state 1.

In state 7, a DEC flag is used to allow the system to maintain equilibrium. It is possible for the amplitude to be lowered without detection of an after-discharge. State 7 waits for suppression to end before a transition to state 1, which will turn on stimulation.

Figure 22:
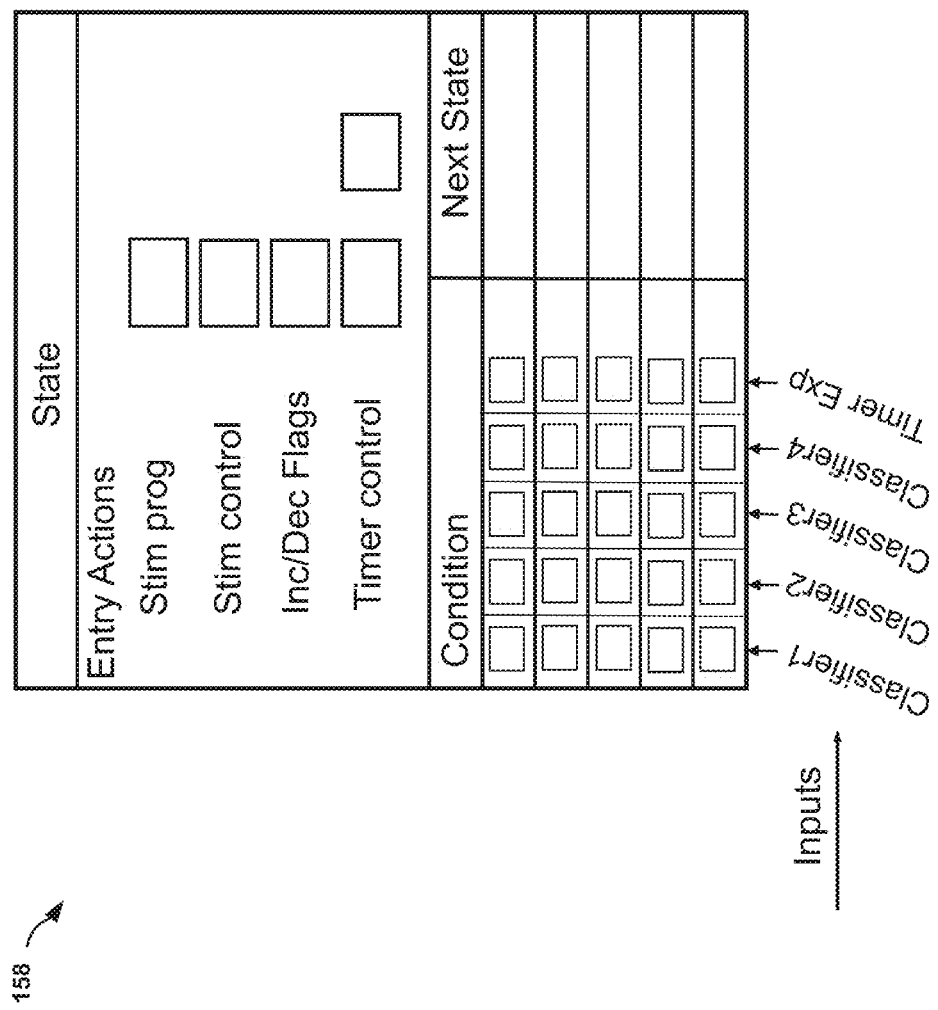
FIG. 22 is a conceptual diagram of an example state framework dialog box template that may be used to implement the homeostasis control policy algorithm shown in FIG. 21.
Figure 23:
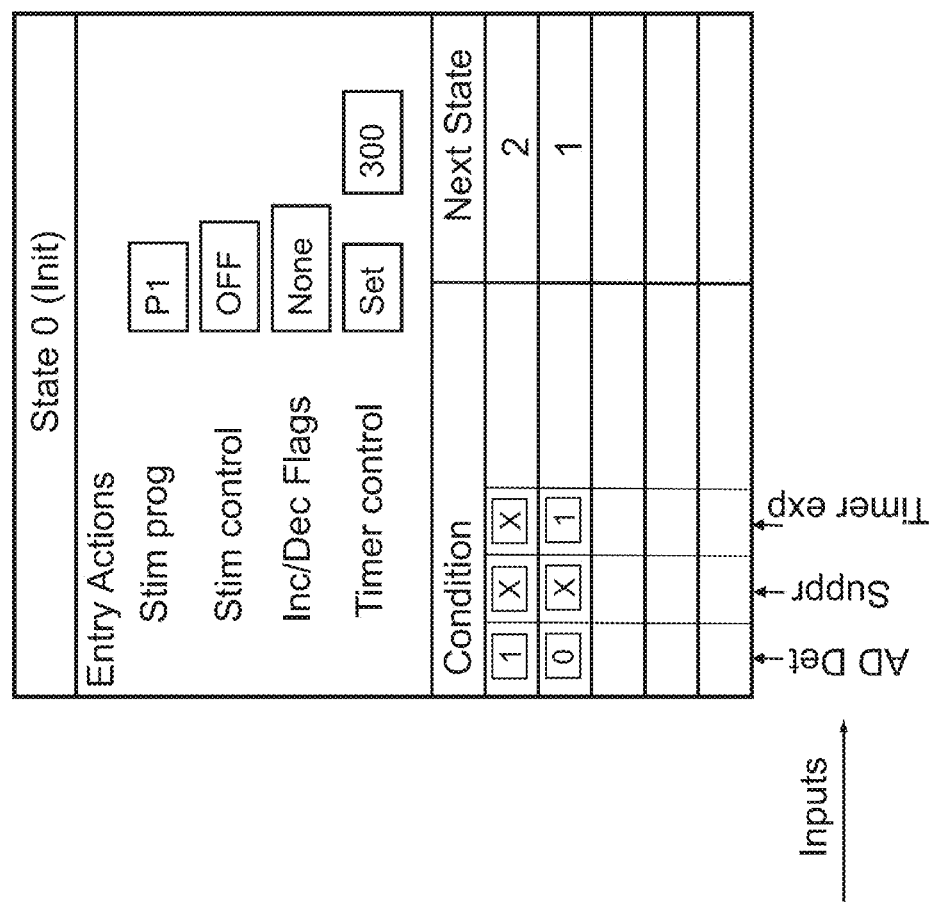
Figure 24:
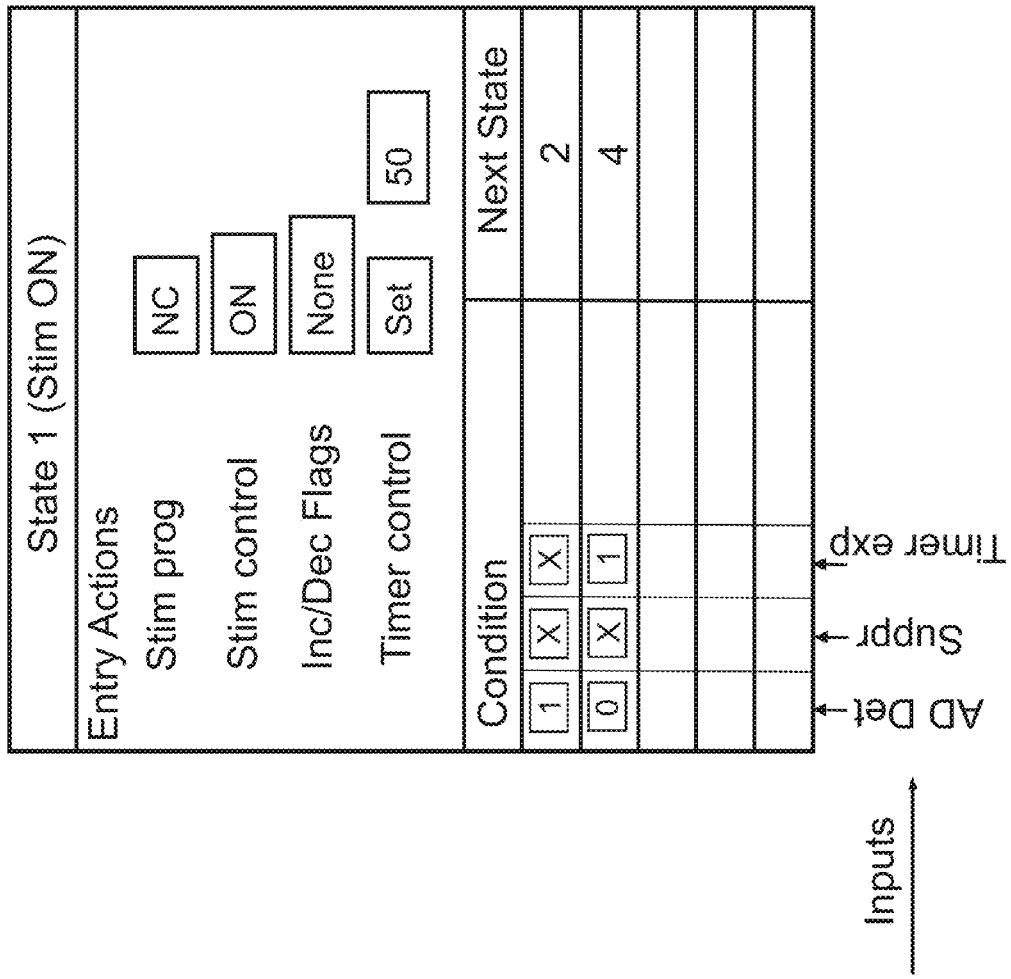
Figure 25:
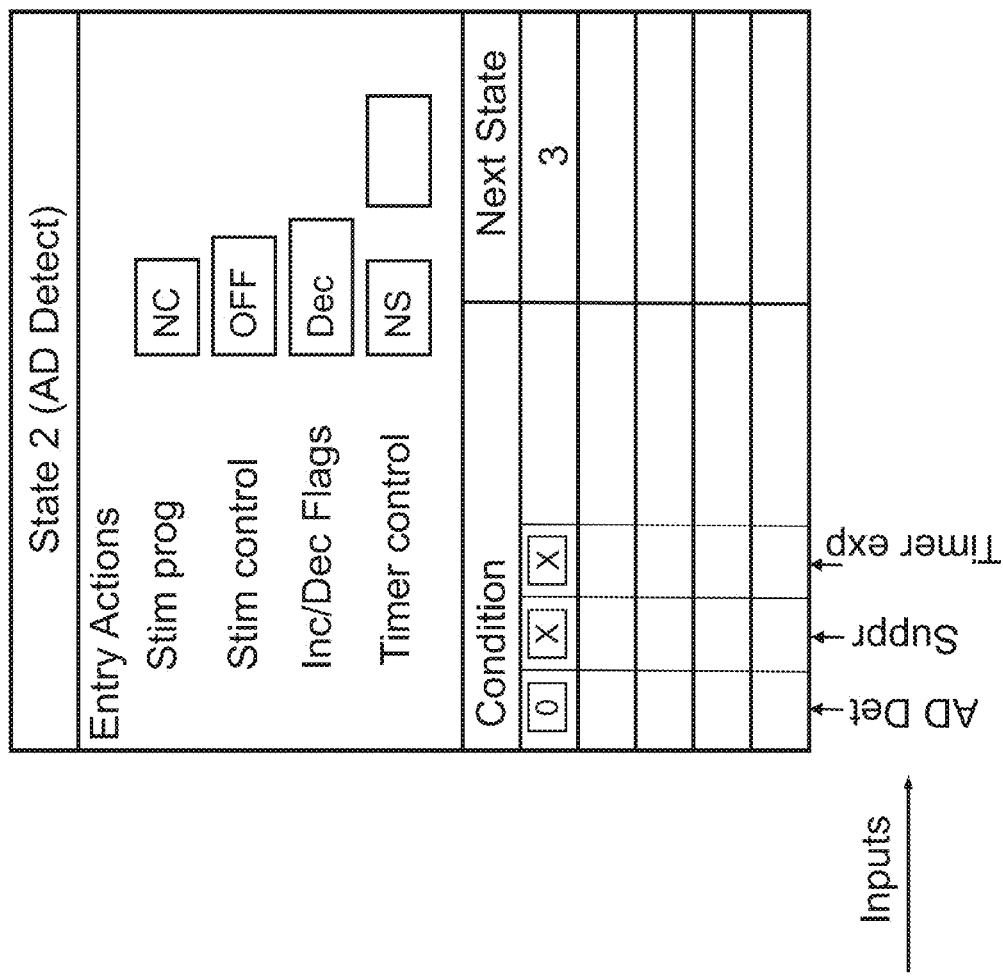
Figure 26:
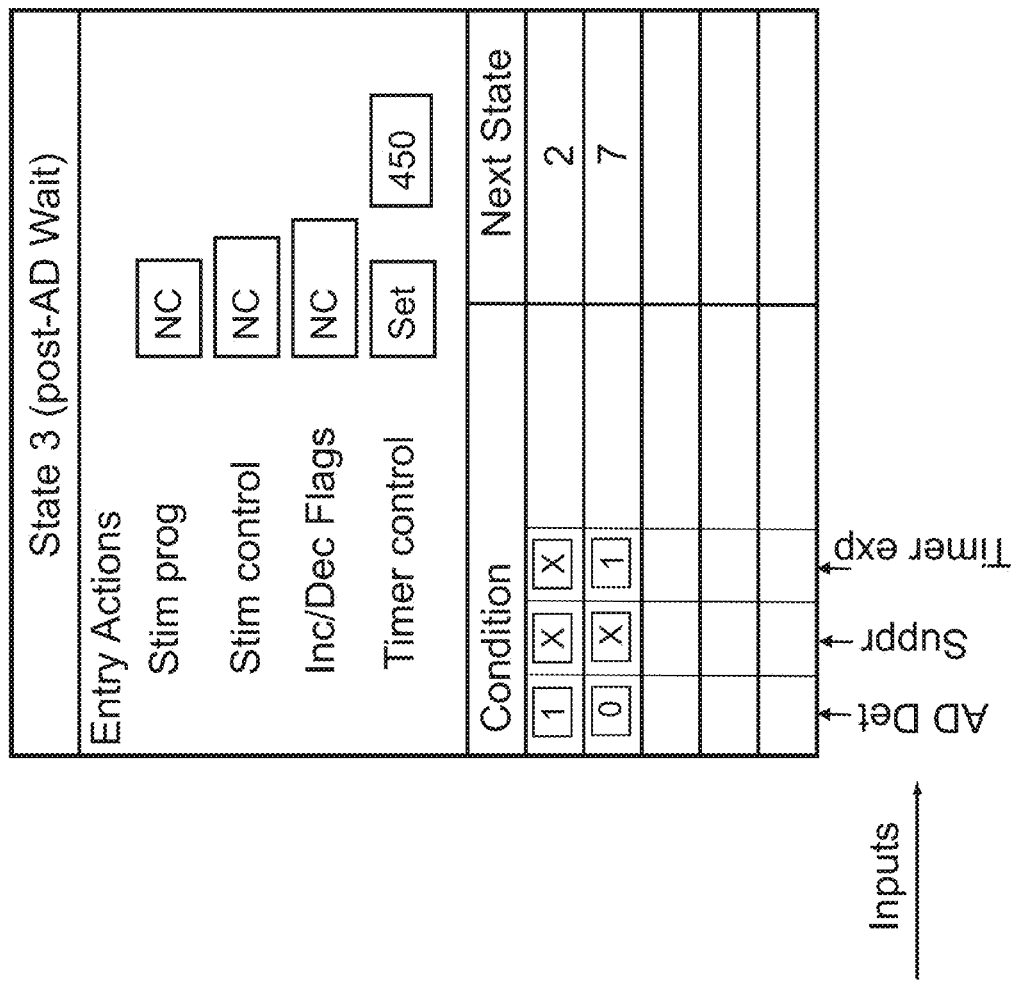
Figure 27:
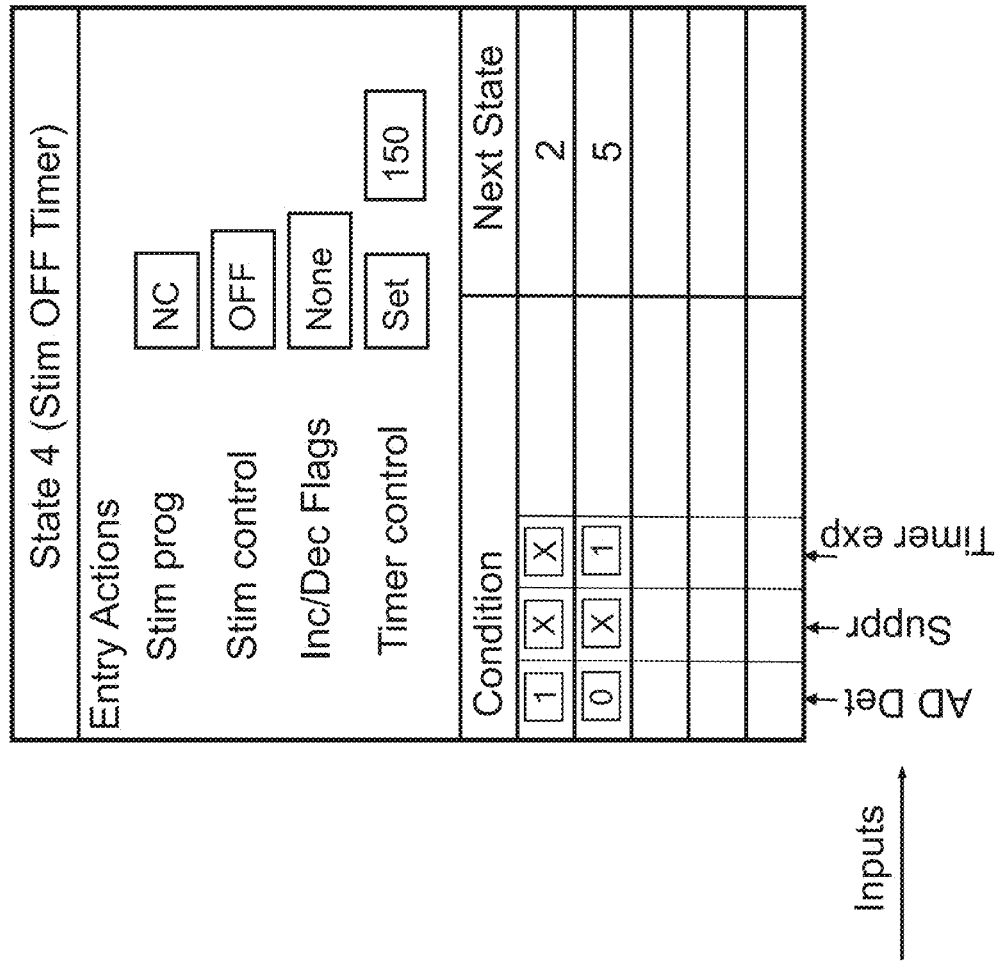
Figure 29:
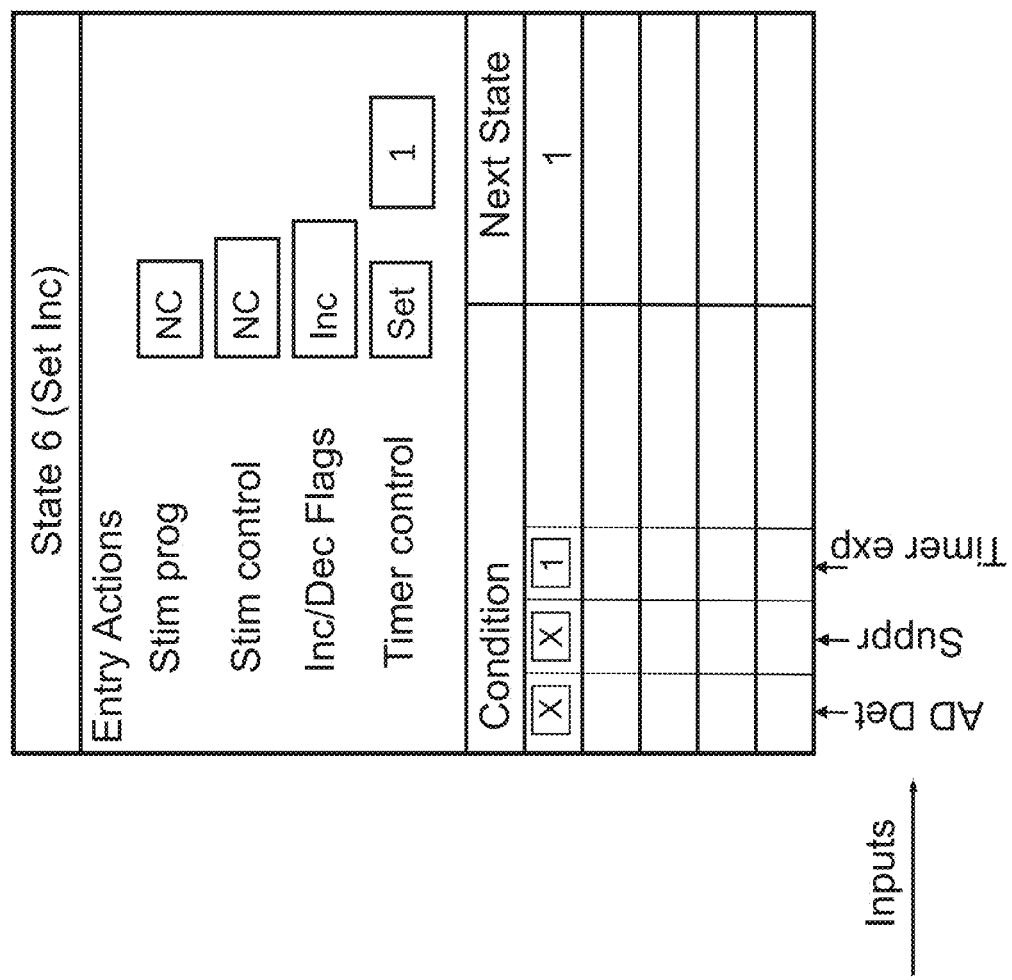
Figure 30:
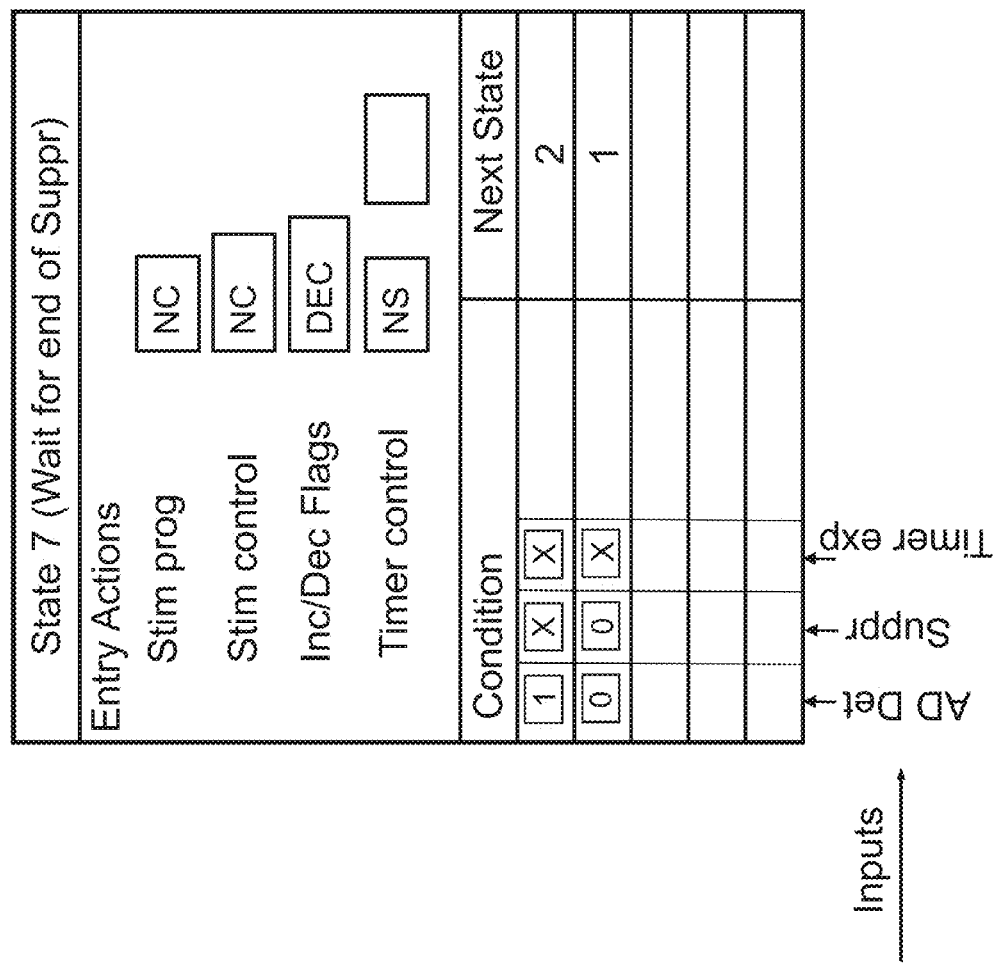

FIG. 22 is a conceptual diagram of an example state framework dialog box template 158 that may be used to implement the homeostasis control policy algorithm shown in FIG. 21. State framework dialog box template 158 shown in FIG. 22 is similar to state framework dialog box template 136 in FIG. 13 except that timer count field 150 in FIG. 13 has been replaced by two fields—a first field to indicate whether the timer count field is set (i.e., takes on values of Set or NS (i.e., "Not Set")) and a second field to indicate the value to use for the timer. In addition, timeout next state field 152 has been removed. Instead of timeout next state field 152, state framework dialog box template 158 includes a timer expiration event as an input value that may be used in the exit conditions.

FIGS. 23-30 are conceptual diagrams illustrating example state framework dialog boxes in which state parameters have been entered for the state diagram illustrated in FIG. 21. The entering of the state parameters may be used to program and/or initialize the state machine implemented by the state machine framework of this disclosure. The format of the state framework dialog boxes is substantially similar to state framework dialog box template 158 discussed above with respect to FIG. 22. Accordingly, for the sake of brevity and to avoid redundancy, the fields in the dialog boxes will not be described in further detail. It should be noted that, in this example, the field that indicates the value to set the state timeout timer is configured to receive values in units of ticks, which may correspond to processing cycles. In this example, 1 tick may correspond to 200 ms.

FIG. 31 is a state transition table corresponding to the state diagram illustrated in FIG. 21. CL3 and CL4/M4 are not shown because they were not used as inputs with this algorithm. In some cases, the state transition table shown in FIG. 31 may depict how the example homeostasis control policy algorithm is stored in internal memory (e.g., memory 34 of IMD 16). In some examples, once the table has been sent to IMD 16, the algorithm may be enabled and the system may run in closed-loop mode.

In some examples, each state may be implemented in 19 bytes for a total storage requirement of 8×19=152 bytes (times 8 for states 0-7 in this algorithm) for the states. In additional examples, the firmware for the state machine runtime environment may be generated using a microchip compiler for a microprocessor (e.g., an 8-bit microprocessor). In some examples, the microprocessor may be a sense processor. In some cases, the code size for the state machine runtime environment may be approximately 2500 bytes. The ram space used for variables may be approximately 400 bytes.

It should be noted that other implementations of a control policy framework (e.g., number of classifiers, and stimulation control, etc.) may be modified to adjust for the number of detectors or stimulation programs in the system. In some cases, these parameters may be determined prior to developing an implantable firmware code set.

FIG. 32 is a state transition table corresponding to the state diagram illustrated in FIG. 21. In some cases, the state transition table shown in FIG. 32 may depict how the example homeostasis control policy algorithm is stored in internal memory (e.g., memory 34 of IMD 16). For example, state parameters corresponding to the fields in the state transition table may, in some examples, be grouped together by state when stored in a memory. In some cases, for each of the states, a list of the entry action parameters may be followed by a list of the exit condition parameters for each of the exit conditions associated with the state. These parameters may correspond to the fields in the state transition table. In some examples, each of the fields in the state transition table may be stored as a single byte. In some examples, once the table has been sent to IMD 16, the algorithm may be enabled and the system may run in closed-loop mode.

Figure 33:
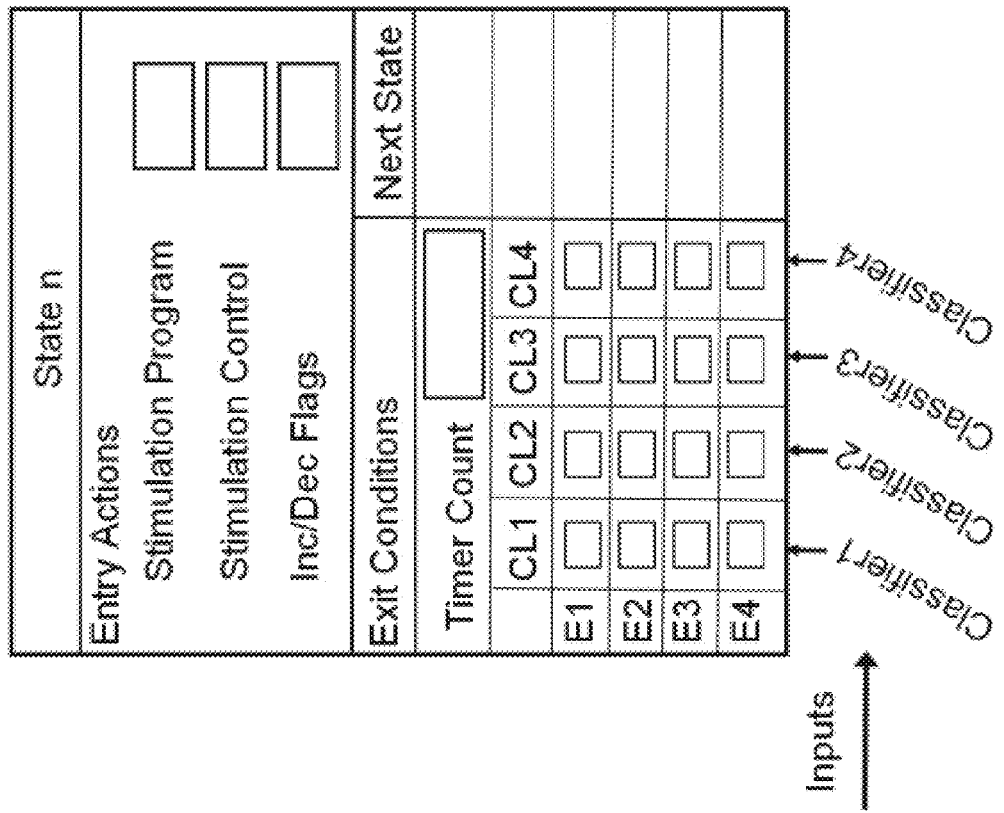
FIG. 33 is a conceptual diagram of another example state framework dialog box template that may be used to implement the homeostasis control policy algorithm shown in FIG. 21.

FIG. 33 is a conceptual diagram of another example state framework dialog box template 160 that may be used to implement the homeostasis control policy algorithm shown in FIG. 21. State framework dialog box template 160 shown in FIG. 33 is similar to state framework dialog box template 136 in FIG. 13 except that mask bits are not included as part of the classifier inputs.

Figure 34:
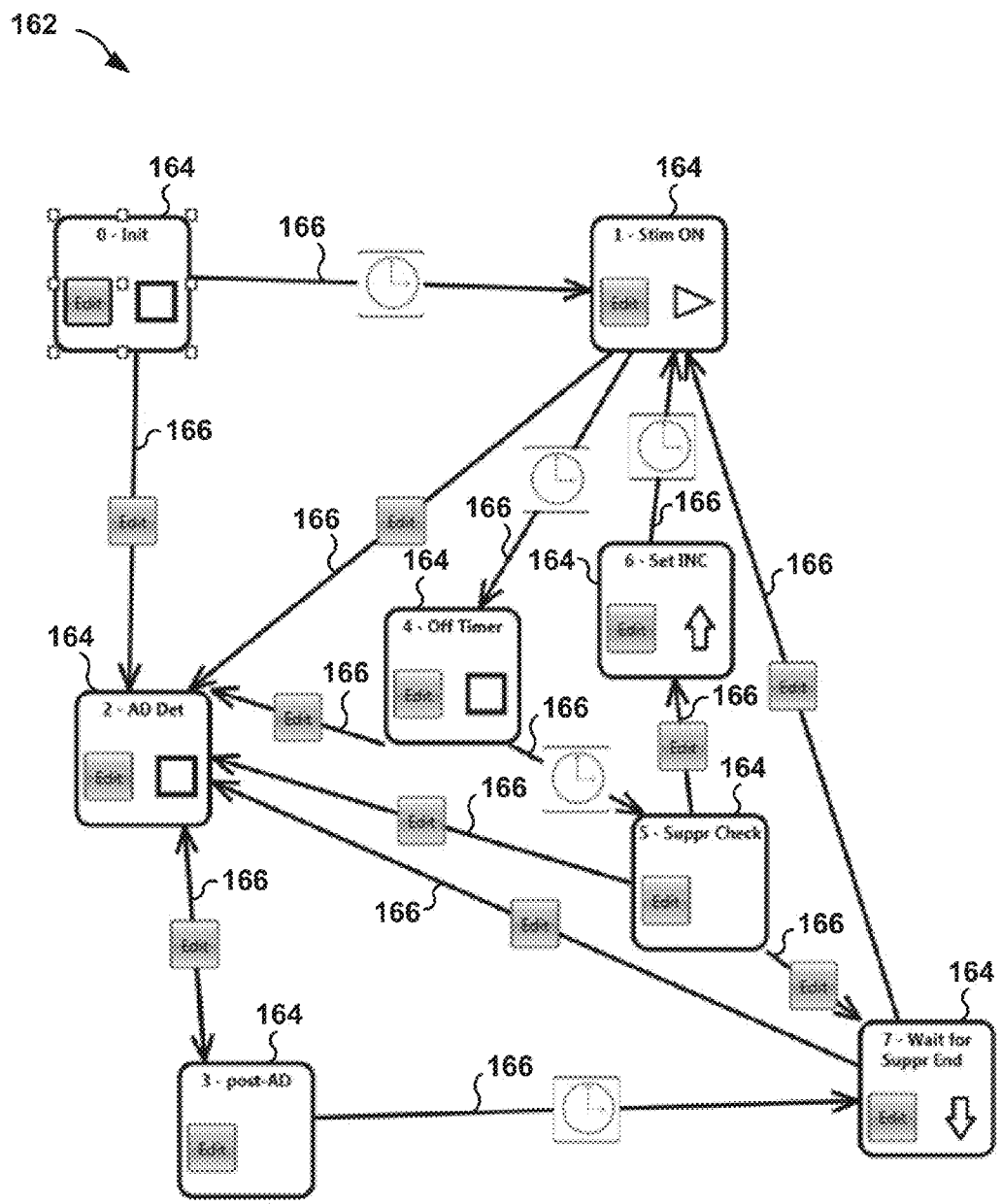
FIG. 34 is a screen shot illustrating an example state diagram that may be graphically displayed with a user interface described in this disclosure.

FIG. 34 is a screen shot illustrating an example state diagram 162 that may be graphically displayed with a graphical user interface described in this disclosure. State diagram 162 includes state nodes 164 and state transition arcs 166 that connect state nodes 164. In some examples, state nodes 164 and state transition arcs 166 may be manipulated by a user. For example, a user may drag state nodes 164 and/or state transition arcs 166 to different locations on the display. As another example, a user may connect, disconnect, or change the connections between various state nodes 164 with state transition arcs 166.

Figure 35:
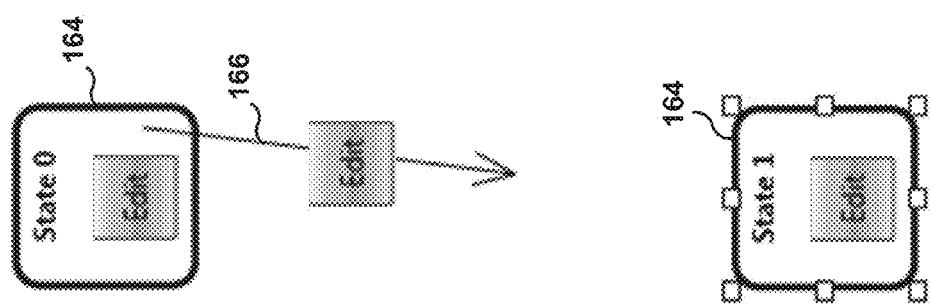
FIG. 35 is a screen shot illustrating a state transition arc that may be drawn between two different state nodes.

FIG. 35 is a screen shot illustrating a state transition arc 166 that may be drawn between two different state nodes 164. The screen shot shown in FIG. 35 illustrates that each of state nodes 164 and state transition arc 166 has a configuration tool (i.e., a box that is labeled "edit"). A user may click on the configuration tool to bring up a configuration dialog box for the particular state node or state transition arc associated with the configuration tool. In FIG. 34, the configuration tool icons for some of the state transition arcs 166 are clocks to indicate that such state transition arcs 166 are associated with timeout conditions.

Figure 36:
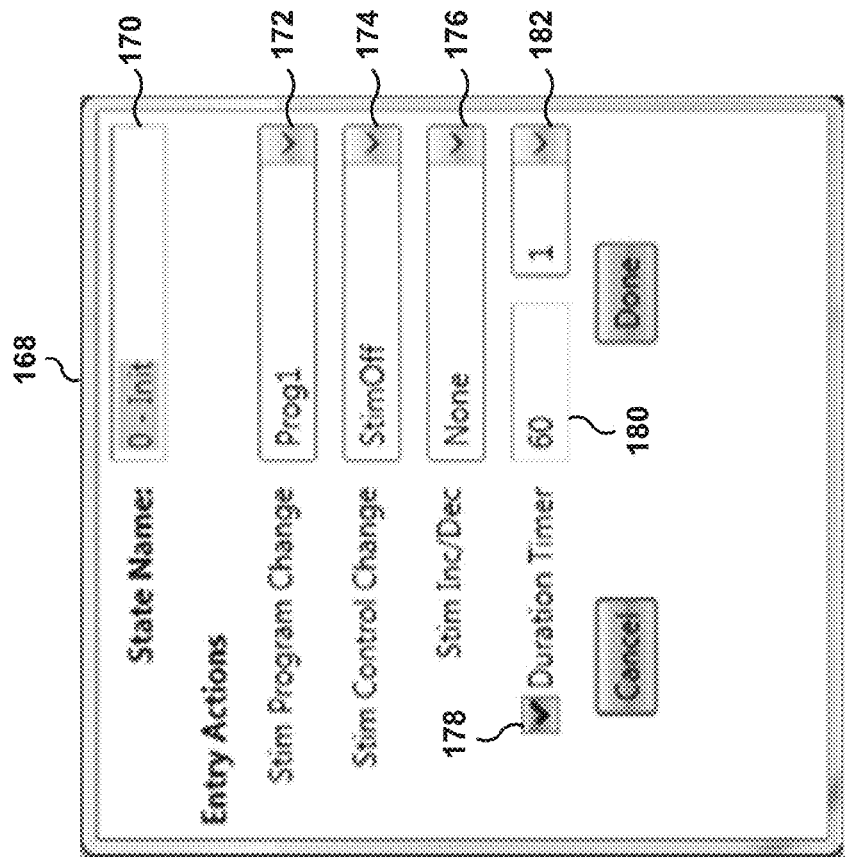
FIG. 36 is a screen shot illustrating a state builder dialog box that may appear in response to clicking a configuration tool associated with a state node in FIG. 34.

FIG. 36 is a screen shot illustrating a state builder dialog box 168 that may appear in response to clicking the configuration tool associated with State 0 in FIG. 34. State builder dialog box 168 contains fields for a user to program entry actions for the state. The entry action fields are similar to entry action fields 140 discussed above with respect to FIG. 13. As shown in FIG. 36, state builder dialog box 168 includes a state identifier field 170, a stimulation program field 172, a stimulation control field 174, an increment/decrement flag field 176, a timeout timer activation checkbox 178, a timer count field 180, and a timeout next state field 182. The values entered into each of the fields may be the same as the corresponding fields described above with respect to state framework dialog box template 136 shown in FIG. 13. Timeout timer activation checkbox 178 may allow a user to indicate whether the state timeout timer is to be activated or deactivated for the particular state identified by state identifier field 170.

State builder dialog box 168 illustrated in FIG. 36 is just one example of a dialog box that may appear when clicking on a state. In other examples, other types of dialog boxes may be used (e.g., dialog boxes similar to state framework dialog box template 136 shown in FIG. 13, state framework dialog box template 158 shown in FIG. 22 and/or state framework dialog box template 160 shown in FIG. 33).

Figure 37:
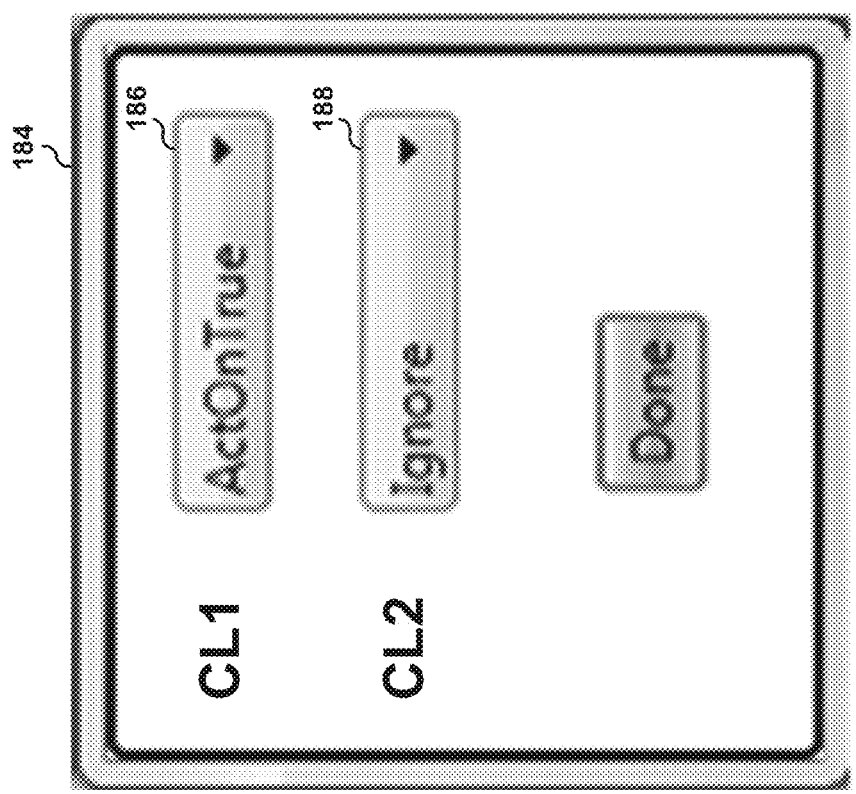
FIG. 37 is a screen shot illustrating a state transition arc dialog box that may appear in response to clicking a configuration tool associated with a state transition arc in FIG. 34.

FIG. 37 is a screen shot illustrating a state transition arc dialog box 184 that may appear in response to clicking the configuration tool associated with one of the state transition arcs 166 in FIG. 34. State transition arc dialog box 184 contains fields for a user to program exit conditions for the state from which the state transition arc corresponding to state transition arc dialog box 184 originated. As shown in FIG. 37, state transition arc dialog box 184 includes exit condition fields 186, 188. Exit condition field 186 is associated with the CL1 classifier, and exit condition field 188 is associated with the CL2 classifier. The value for each of exit condition fields 186, 188 may be selected from a drop-down list of values. The possible values that may be selected for exit condition fields 186, 188 include "ActOnTrue," "ActOnFalse," and "Ignore." The ActOnTrue," "ActOnFalse," and "Ignore" values may correspond to the values of "1," "0," and "X," respectively, that were discussed above with respect to exit condition fields 142 in FIG. 13.

The values in exit condition fields 186, 188 may collectively indicate a combination or combinations of classifier inputs that need to be satisfied for a state transition represented by the state transition arc corresponding to state transition arc dialog box 184 to occur. The "ActOnTrue" value indicates that the associated classifier must be true (i.e., the classifier detects, senses, and/or classifies a patient state) in order to perform the state transition corresponding to state transition arc dialog box 184. The "ActOnFalse" value indicates that the associated classifier must be false (i.e., the associated classifier does not detect, sense, and/or classify a patient state) in order to perform the state transition corresponding to state transition arc dialog box 184. The "Ignore" value indicates that it does not matter whether the associated classifier is true of false. In other words, the state transition corresponding to state transition arc dialog box 184 may be performed regardless of whether the classifier is true or false provided the other conditions are satisfied.

State transition arc dialog box 184 illustrated in FIG. 37 is just one example of a dialog box that may appear when clicking on a state transition arc. In other examples, other types of dialog boxes may be used (e.g., dialog boxes similar to state framework dialog box template 136 shown in FIG. 13, state framework dialog box template 158 shown in FIG. 22 and/or state framework dialog box template 160 shown in FIG. 33).

In some examples, the user interfaces of this disclosure may include a set of icons that act as a "toolbox" where the user can drag them to create partially predefined states, such as a state that will increment a stimulation parameter (e.g., stimulation amplitude). In other words, a user may be able to drag and drop states into the state diagram from a pre-defined set of states. This may allow for easier building of a state machine. In other examples, the toolbox may include tools other than those illustrated in addition to or lieu of the illustrated tools.

The user interfaces described in this disclosure may, in some examples, facilitate the development of closed loop algorithms by researchers and by users of commercially released products. In further examples, the user interfaces described in this disclosure may support various firmware features described in this disclosure. The user interfaces described in this disclosure may, in some cases, allow a user to build a generic, flexible closed loop algorithm that can be downloaded into an implantable neurostimulator (INS). This may allow for the downloading of parameters according to a defined INS-Instrument interface, instead of requiring a complete firmware download. The user interfaces described in this disclosure may, in some examples, utilize a drag and drop set of commonly used states, creation of custom states, and moving and toggling the links between various states.

The user interfaces described in this disclosure may provide an intuitive and easy way to develop algorithms for closed loop therapy. However, the user interfaces are not limited to the development of closed loop therapy algorithms, and may also be used to develop algorithms in additional situations where a state machine approach may be useful.

In some examples, the user interfaces described in this disclosure may support one or more of the following features: ability to drag and drop states from a pre-defined "toolbox" of common states; ability to customize the icons and images associated with states; ability to customize a state using a "state-builder;" ability to draw custom states and draw links between states; ability to define the conditions (e.g., from a variety of sources such as sensors, timers, etc.) that cause a state transition; ability to configure the actions that occur when a state is entered (stimulation changes); ability to save and recall templates and previously created algorithms; ability to create a table report of the created algorithm states and transitions; and ability to allow a user to follow a wizard-like user-interface to facilitate algorithm development.

In further examples, a user interface may include a wizard that asks questions of the user, and generates the state machine based on answers to the questions received from the user. In additional examples, a user interface may present templates to a user, and generate the state machine based on user input received via the templates.

The graphical user interfaces described in this disclosure may facilitate the process of creating control policy algorithms. The user interfaces may contain a drag and drop state machine builder that allows states to be connected together. Entry actions and exit conditions may be specified via dialog boxes, and the algorithm may run through a rule checker to ensure consistency. A state machine table may be automatically derived when a user directs the user interface to send the state machine to another device. Libraries of algorithms may be developed, shared, and modified. This may allow users who are not state machine designers to develop algorithms with relative ease.

The techniques of this disclosure may be used, in some examples, to implement a control policy algorithm with a general-purpose state framework. When implementing a closed loop algorithm in an implantable neurostimulator device, it may be desirable that the control policy algorithm used is flexible enough to allow for configurable execution paths. In some types of implantable devices with embedded firmware, this may require that new control policy algorithm firmware code be downloaded via telemetry anytime a change in execution method is desired. If a control policy that is performed by the neurostimulator was designed as a state machine, and if a user decides to change any of the state transitions, remove a state, or add an additional state, the firmware algorithm code, in such examples, may need to be updated.

There may be several drawbacks associated with downloading new firmware into an implantable device. One drawback is that it takes time to transmit and verify new firmware downloads. Another drawback is that downloading new firmware shortens the implantable device battery life due to high current drain during the download process. Moreover, there is a risk that the download may be corrupted or not successfully completed without retries. In addition, each new firmware version may require a firmware development, verification, test, and approval cycle. Moreover, external instrument software may need to be changed to support new algorithm parameters.

The techniques of this disclosure may, in some examples, implement a general-purpose framework for closed-loop state machine processing in the implantable firmware where the state machine is defined by downloadable state parameters instead of by firmware code. This may, in some examples, allow a user or engineering team to build a control policy algorithm. In some cases, the state parameters may be downloaded relatively quickly (e.g., seconds vs. minutes) and with much lower risk than that associated with a code update. The flexible framework described in this disclosure may allow a control policy algorithm to be readily modified, such as the number of states and their transitions (within limits of the finite memory of the embedded system).

In some examples, one or more checks may be implemented to help maintain safe operating or to help ensure adequate safety of an implantable neurostimulator device in which the techniques of this disclosure may be implemented. One type of check that may be implemented is state error handling. With this check, any attempt to enter an illegal state (e.g., one that is not implemented) due to corrupted state memory, etc., may cause the state processing to enter a designated safe state. The safe state may be a dedicated state that may cause the therapy to revert to a default setting programmed by an attending clinician.

Another type of check that may be implemented is a manual override. With this check, any manual change to the therapy initiated either by a patient or a clinician may cause the automated closed loop therapy algorithm to stop all therapy control until restarted with an explicit external command.

Another type of check that may be implemented is therapy limit settings. With this check, parameters may be added to the framework that limit the minimum and maximum amplitudes controlled by the algorithm.

Another type of check that may be implemented is a supervisory task. With this check, a separate supervisory task may be used to monitor the therapy control in order to monitor the amount of time that therapy was turned off or on and intervene if either condition exceeds the programmed time setting.

In some examples, the control policy framework of this disclosure may include diagnostic and operating trend statistics to aid with troubleshooting or to show patient efficacy while the closed loop algorithm is operating. For example, the control policy framework of this disclosure may provide an indication of state status. The indication of state status may include a status block indicating the current vitals (e.g., current state, controlling stimulation, not controlling stimulation, etc.) of the control policy algorithm that are available for interrogation with the external instrument. In some cases, the user interface may allow for real-time monitoring of state machine status to track the flow of the state machine.

As another example, the control policy framework of this disclosure may provide a state counter. The state counter may be a counter that is incremented each time a state is entered. Such a counter may be useful in determining if the implemented algorithm is operating correctly (e.g., not being stuck in one state, or continually toggling states, etc.). In some examples, the user interface may display a heat map that overlays the states in a state diagram, and the heat map may indicate the absolute and/or relative time spent by the state machine in each of the states. In further examples, the user interface may include a playback feature that allows a user to see various status metrics (e.g., the heat map) change over time during the execution of the state machine.

As a further example, the control policy framework of this disclosure may provide a state execution histogram. A state execution histogram may show the amount of time spent in each state. A state execution histogram may be used to show the percentage of time spent in "stim-on" states vs. "stim-off" states.

As a further example, the control policy framework of this disclosure may provide a state history. The state history may, in some examples, be a circular buffer (i.e., a shallow history) which may hold the last predetermined number of state transitions. A state history may be useful in trouble-shooting the execution path to a "stuck state" scenario.

In some examples, the techniques of this disclosure may provide one or more advantages. For example, the techniques of this disclosure may provide a framework for a general control policy for an embedded neurostimulator system, provide a flexible method to implement a closed loop control algorithm, allow for relatively quick parameter changes to tweak the control execution (e.g., adding/removing states, transitions, stimulation control), provide a programming framework where state machines may be programmed by downloading parameters instead of downloading firmware code; allow changes to be made to closed loop operation relatively quickly without overhead of requalification of a new algorithm in firmware once the initial development, debug and testing of the firmware is completed, allow a library of control algorithms to be created and stored on an external programming instrument, allow users to create their own customized control algorithms, allow a flexible, configurable, control policy framework to be implemented on an implantable device with a firmware overhead (i.e., time of execution) of the general control policy that is on par with a fixed, non-configurable, control policy.

Modulation of neural activity through electrical stimulation of tissue may be an effective therapy for neurological diseases such as Parkinson's disease and essential tremor. The techniques of this disclosure may, in some examples, be used to improve therapy through adjustment of stimulation parameters based upon sensed data. In some cases, the techniques of this disclosure may use classifiers to interpret biomarkers and algorithms to map the outputs of these classifiers to control stimulation therapy. The techniques of this disclosure may be useful, in some cases, because the exact nature of optimal control policy algorithms to be used in particular situations is not fully known in advance and to provide flexibility. The techniques of this disclosure may provide, in some examples, a generic control policy framework.

Neurostimulators have been used for decades to treat symptoms of neurological diseases such as Parkinson's disease and essential tremor. This therapy is called deep brain stimulation (DBS). Factors that may need to be considered in order to provide effective DBS therapy include electrode placement and selection of stimulation parameters (e.g., amplitude, pulse width, and frequency).

Some types of neurostimulators may require that the clinician be in the loop to program the stimulation parameters. This largely empirical procedure is often very time-consuming and programming sessions may be weeks or months apart. Patients receive a patient programmer that can be used to make limited adjustments.

The techniques of this disclosure may provide sensing capabilities for implantable neurostimulators. Sensing capabilities may allow a neurostimulator to be able to "close the loop" and modify stimulation parameters to adjust the therapy to changing conditions. In some cases, the techniques of this disclosure may use one or more classifiers to extract information from sensed signals to provide a state estimate. Once a state estimate is determined, a control policy algorithm may be used to make therapeutic decisions.

There are many factors that may be considered when designing a control policy algorithm for a closed-loop neurostimulator. One factor is that optimal algorithms are often unknown. Development of control policy algorithms for closed loop neuromodulation systems is at a relatively early stage. The techniques of this disclosure provide a flexible framework to develop and test new algorithms. The techniques of this disclosure may also allow users and programmers to explore an algorithm space that may be unknown.

Another factor to consider when designing a control policy algorithm for a closed-loop neurostimulator is the process of firmware verification and validation. Classifiers and control policy algorithms may be implemented in the firmware of an implantable neurostimulator. In some cases, this firmware may need to pass a rigorous set of testing before it is allowed to be used in a clinical setting. If each control policy algorithm requires new firmware, each firmware version may require a full cycle of development, verification, test, and approval. Avoiding this burden may be desirable.

Another factor to consider when designing a control policy algorithm for a closed-loop neurostimulator is the relatively small study size to which a researcher may have access. Research studies often involve a small number of subjects. In many cases, it is not economically feasible to provide a different set of firmware for each study.

The techniques of this disclosure may provide a general-purpose framework based upon state machines to allow a user to build control policy algorithms in an implantable neurostimulator. The state parameters may, in some examples, be downloaded relatively quickly and with much lower risk than a code update. The flexible framework described in this disclosure may, in some cases, allow a control policy algorithm to be readily modified, such as updating the number of states and their transitions (within limits of the finite memory of the embedded system).

To provide flexibility in designing, testing, and modifying control policy algorithms, the techniques of this disclosure may provide a system where each algorithm is a collection of states. Each state may have entry actions that can affect stimulation therapy and exit conditions that are selectively based upon classifier states and the state of a timer.

The generic control policy framework of this disclosure may provide a flexible method of building control policy algorithms that are compatible with the architecture of the implantable neurostimulator. A library of such algorithms may be built by researchers and/or an engineering team. This may be done, in some cases, without the burden of firmware updates for each algorithm. The techniques of this disclosure may provide a flexible framework for building control policy algorithms, which may be used to develop DBS therapies involving closed-control of neuromodulation devices.

Although the examples in this disclosure have been described with respect to using programmable state machines to control the delivery of therapy based on sensed states of a patient, in other examples, the programmable state machines may be used for other purposes in addition to or in lieu of controlling the delivery of therapy based on sensed states of a patient. For examples, similar types of programmable state machines may be used to provide "closed loop sensing" where the state machine determines what to sense and/or what control parameters to use for various sensors based on one or more sensed states of a patient. Other examples are also possible.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various examples of the disclosure have been described. These and other examples are within the scope of the following claims.

What is claimed is:

1. A method comprising:
   executing a state-machine runtime environment by an implantable medical device (IMD), wherein the state-machine runtime environment is configurable to implement two or more state machines based on programmable state parameters;
   obtaining one or more of the programmable state parameters to implement one of the state machines on the state-machine runtime environment executed by the IMD; and
   controlling delivery of therapy by the IMD to a patient based on the state machine, wherein the state machine generates one or more therapy decisions to control the delivery of the therapy based on one or more sensed states of the patient, the state machine having a structure that is defined at least in part by the one or more programmable state parameters.

2. The method of claim 1, further comprising:
   receiving, with the IMD, the one or more programmable state parameters from a device other than the IMD.

3. The method of claim 2, wherein the device other than the IMD is a programmer device.

4. The method of claim 1, wherein the sensed states of the patient comprise one or more binary values, each of the binary values being indicative of whether a respective one of one or more physiological states has been detected for the patient based on data received from one or more physiological sensors.

5. The method of claim 1, wherein the one or more programmable state parameters comprise a state parameter that specifies a number of states included in the state machine.

6. The method of claim 1, wherein the one or more programmable state parameters comprise one or more state parameters that specify a state transition function for the state machine.

7. The method of claim 1, wherein the one or more programmable state parameters comprise one or more state parameters that specify one or more entry actions for one or more states in the state machine.

8. The method of claim 7, wherein the one or more entry actions comprise one or more of an action that selects one of a plurality of stimulation programs to be used for delivery of stimulation, an action that turns on the delivery of the stimulation, an action that turns off the delivery of the stimulation, an action that causes no change to an activation state of the stimulation, an action that increases an amplitude of the stimulation, an action that decreases the amplitude of the stimulation, an action that increases a pulse width of the stimulation, an action that decreases the pulse width of the stimulation, an action that increases a frequency of the stimulation, an action that decreases the frequency of the stimulation, an action that causes a timeout to occur if no exit conditions are satisfied after a specified period of time.

9. The method of claim 1, wherein the one or more programmable state parameters comprise one or more state parameters that specify one or more exit conditions for one or more states in the state machine, each of the exit conditions including a respective condition portion that specifies a condition to be evaluated and a respective next state portion that specifies to which state the state machine is to transition if the condition specified in the condition portion is satisfied.

10. The method of claim 9, wherein the condition portion specifies a combination of one or more of a plurality of state classifier outputs, each of the state classifier outputs being indicative of whether a respective one of one or more physiological states has been detected for the patient based on data received from one or more physiological sensors.

11. The method of claim 1, wherein controlling the delivery of therapy by the IMD based on the state machine comprises:
controlling the delivery of therapy by the IMD based on one or more entry actions that are associated with a current state in the state machine, the one or more entry actions associated with the current state being specified by the programmable state parameters;
determining whether one or more exit conditions that are associated with the current state are satisfied, the one or more exit conditions associated with the current state being specified by the programmable state parameters;
in response to determining that at least one of the exit conditions is satisfied, determining a next state in the state machine based on the at least one of exit conditions that is satisfied; transitioning to the next state in the state machine; and
controlling the delivery of therapy by the IMD based on one or more entry actions that are associated with the next state in response to transitioning to the next state, the one or more entry actions associated with the next state being specified by the programmable state parameters.

12. The method of claim 1, further comprising:
receiving, with a device other than the IMD, the programmable state parameters from a user via a user interface; and
transmitting the programmable state parameters from the device other than the IMD to the IMD.

13. The method of claim 1, further comprising:
presenting, with a user interface executing on a device other than the IMD, a graphical representation of a state diagram that includes components that are capable of being manipulated by a user;
receiving user input that manipulates one or more of the components of the state diagram to generate a user-manipulated state diagram;
presenting, with the user interface, a graphical representation of the user-manipulated state diagram;
generating the programmable state parameters for the state machine based on the user-manipulated state diagram; and
transmitting the programmable state parameters from the device other than the IMD to the IMD.

14. The method of claim 13, wherein the components that are capable of being manipulated by the user include state nodes and state transition arcs.

15. The method of claim 1, wherein the sensed states of the patient include a sensed brain state of the patient, and wherein the therapy decisions include a therapy decision to deliver therapy to a brain of the patient.

16. An implantable medical device (IMD) comprising:
a therapy delivery device configured to deliver therapy to a patient; and
one or more processors configured to execute a state-machine runtime environment that is configurable to implement two or more state machines based on programmable state parameters, obtain one or more programmable state parameters to implement a state machine on the state-machine runtime environment; and control delivery of the therapy by the therapy delivery device to the patient based on a state machine that generates one or more therapy decisions to control the delivery of the therapy based on one or more sensed states of the patient, the state machine having a structure that is defined at least in part by the one or more programmable state parameters.

17. The device of claim 16, wherein the one or more processors are further configured to receive the one or more programmable state parameters from a device other than the IMD.

18. The device of claim 17, wherein the device other than the IMD is a programmer device.

19. The device of claim 16, wherein the sensed states of the patient comprise one or more binary values, each of the binary values being indicative of whether a respective one of one or more physiological states has been detected for the patient based on data received from one or more physiological sensors.

20. The device of claim 16, wherein the one or more programmable state parameters comprise a state parameter that specifies a number of states included in the state machine.

21. The device of claim 16, wherein the one or more programmable state parameters comprise one or more state parameters that specify a state transition function for the state machine.

22. The device of claim 16, wherein the one or more programmable state parameters comprise one or more state parameters that specify one or more entry actions for one or more states in the state machine.

23. The device of claim 22, wherein the one or more entry actions comprise one or more of an action that selects one of a plurality of stimulation programs to be used for delivery of stimulation, an action that turns on the delivery of the stimulation, an action that turns off the delivery of the stimulation, an action that causes no change to an activation state of the stimulation, an action that increases an amplitude of the stimulation, an action that decreases the amplitude of the stimulation, an action that increases a pulse width of the stimulation, an action that decreases the pulse width of the stimulation, an action that increases a frequency of the stimulation, an action that decreases the frequency of the stimulation, an action that causes a timeout to occur if no exit conditions are satisfied after a specified period of time.

24. The device of claim 16, wherein the one or more programmable state parameters comprise one or more state parameters that specify one or more exit conditions for one or more states in the state machine, each of the exit conditions including a respective condition portion that specifies a condition to be evaluated and a respective next state portion that specifies to which state the state machine is to transition if the condition specified in the condition portion is satisfied.

25. The device of claim 24, wherein the condition portion specifies a combination of one or more of a plurality of state classifier outputs, each of the state classifier outputs being indicative of whether a respective one of one or more physiological states has been detected for the patient based on data received from one or more physiological sensors.

26. The device of claim 16, wherein the one or more processors are further configured to: control the delivery of therapy by the IMD based on one or more entry actions that are associated with a current state in the state machine, the one or more entry actions associated with the current state being specified by the programmable state parameters;
- determine whether one or more exit conditions that are associated with the current state are satisfied, the one or more exit conditions associated with the current state being specified by the programmable state parameters;
- in response to determining that at least one of the exit conditions is satisfied, determine a next state in the state machine based on the at least one of exit conditions that is satisfied; transition to the next state in the state machine; and
- control the delivery of therapy by the IMD based on one or more entry actions that are associated with the next state in response to transitioning to the next state, the one or more entry actions associated with the next state being specified by the programmable state parameters.

27. The device of claim 26, wherein the components that are capable of being manipulated by the user include state nodes and state transition arcs.

28. The device of claim 16, wherein the sensed states of the patient include a sensed brain state of the patient, and wherein the therapy decisions include a therapy decision to deliver therapy to a brain of the patient.

29. A system comprising:
- an implantable medical device (IMD) comprising a therapy delivery device configured to deliver therapy to a patient, and one or more processors configured to execute a state-machine runtime environment that is configurable to implement two or more state machines based on programmable state parameters, obtain one or more programmable state parameters to implement a state machine on the state-machine runtime environment, and control delivery of the therapy by the therapy delivery device to a patient based on a state machine that generates one or more therapy decisions to control the delivery of the therapy based on one or more sensed states of the patient, the state machine having a structure that is defined at least in part by the one or more programmable state parameters; and
- a programmer configured to receive the programmable state parameters from a user via a user interface, and to transmit the programmable state parameters from the programmer to the IMD.

30. The system of claim 29, wherein the programmer is further configured to:
- present a graphical representation of a state diagram that includes components that are capable of being manipulated by a user;
- receive user input that manipulates one or more of the components of the state diagram to generate a user-manipulated state diagram;
- present a graphical representation of the user-manipulated state diagram;
- generate the programmable state parameters for the state machine based on the user-manipulated state diagram; and
- transmit the programmable state parameters from the device other than the IMD to the IMD.

* * * * *